(12) United States Patent
Jaschinski et al.

(10) Patent No.: US 11,959,083 B2
(45) Date of Patent: Apr. 16, 2024

(54) IMMUNOSUPPRESSION-REVERTING OLIGONUCLEOTIDES INHIBITING THE EXPRESSION OF CD39

(71) Applicant: Secarna Pharmaceuticals GmbH & Co. KG, Marburg (DE)

(72) Inventors: Frank Jaschinski, Puchheim (DE); Tamara Thelemann, Munich (DE)

(73) Assignee: Secarna Pharmaceuticals GmbH & Co. KG, Marburg (DE)

( * ) Notice: Subject to any disclaimer, the term of this patent is extended or adjusted under 35 U.S.C. 154(b) by 0 days.

(21) Appl. No.: 16/340,259

(22) PCT Filed: Oct. 9, 2017

(86) PCT No.: PCT/EP2017/075647
§ 371 (c)(1),
(2) Date: Apr. 8, 2019

(87) PCT Pub. No.: WO2018/065622
PCT Pub. Date: Apr. 12, 2018

(65) Prior Publication Data
US 2020/0224202 A1    Jul. 16, 2020

(30) Foreign Application Priority Data

Oct. 7, 2016 (EP) .................. 16192807
Aug. 24, 2017 (EP) .................. 17187774

(51) Int. Cl.
*C12N 15/113* (2010.01)
*A61K 48/00* (2006.01)
*A61P 35/00* (2006.01)

(52) U.S. Cl.
CPC ........ *C12N 15/1137* (2013.01); *A61P 35/00* (2018.01); *A61K 48/00* (2013.01); *C12N 2310/11* (2013.01); *C12N 2310/315* (2013.01); *C12N 2310/3231* (2013.01)

(58) Field of Classification Search
CPC ............ A61K 38/27; C12Y 302/01022; C12Y 201/03003; C12N 15/67
See application file for complete search history.

(56) References Cited

U.S. PATENT DOCUMENTS

| | | | |
|---|---|---|---|
| 2002/0049306 A1* | 4/2002 | Sakano | C07K 14/47 530/388.7 |
| 2011/0038841 A1* | 2/2011 | Ayares | A61P 3/10 424/93.21 |
| 2011/0097716 A1* | 4/2011 | Natt | C12Q 1/6851 435/6.11 |
| 2013/0273062 A1 | 10/2013 | Benussan et al. | |
| 2016/0058792 A1 | 3/2016 | Quintana et al. | |

FOREIGN PATENT DOCUMENTS

| | | |
|---|---|---|
| JP | 2011510953 A | 4/2011 |
| JP | 2014526472 A | 10/2014 |
| JP | 2016516416 A | 6/2016 |
| JP | 2016526883 A | 9/2016 |
| WO | 2003052121 A2 | 6/2003 |
| WO | 2014154843 A1 | 10/2014 |
| WO | 2016073845 A1 | 5/2016 |
| WO | 2016138278 A2 | 9/2016 |

OTHER PUBLICATIONS

Bennett and Swayze (Annu. Rev. Pharmacol. Toxicol. 2010. 50:259-93) (Year: 2010).*
Ma et al (Mol Cancer Ther 2008;7(12). Dec. 2008) (Year: 2008).*
Bastid et al (Cancer Immunol Res; 3(3): 254-265, 2015) (Year: 2015).*
Montalbán del Barrio et al (Journal for ImmunoTherapy of Cancer (2016) 4:49, 16 pages) (Year: 2016).*
Hausler et al (Am J Transl Res 2014;6(2):129-139) (Year: 2014).*
Young et al (Cancer Discov; 4(8); 879-88, 2014) (Year: 2014).*
Mak et al (Am J Transl Res 2014;6(2):114-118) (Year: 2014).*
Moncrieffe et al (J Immunol 2010; 185:134-143, and 3 pages of Supplementary Data) (Year: 2010).*
Antonoli (Trends in Molecular Medicine, 19(6): 355-367, 2013) (Year: 2013).*
Imai, M., et al., "Suppression of ATP Diphosphohydrolase/CD39 in Human Vascular Endothelial Cells", Biochemistry 1999, 38, pp. 13473-13479.
Sun, X. et al., "CD39/ENTPD1 Expression by CD4+Foxp3+ Regulatory T Cells Promotes Hepatic Metastatic Tumor Growth in Mice", Gastroenterology, vol. 139,3 (2010): 1030-1040. doi:10.1053/j.gastro.2010.05.007.
Michaud, M. et al., "Subversion of the chemotherapy-induced anticancer immune response by the ecto-ATPase CD39", Oncoimmunology, May 1, 2012;1(3):393-395. doi: 10.4161/onci.19070.
Aleu, J. et al., "Release of ATP induced by hypertonic solutions in Xenopus oocytes", J Physiol. (2003), 547,1, pp. 209-219 doi: 10.1113/jphysiol.2002.029660.

(Continued)

*Primary Examiner* — Richard A Schnizer
(74) *Attorney, Agent, or Firm* — Verrill Dana, LLP

(57) ABSTRACT

The present invention refers to immunosuppression-reverting oligonucleotides comprising 12 to 18 nucleotides, wherein at least one of the nucleotides is modified, and the oligonucleotide hybridizes with a nucleic acid sequence of an ectonucleotidase (NTPdase; CD73) of SEQ ID NO.1 (human), wherein the oligonucleotide inhibits at least 50% of the CD39 expression. The invention is further directed to a pharmaceutical composition comprising such oligonucleotide.

8 Claims, 29 Drawing Sheets
Specification includes a Sequence Listing.

(56) References Cited

OTHER PUBLICATIONS

Feng, L. et al., "Vascular CD39/ENTPD1 directly promotes tumor cell growth by scavenging extracellular adenosine triphosphate.", Neiplasia, Mar. 2011, vol. 13, No. 3, pp. 206-216 doi: 10.1593/neo.101332.

Théâtre, E. et al., "Overexpression of CD39 in Mouse Airways Promotes Bacteria-Induced Inflammation", The Journal of Immunology, Aug. 15, 2012, vol. 89 Issue 4, 1966-1974; doi: 10.4049/jimmunol.1102600.

Martins, F. et al., "Adverse effects of immune-checkpoint inhibitors: epide/miology, management and surveillance", Nature Reviews, Clinical Oncology, vol. 16, Sep. 2019, pp. 563-580.

Han, Y. et al., PD-1/PD/L1 pathway: current researches in cancer, Am. J. Cancer Res., (2020), 10(3), pp. 727-742.

Chang, E. et al., "Systematic Review of PD-1/PD-L1 Inhibitors in Oncology: From Personalized Medicine to Public Health", The Oncologist, (2021), vol. 26, pp. e1786-e1799.

Trishula Therapeutics, Press Release, Trishula Therapeutics Announces Promising Early Phase 1b Data of TTX-030, an Anti-CD39 Antibody, in Combination with Chemoimmunotherapy as First-Line Treatment for Locally Advanced or Metastatic Gastric Cancer/GEJ Cancer, downloaded on Oct. 12, 2022 from www.trishulatx.com/news/press/041222.

Hong, D. et al., AZD9150, a Next-Generation Antisense Oligonucleotide Inhibitor of STAT3 with Early Evidence of Clinical Activity in Lymphoma and Lung Cancer, Sci. Transl. Med., Nov. 28, 2015, 7(34), 23 pgs.

Reilley, M.J. et al., "STAT3 antisense oligonucleotide AZD9150 in a subset of patients with heavily pretreated lymphoma: results of a phase 1b trial", J. Immunother. Cancer, Nov. 16, 2018, 6(1), 2 pgs.

* cited by examiner

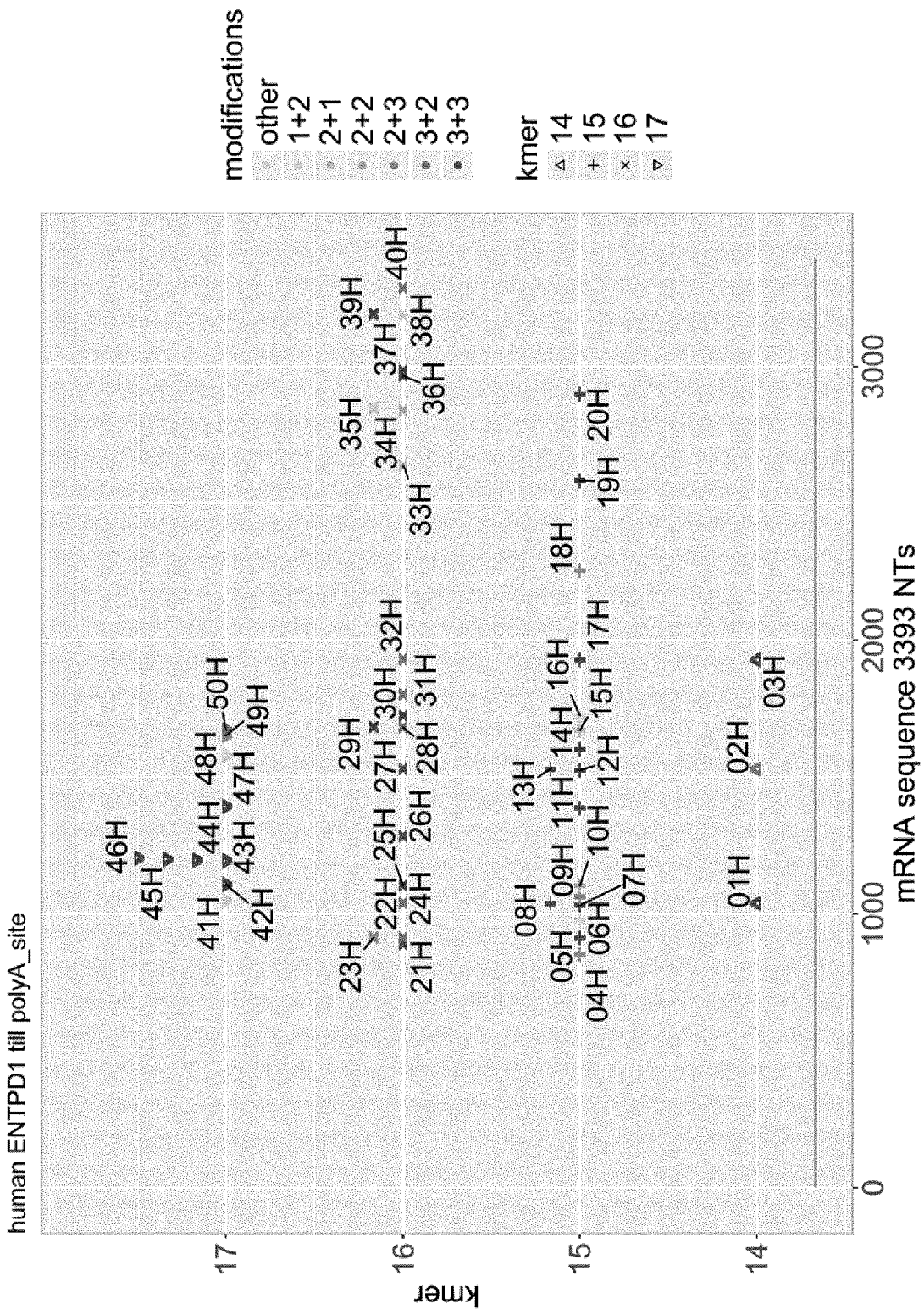
Fig. 1: Distribution of hCD39 antisense oligonucleotide binding sites on the hCD39 mRNA HDLM-2 cells (first screening round)

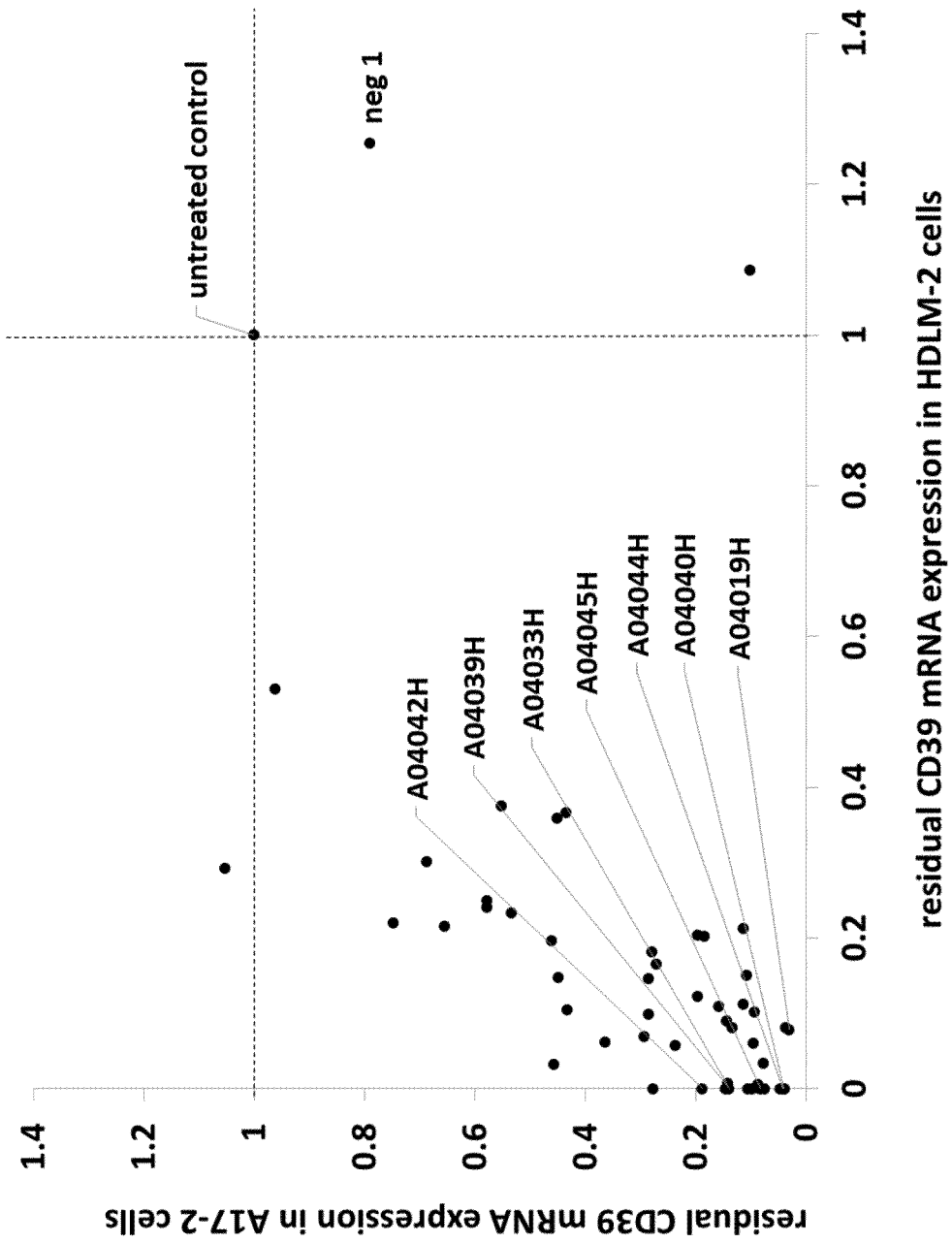
Fig. 3: Correlation analysis of hCD39 antisense oligonucleotides efficacy in A-172 cells compared to HDLM-2 cells

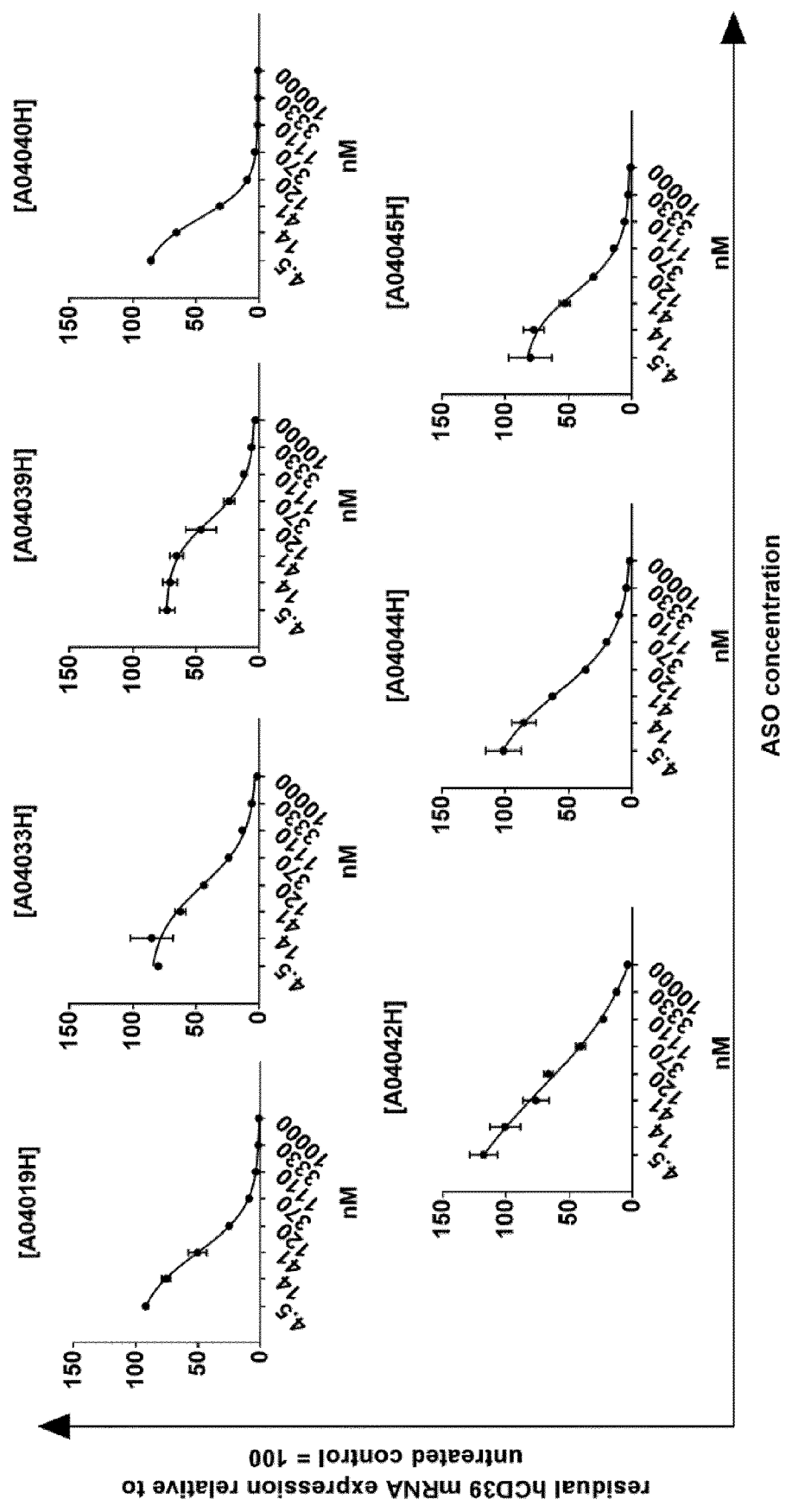
Fig. 4: Concentration-dependent hCD39 mRNA knockdown by selected hCD39 antisense oligonucleotides in HDLM-2 cells

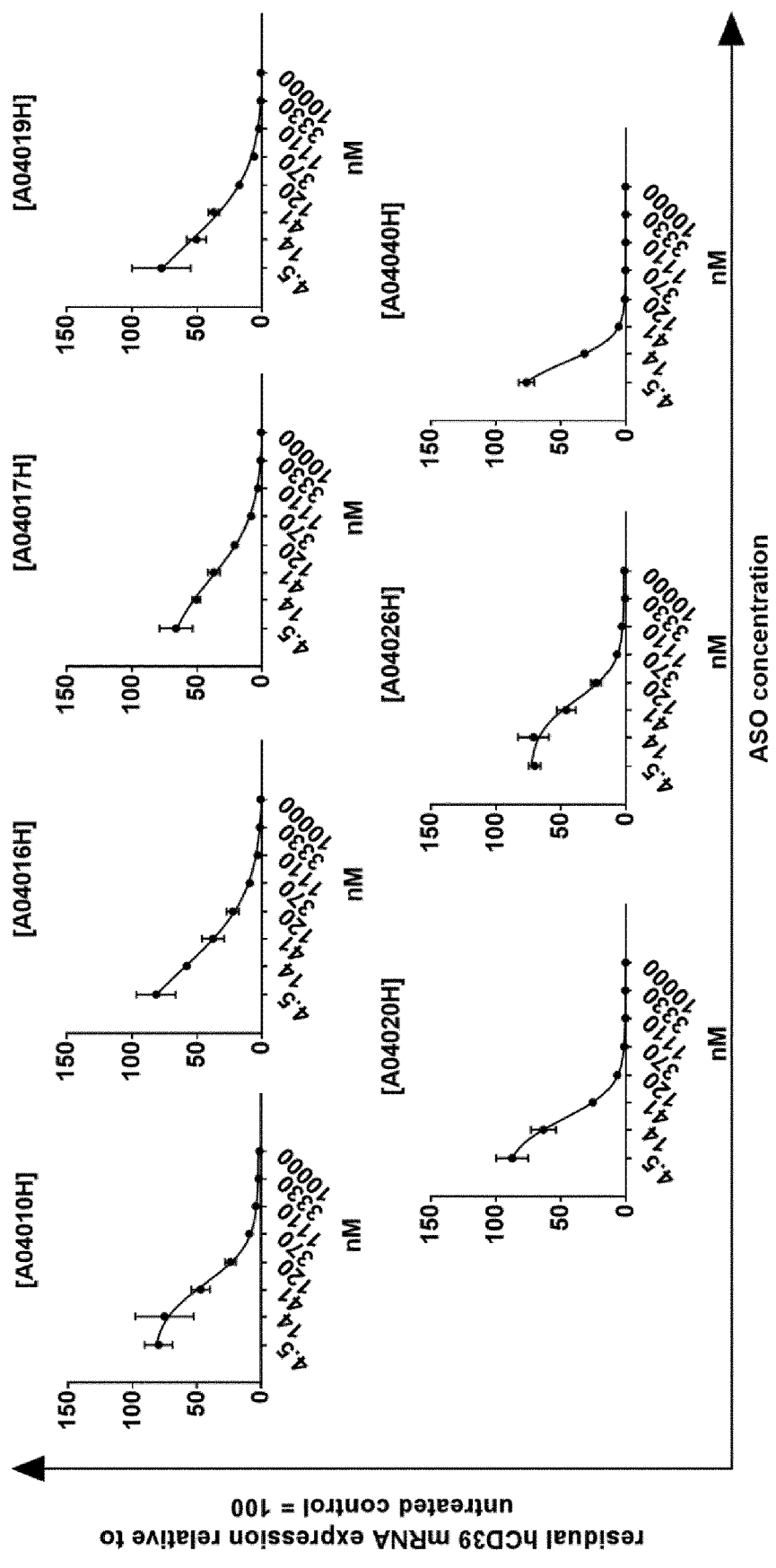
Fig. 5 Concentration-dependent hCD39 mRNA knockdown by further selected hCD39 antisense oligonucleotides in HDLM-2 cells Effects of hCD39 antisense oligonucleotides on hCD39 mRNA expression in HDLM-2 and A-172 cells (third screening round)

A-172 cells

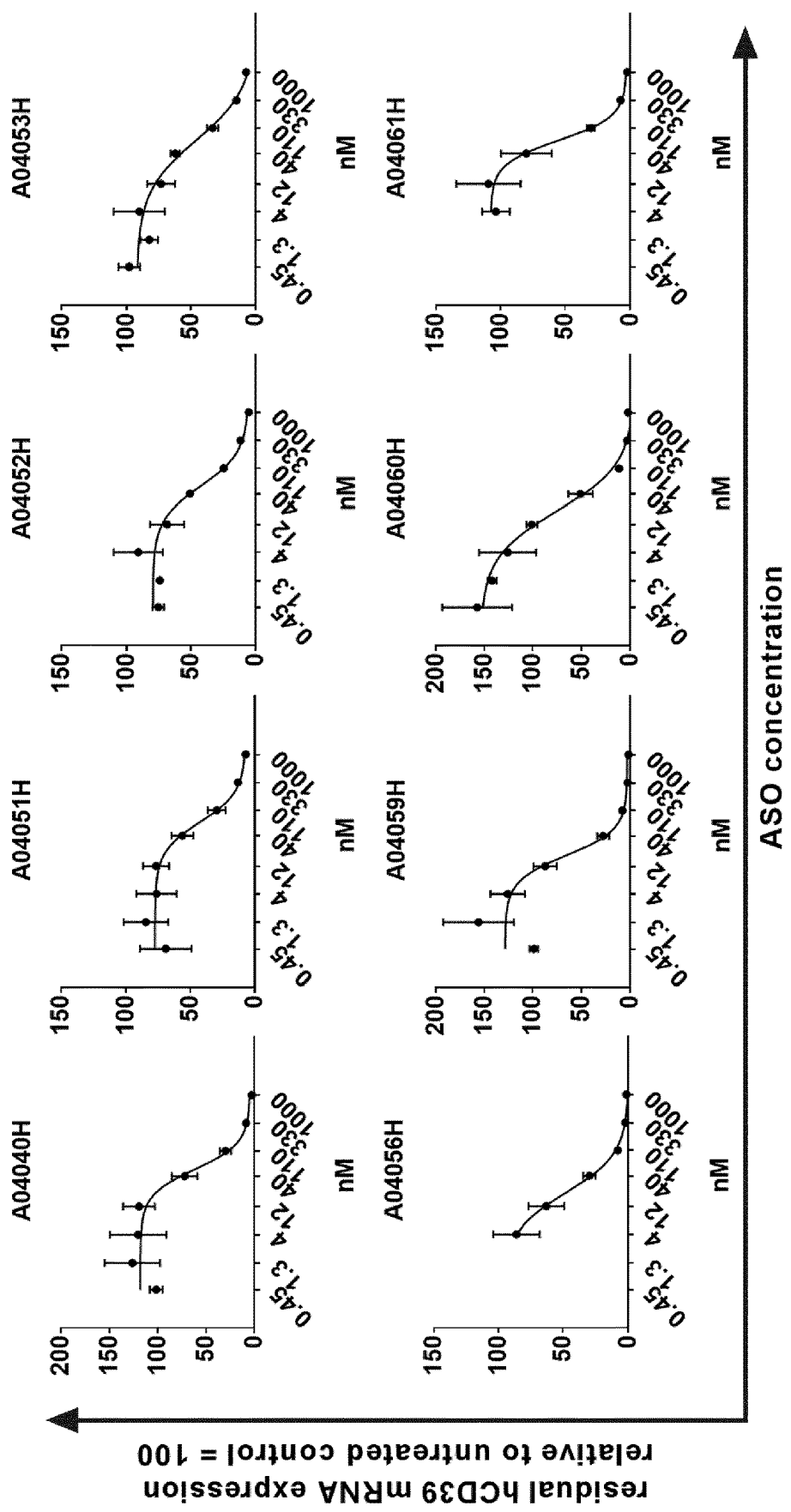
Fig. 7: Concentration-dependent hCD73 mRNA knockdown by selected hmCD73 antisense oligonucleotides of third screening round in EFO-21 cells

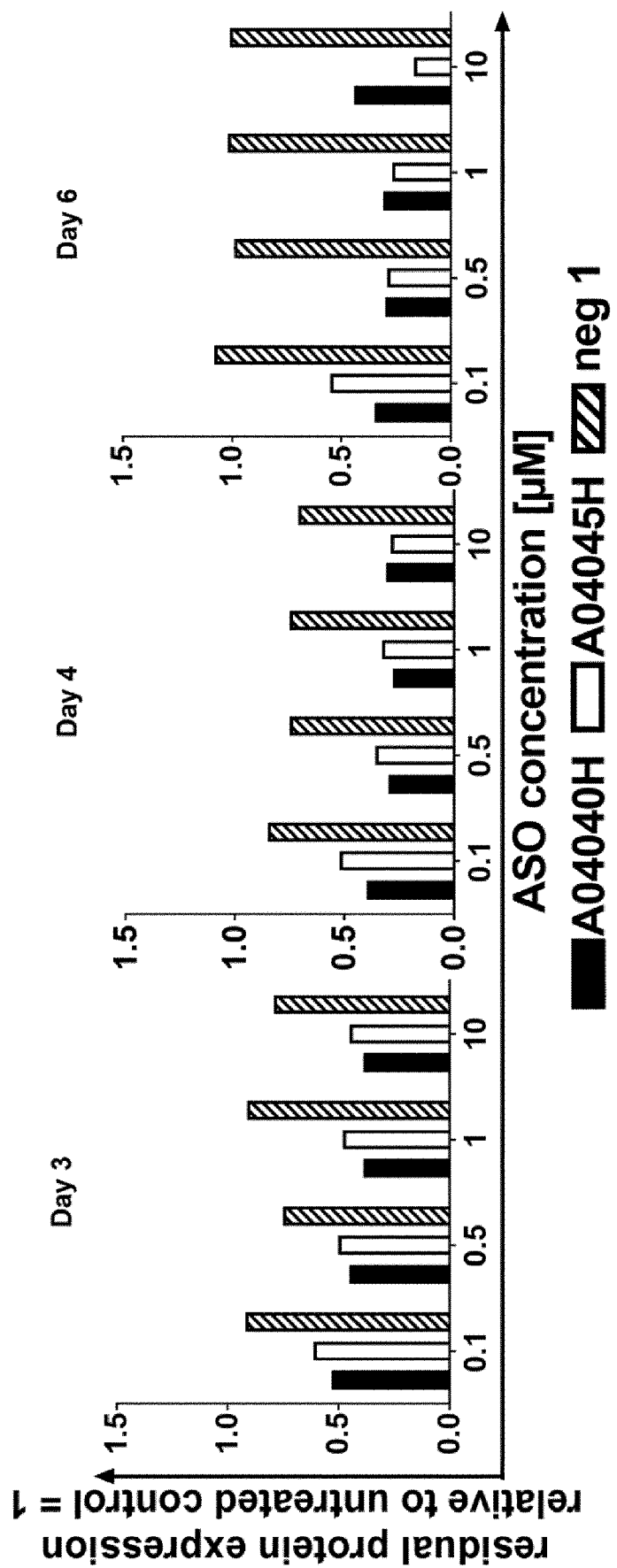
Fig. 8: Concentration- and time-dependent hCD39 protein knockdown by antisense oligonucleotides A04040H, A04045H and neg1

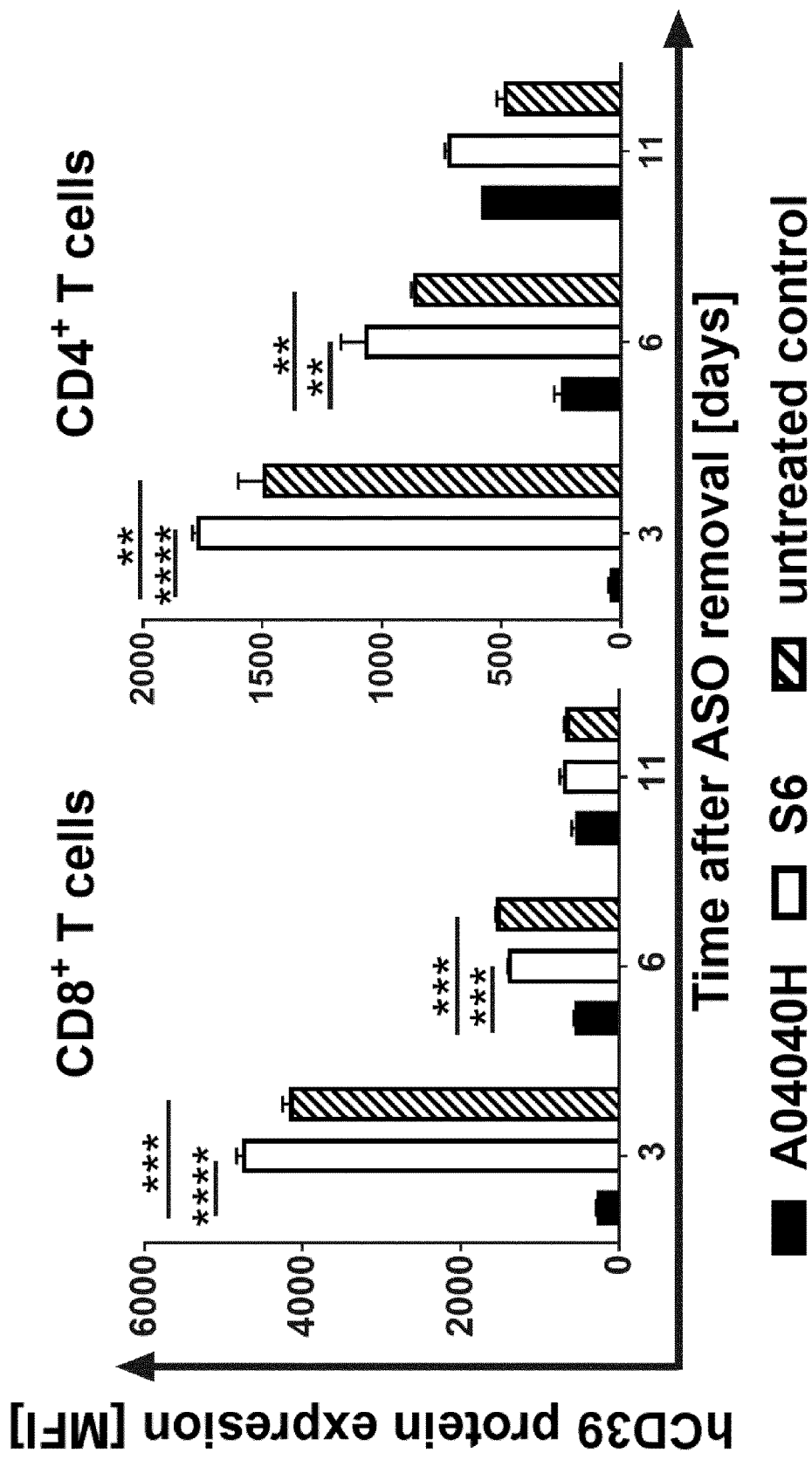
Fig. 9: Investigation of effects of hCD39-specific antisense oligonucleotides on hCD39 protein expression in primary human CD4+ and CD8+ T cells and investigation of persistence of effects after oligonucleotide removal

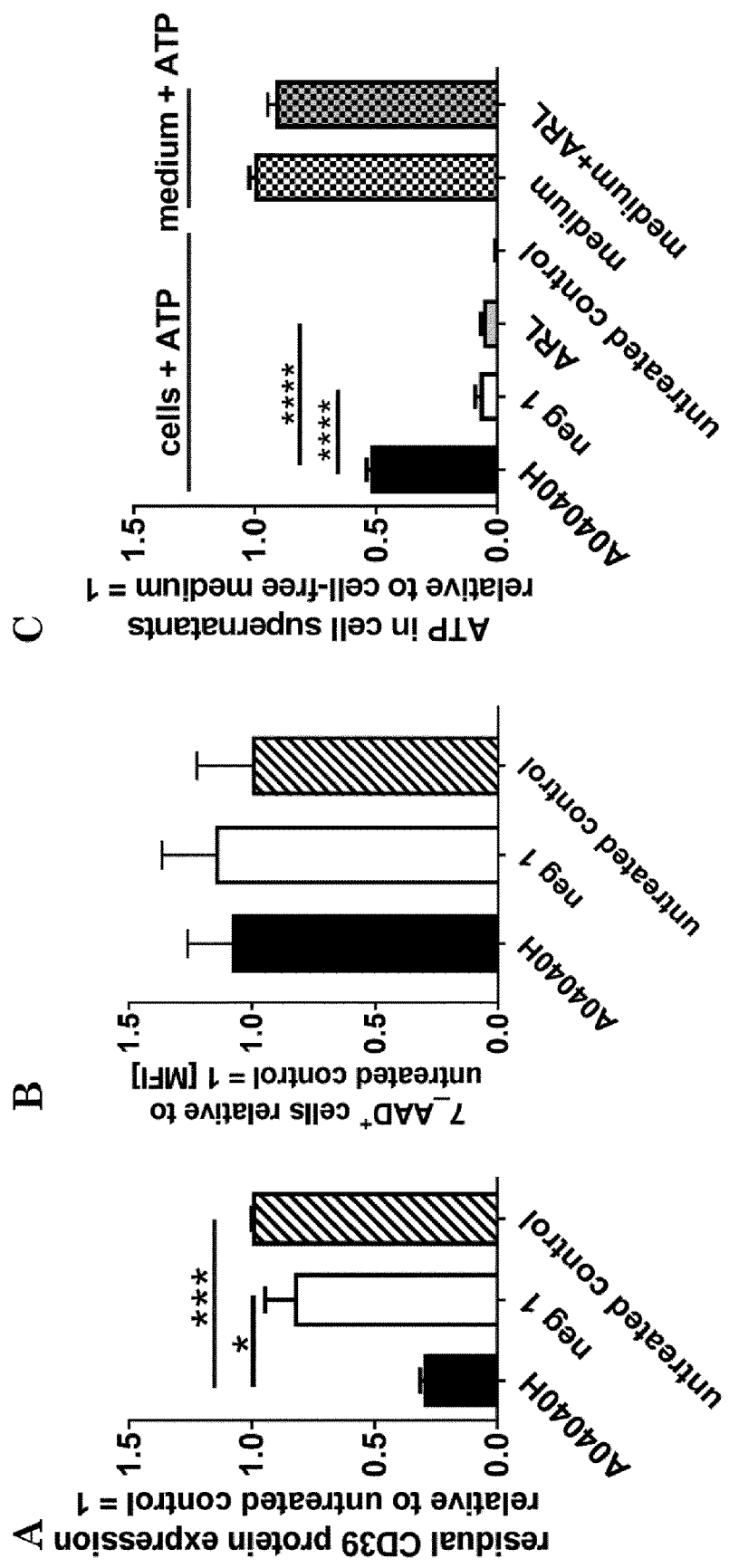
Fig. 10A, 10B and 10C: Effect of hCD39 knockdown (Fig. 10A) on viability (Fig. 10B) and ATP degradation capacity (Fig. 10C) in JIYOYE cells

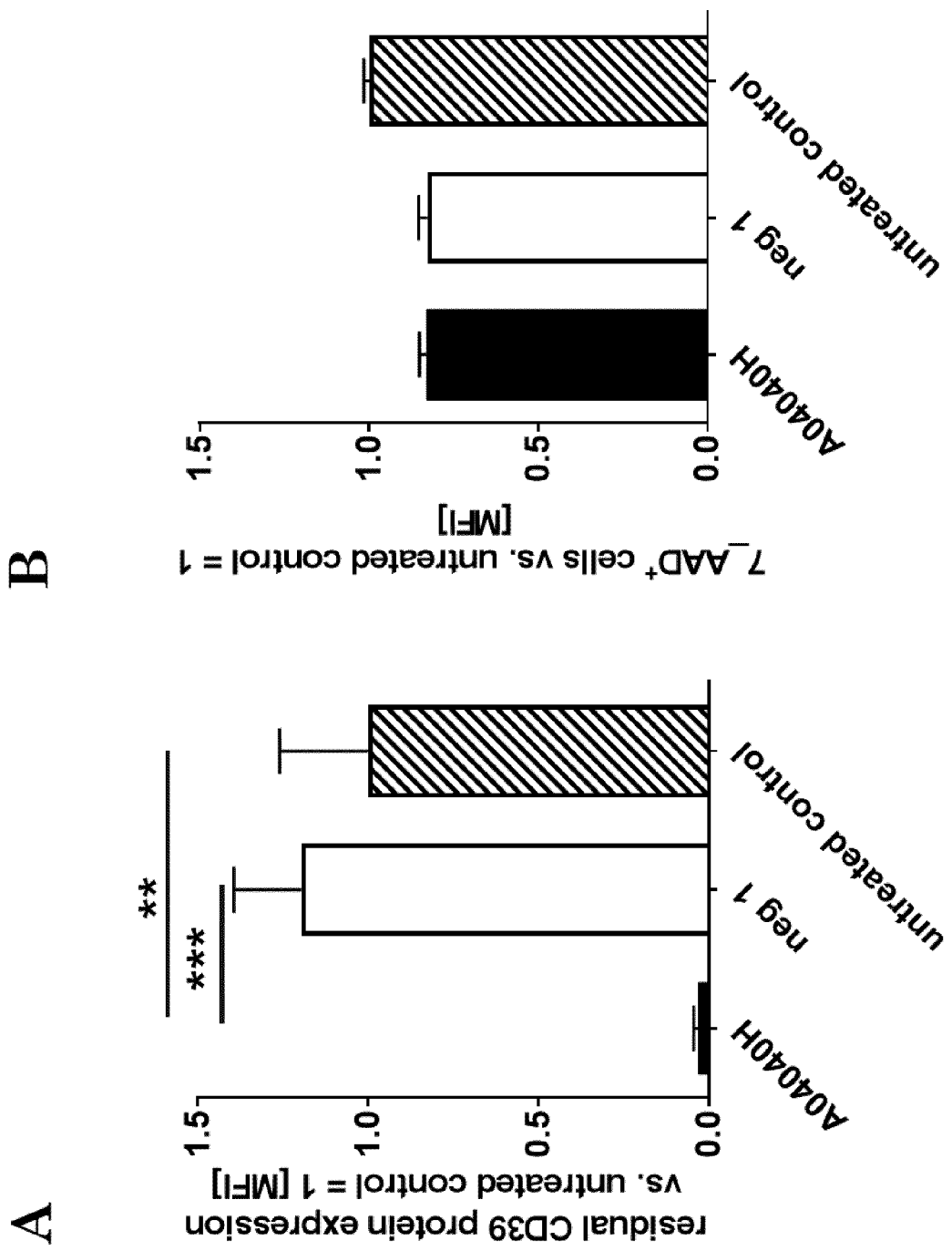
Fig. 11A and 11B: Effect of hCD39 knockdown (Fig. 11A) on viability (Fig. 11B) in primary human CD8+ T cells Fig. 11C and 11D: Effect of hCD39 knockdown on ATP degradation capacity (Fig. 11C-11D) in primary human CD8+ T cells
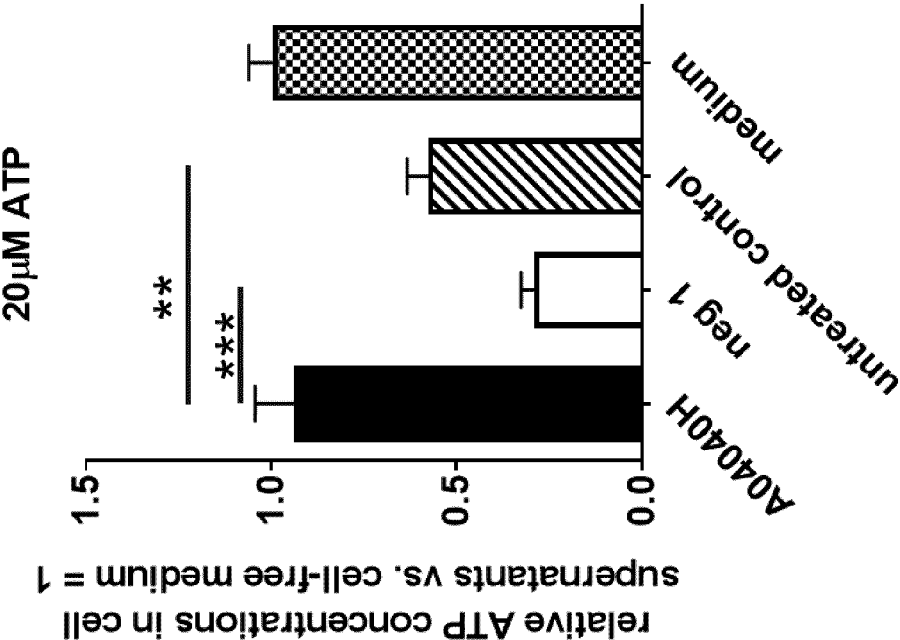
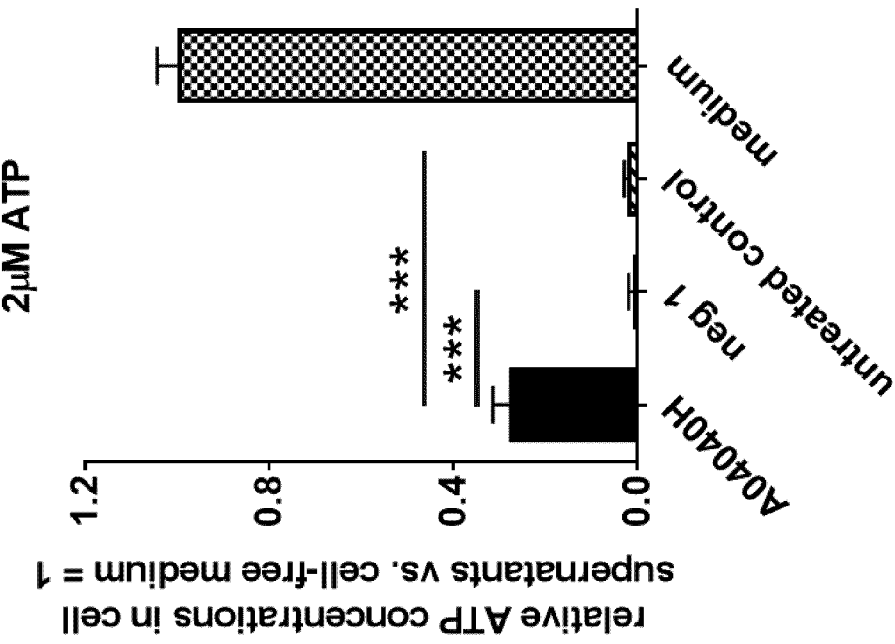

Effect of hCD39 antisense oligonucleotide treatment on CD39 protein expression, cell proliferation, and total CD8+ T cell numbers in the presence or absence of extracellular ATP in primary human CD8+ T cells

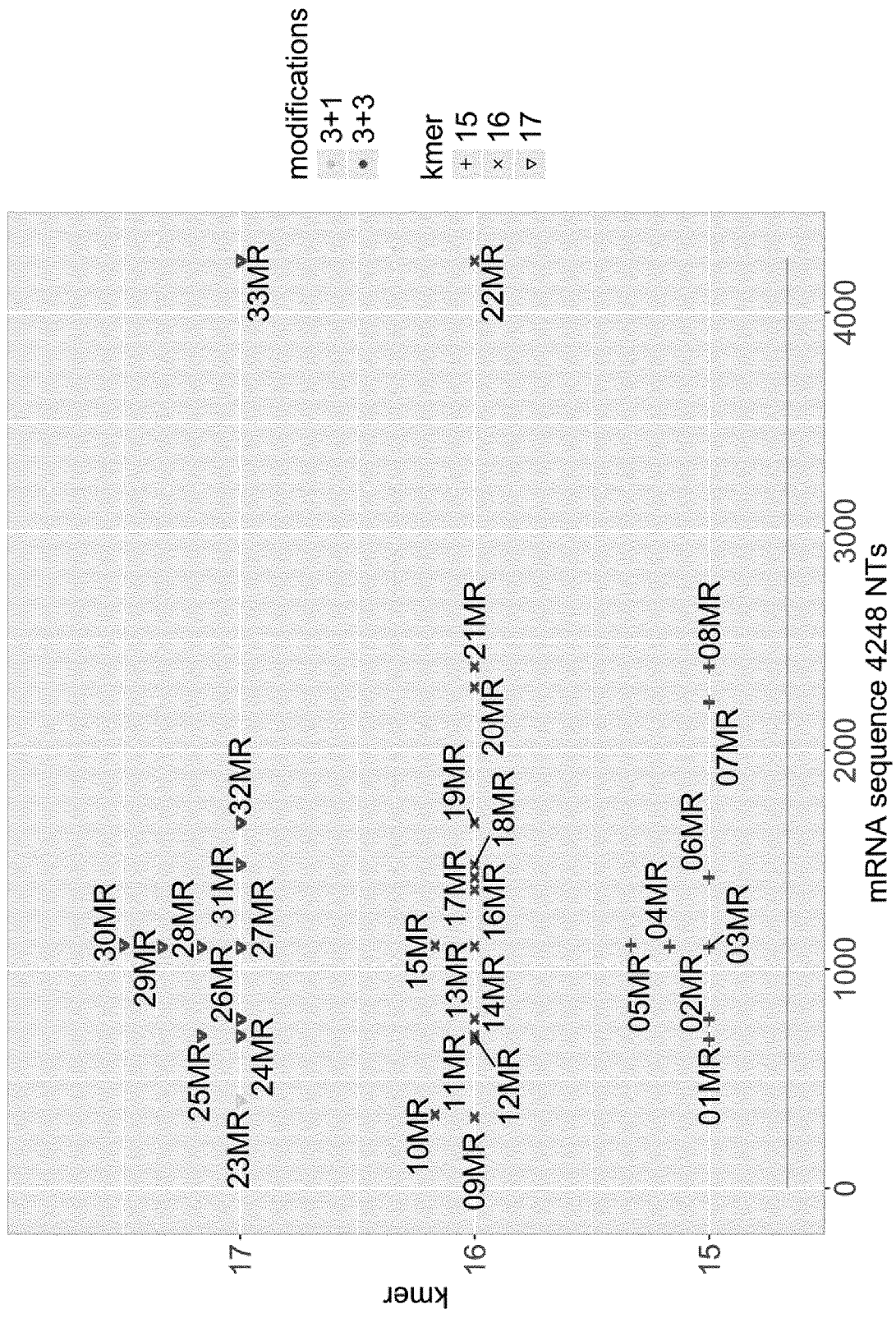
Fig. 13: Distribution of mCD39 antisense oligonucleotide binding sites on the mCD39 mRNA Knockdown efficacy of mCD39 antisense oligonucleotides in A20 murine cancer cell line

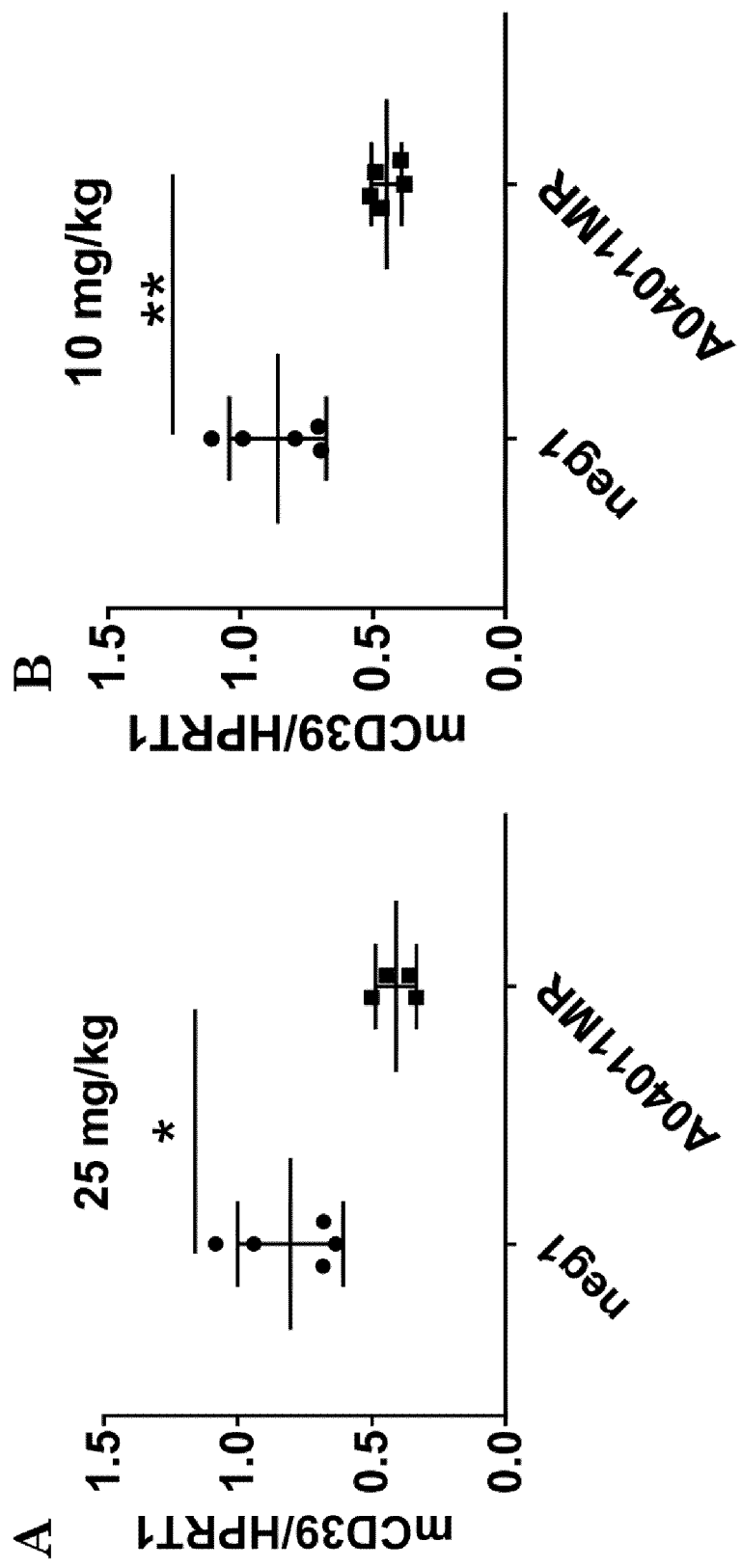
Fig. 15A and 15B: Antisense oligonucleotide-mediated in vivo mCD39 mRNA knockdown in spleens of C57BL/6 mice

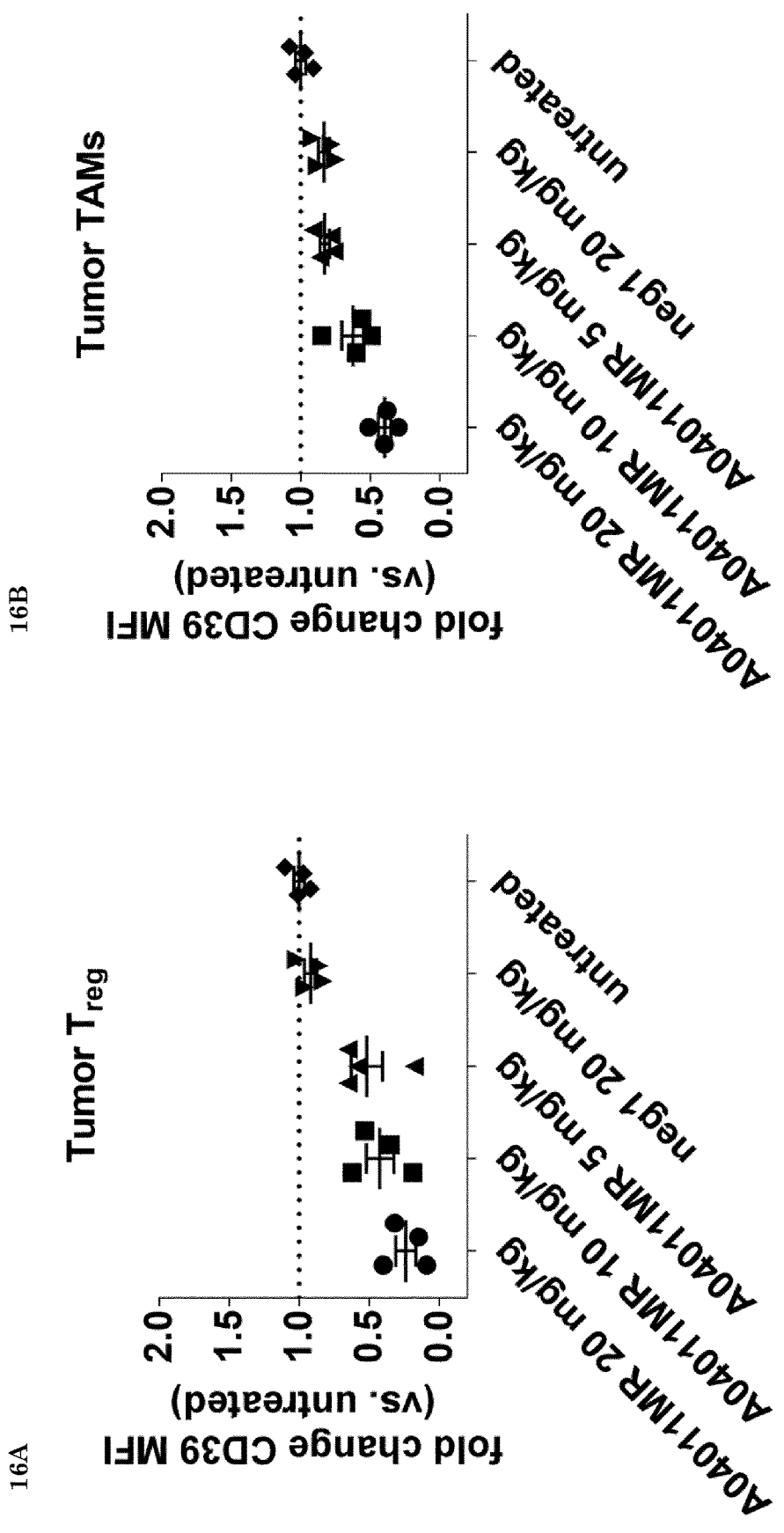
Figure 16: Antisense oligonucleotide-mediated in vivo mCD39 protein knockdown in a syngeneic mouse tumor model, suppressed mCD39 protein expression on T$_{regs}$ (Fig. 16A) and TAMs (Fig. 16B)

Fig. 17: hCD39 mRNA of SEQ ID No. 1 (NM_001776.5) (pos: 1-3420)

```
ORIGIN
    1 agggaagaag ggagaaagag agagagattt gaatatacat tgcttcaagg atgcaaaaaa
   61 ttacaacctg gaaaaggctt cgagtaactt taggaaaatg agctgctgga ctcctcagtc
  121 aatctgtcct ttctagtcaa tgaaaaagac agggtttgag gttccttccg aaacggggcc
  181 ggctaattta gcccctccca cgagcccaag ggtctgttat atctctgttt ccttgaggac
  241 ctctctcacg gagacggacc acagcaagca gaggctgggg gggggaaaga cgaggaaaga
  301 ggaggaaaac aaaagctgct acttatggaa gatacaaagg agtctaacgt gaagacattt
  361 tgctccaaga atatcctagc catccttggc ttctcctcta tcatagctgt gatagctttg
  421 cttgctgtgg ggttgaccca gaacaaagca ttgccagaaa acgttaagta tgggattgtg
  481 ctggatgcgg gttcttctca cacaagttta tacatctata gtggccagc agaaaaggag
  541 aatgacacag gcgtggtgca tcaagtagaa gaatgcaggg ttaaaggtcc tggaatctca
  601 aaatttgttc agaaagtaaa tgaaataggc atttacctga ctgattgcat ggaaagagct
  661 agggaagtga ttccaaggtc ccagcaccaa gagacacccg tttacctggg agccacggca
  721 ggcatgcggt tgctcaggat ggaaagtgaa gagttggcag acagggttct ggatgtggtg
  781 gagaggagcc tcagcaacta ccccttgac ttccagggtg ccaggatcat tactggccaa
  841 gaggaaggtg cctatgcctg gattactatc aactatctgc tgggcaaatt cagtcagaaa
  901 acaaggtggt tcagcatagt cccatatgaa accaataatc aggaaccttt ggagctttg
  961 gaccttgggg gagcctctac acaagtcact tttgtacccc aaaaccagac tatcgagtcc
 1021 ccagataatg ctctgcaatt tcgcctctat ggcaaggact acaatgtcta cacacatagc
 1081 ttcttgtgct atgggaagga tcaggcactc tggcagaaac tggccaagga cattcaggtt
 1141 gcaagtaatg aaattctcag ggacccatgc tttcatcctg atataagaa ggtagtgaac
 1201 gtaagtgacc tttacaagac cccctgcacc aagagatttg atgactct tccattccag
 1261 cagtttgaaa tccagggtat tggaaactat caacaatgcc atcaaagcat cctggagctc
 1321 ttcaacacca gttactgccc ttactcccag tgtgccttca tgggatttt cttgccacca
 1381 ctccaggggg attttgggc attttcagct ttttactttg tgatgaagtt tttaaacttg
 1441 acatcagaga aagtctctca ggaaaaggtg actgagatga tgaaaaagtt ctgtgctcag
 1501 ccttggggagg agataaaaac atcttacgct ggagtaaagg agaagtacct gagtgaatac
 1561 tgcttttctg gtacctacat tctctccctc cttctgcaag gctatcattt cacagctgat
 1621 tcctgggagc acatccattt cattggcaag atccagggca gcgacgccgg ctggactttg
 1681 ggctacatgc tgaacctgac caacatgatc ccagctgagc aaccattgtc cacacctctc
 1741 tcccactcca cctatgtctt cctcatggtt ctattctccc tggtcctttt cacagtggcc
 1801 atcataggct tgcttatctt tcacaagcct tcatatttct ggaaagatat ggtatagcaa
 1861 aagcagctga atatgctggg ctggagtgag gaaaaaaatc gtccagggag cattttcctc
 1921 catcgcagtg ttcaaggcca tccttccctg tctgccaggg ccagtcttga cgagtgtgaa
 1981 gcttccttgg cttttactga agccttttctt ttggaggtat tcaatatcct ttgcctcaag
 2041 gacttcggca gatactgtct ctttcatgag ttttttcccag ctacaccttt ctccttttgta
 2101 ctttgtgctt gtataggttt taaagacctg acacctttca taatctttgc tttataaaag
 2161 aacaatattg actttgtcta gaagaactga gagtcttgag tcctgtgata ggaggctgag
 2221 ctggctgaaa gaagaatctc aggaactggt tcagttgtac tcttttaagaa ccccttttctc
 2281 tctcctgttt gccatccatt aagaaagcca tatgatgcct ttggagaagg cagacacaca
 2341 ttccattccc agcctgctct gtgggtagga gaattttcta cagtaggcaa atatgtgcta
 2401 aagccaaaga gttttataag gaaatatatg tgctcatgca gtcaatacag ttctcaatcc
 2461 cacccaaagc aggtatgtca ataaatcaca tattcctagg tgatacccaa atgctacaga
 2521 gtggaacact cagacctgag atttgcaaaa agcagatgta aatatatgca ttcaaacatc
 2581 agggcttact atgaggtagg tgtatatac atgtcacaaa taaaaataca gttacaactc
 2641 agggtcacaa aaaatgcatc ttccaatgca tattttatt atggtaaaat atacataaat
 2701 ataattcacc attttaacat ttaattcata ttaaatacgt acaaatcagt gacatttagt
 2761 acattcacag tgttgtgcca ccatcaccac tatttagttc cagaacattt gcatcatcaa
 2821 tacattgtct agagacaaga ctatcctggg taggcagaaa ccatagatct tttgtgttta
 2881 cagctatgga aaccaactgt accataaaga tagttcactg agttttaaag ccaagccaca
 2941 tcttattttt ccaaggttta atttagtgag agggcagcat tagtgtggag tggcatgctt
 3001 ttgccctatc gtggaattta cacatcagaa tgtgcaggat ccaagtctga aagtgttgcc
 3061 acccgtcaca caacatgggc tttgtttgct tattccatga agcagcagct atagacctta
 3121 ccatggaaac atgaagagac cctgcacccc tttccttaag gattgctgca agagttacct
 3181 gttgagcagg attgactggt gatgtttcat tctgaccttg cccaagctc tccatctcta
 3241 gatctgggga ctgactgttg agctgatggg gaagaaaag ctctcacaca aaccggaagc
 3301 caaatgtccc ctatctcttg aatgatcaag tcacttttga caacatccag gtgaatataa
 3361 aaacttaata aagctgtgga aaggaactct taatcttctt ttctgctact taggttaaat
```

IMMUNOSUPPRESSION-REVERTING OLIGONUCLEOTIDES INHIBITING THE EXPRESSION OF CD39

The present disclosure refers to an immunosuppression-reverting oligonucleotide hybridizing with a nucleic acid sequence of an ectonucleoside triphosphate diphosphohydrolase-1 (ENTPD1 or CD39) and to a pharmaceutical composition comprising such immunosuppression-reverting oligonucleotide and a pharmaceutically acceptable carrier, excipient and/or dilutant.

TECHNICAL BACKGROUND

In recent years the treatment of several different diseases such as malignant tumors was very successful by application of immune therapy, in particular by inhibitors of so called "immune checkpoints". These checkpoints are molecules in the immune system that either turn up (co-stimulatory molecules) or down a signal. The concept of the therapeutic approach is based on the activation of endogenous anti-tumor immune reactions. Many cancers for example protect themselves from the immune system by inhibiting T cell and NK cell activity, respectively. Immune checkpoint modulators, i.e., stimulators or inhibitors are for example directed to one or more of CTLA-4, PD-1, PD-L1, LAG-3, VISTA, A2AR, BTLA, IDO, CD39, CD73, STAT3, TDO2, TIM-3, MICA, NKG2A, KIR, TIGIT, TGF-beta, Ox40, GITR, CD27, CD160, 2B4 and 4-1BB.

CD39 needs to be considered as one novel and promising candidate to improve immunity towards different types of cancers. CD39 is an ectonucleotidase (NTPdase) responsible for the conversion of ATP to ADP and ADP to AMP. It acts in concert with the ectonucleotidase CD73 which degrades AMP to immunosuppressive adenosine.

CD39 is widely expressed on different immune cells as monocytes, neutrophils, macrophages, B lymphocytes, Dendritic cells (DCs), some subsets of natural killer cells (NK), and T cells. Mainly T reg cells are prominent to express CD39 and CD73 enabling them to generate adenosine in order to suppress T cell responses. In addition, enhanced CD39 expression levels have been found in many different tumors (solid as well as hematologic tumors) and on tumor associated immune cells. E.g. in melanoma, increased CD39 expression has been investigated on melanocytes and was found to be associated with their differentiation into malignant cells. Furthermore, enhanced CD39 mRNA and protein levels were investigated on cancer cells from kidney, lung, testicular, thyroid tumors as well as in lymphoma. These increased expression levels of CD39 in different tumors strongly suggests an important role for this ectonucleotidase in tumor promotion, growth and mediation of an immunosuppressive microenvironment.

Dying cancer cells release ATP to the extracellular space in the tumor microenvironment. Living tumor cells can profit from ATP due to the generation of immunosuppressive adenosine. By this, tumor cells are competent to perform uncontrolled proliferation and expansion. As mentioned above, different tumor cells or tumor associated immune cells show potent CD39 and CD73 expression, resulting in increased adenosine levels in the tumor microenvironment. By binding to $A_{2A}$ or $A_{2B}$ receptors on lymphocytes, adenosine mediates an immunosuppressive signal towards these cells. For example, T cells are inhibited in their proliferation, cytotoxic cytokine production and activation. NK cells show reduced cytotoxic potential. Adenosine induces alternative activation in macrophages (immune suppressive M2 phenotype) resulting in reduced pro-inflammatory cytokine production but increased generation of the immunosuppressive cytokine IL-10. The important role of CD39 as relevant therapeutic target in different tumors is underlined by the fact that tumor models using CD39 and CD73 knockout mice show improved disease outcome.

However, it is very likely that the inhibition of CD39 is more efficient than the inhibition of CD73 alone in order to enhance anti-tumor immune responses. On one hand because the blockade of CD39 would lead to reduced adenosine levels within the tumor microenvironment. On the other hand, high ATP levels in the tumor microenvironment can act as "find me" signal for DCs, macrophages and their precursors mediating an immune stimulatory signal.

ATP binds to $P2X_7$ receptors on DCs and activates them to release pro-inflammatory cytokines as IL-β or IL-28. These cytokines in turn activate NK cells, T cells and macrophages and enhance their proliferation, cytotoxicity and maturation. Accordingly, engagement of the T cell receptor (TCR) results in ATP release during T cell activation. This ATP can act in an autocrine manner via P2X receptors to enhance TCR triggered activation and IL-2 production. The same ATP might act in a paracrine fashion on neighboring lymphocytes via P2X receptors to inhibit their motility in the lymph nodes, thereby enhancing interactions between T cells and APCs. Taken together, increasing ATP levels in the tumor microenvironment sets perfect conditions to initiate an optimal anti-tumor immune response.

In order to block CD39 ectonucleotidase activity, anti-human CD39 monoclonal antibodies such as IPH52 (Bastid et al, CancerImmunology Research, 2014) and OREG-103/BY40 (Bennefoy et al., OncoImmunology 4:5, 2015) are currently under pre-clinical investigation which led to prolonged life expectation in animal models. However, these monoclonal antibodies might fail to localize to the tumor microenvironment due to steric hindrance. Furthermore, small molecular inhibitors of CD39 such as ARL67156 (OncoImmunology 1:3; 2012) and POM-1 (Gastroenterology; 2010; 139(3): 1030-1040) have been tested in vitro and in vivo in animal models leading to reduced tumor growth. However, these small molecules have to be administered in high doses and high frequency due to their low activity and short half-life in vivo.

Immune therapies have resulted in long-term remission, but only of small patient groups so far. The reason may be that numerous immune checkpoints and optionally further immunosuppressive mechanisms are involved in the interaction between for example the immune system and the tumor cells. The combination of immune checkpoints and potential other mechanisms may vary depending on the tumor and individual conditions of a subject to escape the body's defenses.

For the inhibition of several immunosuppressive mechanisms common approaches using an antibody and/or a small molecule are not or hardly suitable as the molecular target is located intracellularly or does not have enzymatic activity. Accordingly, an agent which is safe and effective in inhibiting the function of an "immune checkpoint" such as CD39 would be an important addition for the treatment of patients suffering from diseases or conditions affected for example by the activity of this enzyme.

Oligonucleotides of the present invention are very successful in the inhibition of the expression and activity of CD39, respectively. The mode of action of an oligonucleotide differs from the mode of action of an antibody or small molecule, and oligonucleotides are highly advantageous regarding for example (i) the penetration of tumor tissue in solid tumors,
(ii) the blocking of multiple functions and activities, respectively, of a target,
(iii) the combination of oligonucleotides with each other or an antibody or a small molecule, and
(iv) the inhibition of intracellular effects which are not accessible for an antibody or inhibitable via a small molecule.

Therefore, targeting CD39 expression on cancer and immune cells on mRNA-level by antisense-oligonucleotides is a promising state-of-the-art approach to develop and improve for example immunotherapies against different cancers and immune diseases, respectively.

SUMMARY

The present invention refers to an oligonucleotide such as an immunosuppression-reverting oligonucleotide comprising about 10 to 20 nucleotides, wherein at least one of the nucleotides is modified. The oligonucleotide hybridizes for example with a nucleic acid sequence of ectonucleosidase CD39 of SEQ ID NO. 1 (human) and/or a sequence of SEQ ID NO.2 (mouse/rat). The modified nucleotide is for example selected from the group consisting of a bridged nucleic acid (e.g., LNA, cET, ENA, 2'Fluoro modified nucleotide or 2'O-Methyl modified nucleotide, and combinations thereof). In some embodiments, the oligonucleotide inhibits at least 50% of the CD39 expression and in some embodiments the oligonucleotide inhibits the expression of CD39 at a nanomolar concentration.

Antisense oligonucleotides have significant advantages in comparison to RNAi. Antisense oligonucleotides can be transfected without transfecting reagent in vitro and thus, the transfection is closer to in vivo conditions than transfections using transfecting reagents which are obligatory for the transfection of RNAi. In vivo systemic administration of antisense oligonucleotides is possible in different tissues whereas the administration of RNAi in vivo is dependent on delivery systems such as GalNAc for example in liver. Moreover, antisense oligonucleotides are shorter than RNAi and therefore, are less complex in synthesis and in the uptake into cells. RNAi regularly show off-target effects of passenger strands which likewise can initiate RNAi. passenger strand RISC loading is a significant concern for RNAi drugs because the passenger strand could direct RNAi activity towards unintended targets, resulting in toxic side effects." (see Chackalamannil, Rotella, Ward, Comprehensive Modicinal Chemistry III Elsevier, Mar. 6, 2017). Antisense oligonucleotides do not comprise a passenger strand.

The present invention is further directed to a pharmaceutical composition comprising an immunosuppression-reverting oligonucleotide of the present invention and optionally a pharmaceutically acceptable carrier, excipient and/or dilutant. In some embodiments, this pharmaceutical composition additionally comprises a chemotherapeutic such as platinum or gemcitabine, another oligonucleotide, an antibody or a fragment thereof such as a Fab fragment, a HERA fusion protein, a ligand trap, a nanobody, a BiTe and/or a small molecule which is for example effective in tumor treatment, and combinations thereof.

In some embodiments, the oligonucleotide of the present invention is in combination with another oligonucleotide, an antibody and/or a small molecule, either each of these compounds is separate or combined in a pharmaceutical composition, wherein the oligonucleotide, the antibody or a fragment thereof such as a Fab fragment, a HERA fusion protein, a ligand trap, a nanobody, a BiTe and/or the small molecule inhibits or stimulates an immune suppressive factor such as IDO1, IDO2, CTLA-4, PD-1, PD-L1, LAG-3, VISTA, A2AR, CD39, CD73, STAT3, TDO2, TIM-3, TIGIT, TGF-beta, BTLA, MICA, NKG2A, KIR, CD160, Chop, and/or Xbp1. In addition or alternatively, the oligonucleotide, the antibody and/or the small molecule inhibits or stimulates or an immune stimulatory factor such as 4-1BB, Ox40, KIR, GITR, CD27 and/or 2B4.

Furthermore, the present invention relates to the use of the oligonucleotide or the pharmaceutical composition of the present invention in a method of preventing and/or treating a disorder, where a CD39 imbalance is involved. In some embodiments, the disorder is for example an autoimmune disorder, for example autoimmune arthritis or gastrointestinal autoimmune diseases such as inflammatory bowel disease (IBD) or colitis, an immune disorder, for example an immune exhaustion due to chronic viral infections such as HIV infection, a cardiovascular disorder, an inflammatory disorder, for example a chronic airway inflammation, a bacterial, viral and/or fungal infection, for example sepsis or a *Mycobacterium bovis* infection, a liver disorder, a chronic kidney disorder, a psychiatric disorder and/or cancer. In some embodiments, the oligonucleotide or the pharmaceutical composition of the present invention is for example administered locally or systemically.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

DESCRIPTION OF FIGURES

FIG. 3 shows a correlation analysis of the efficacy of antisense oligonucleotides in HDLM-2 and A-172 cells.

FIG. 4 shows concentration-dependent hCD39 mRNA knockdown by selected hCD39 antisense oligonucleotides in HDLM-2 cells which were A04019H (SEQ ID No. 23), A04033H (SEQ ID No. 37), A04039H (SEQ ID No. 43), A04040H (SEQ ID No. 3), A04042H (SEQ ID No. 45), A04044H (SEQ ID No. 47) and A04045H (SEQ ID No. 4). HDLM-2 cells were treated for 3 days with the indicated concentration of the respective antisense oligonucleotide. Residual hCD39 expression is depicted compared to untreated control cells. hCD39 mRNA expression values were normalized to expression of the housekeeping gene HPRT1. Concentration-dependent target knockdown was used for calculation of $IC_{50}$ values shown in Table 8.

FIG. 5 shows concentration-dependent hCD39 mRNA knockdown by further selected hCD39 antisense oligonucleotides in HDLM-2 cells which were A04010H (SEQ ID No. 14), A04016H (SEQ ID No. 20), A04017H (SEQ ID No. 21), A04019H (SEQ ID No. 23), A04020H (SEQ ID No. 24) and A04026H (SEQ ID No. 30). The antisense oligonucleotide A04040H (SEQ ID No. 3) that had shown potent activity in the first and second screening round was used as reference. HDLM-2 cells treated for 3 days with the indicated concentrations of the respective antisense oligonucleotide. hCD39 mRNA expression values were normalized to expression of the housekeeping gene HPRT1. Residual hCD39 mRNA expression relative to untreated cells (set as 100) is depicted. Depicted is the mean of triplicate wells+/−SD. Concentration-dependent target knockdown was used for calculation of $IC_{50}$ values shown in Table 9.

FIG. 7 shows concentration-dependent hCD39 mRNA knockdown by further selected hCD39 antisense oligonucleotides in a third screening round in HDLM-2 and A-172 cells which were A04051H (SEQ ID No. 88), A04052H (SEQ ID No. 89), A04053H (SEQ ID No. 89), A04056H (SEQ ID No. 92), A04059H (SEQ ID No. 94), A04060H (SEQ ID No. 95) and A04061H (SEQ ID No. 96). The antisense oligonucleotide A04040H (SEQ ID No. 3) that had shown potent activity in the first and second screening round was used as reference. HDLM-2 cells treated for 3 days with the indicated concentrations of the respective antisense oligonucleotide. hCD39 mRNA expression values were normalized to expression of the housekeeping gene HPRT1. Residual hCD39 mRNA expression relative to untreated cells (set as 100) is depicted. Depicted is the mean of triplicate wells+/−SD. Concentration-dependent target knockdown was used for calculation of $IC_{50}$ values shown in Table 12.

FIG. 8 depicts concentration- and time-dependent CD39 protein knockdown by A04040H (SEQ ID No. 3) and A04045H (SEQ ID No. 4). Analysis of CD39 protein expression by flow cytometry in HDML-2 cells is given after treatment with the indicated antisense oligonucleotides for 3, 4 and 6 days. As treatment control, cells were treated with neg1 for 3, 4 and 6 days at the indicated concentrations. Relative expression compared to untreated control cells (=1) is depicted.

FIG. 9 shows primary human $CD8^+$ and $CD4^{30}$ T cells which were treated for 6 days with 10 μM of the hCD39 specific ASO A04040H (black column) or the control oligonucleotide S6 (white column) in the presence of anti-CD3 antibody. Control cells were activated with anti-CD3 but did not receive any oligonucleotide treatment (striped column). Thereafter, oligonucleotides and anti-CD3 were removed and hCD39 protein expression was analyzed by flow cytometry three, six, and eleven days after oligonucleotide removal. CD39 protein expression is depicted as mean fluorescence intensity (MFI) and was calculated by subtracting the MFI of the unspecific isotype control from the MFI of CD39. Depicted is the mean of duplicate wells+/−SD.

FIG. 10A-10C depict effects of hCD39 knockdown on viability and ATP concentration in JIYOYE cells. JIYOYE cells were treated with the indicated antisense oligonucleotide A04040H (SEQ ID No.3) or neg1 for 6 days in total at 5 μM. Medium was replaced with fresh oligonucleotide-containing medium after 3 days and hCD39 protein knockdown efficacy was analyzed on day 6 by flow cytometry. Residual hCD39 expression and viability of oligonucleotide-treated cells is depicted compared to untreated cells (FIG. 10A-10B). After 6 days, 20 μM of the CD39 small molecular inhibitor ARL67156 trisodium salt was added to no ASO treated cells and incubated for 1 h at 37° C. Then, 2 μM of ATP was added to cells or cell culture medium without cells from each condition and ATP concentration of cell supernatants or cell culture medium was determined after 30 min using the ATP Bioluminescence Assay Kit (Roche) (FIG. 10C).

FIG. 11A-11D show knockdown of hCD39 protein (FIG. 11A) and viability (FIG. 11B) of primary human $CD8^+$ T cells, isolated from peripheral blood using MACS. $CD8^+$ T cells were activated by plate-bound anti-human CD3 (OKT-3). Activated cells were treated with RPMI-1640 medium, medium supplemented with A04040H (SEQ ID No. 3), and medium supplemented with neg1 at 5 μM, respectively, for 6 days in total. After 3 days, medium was replaced with fresh medium containing 5 μM of A04040H (SEQ ID No. 3) and neg 1, respectively, and hCD39 protein knockdown efficacy (FIG. 11A) and viability (FIG. 11B) were analyzed on day 6 by flow cytometry. Residual hCD39 expression and viability (median of 7-AAD positive cells) is depicted compared to untreated cells (FIG. 11A-11B). The same day, cells were harvested, washed and re-plated at a constant cell number (150.000 cells/Well in a 96-Well plate) in triplicates. Then, 2 μM (FIG. 11C) or 20 μM (FIG. 11D) of ATP was added to cells or cell culture medium without cells and ATP concentration of cell supernatants or cell culture medium was determined after 30 min using the ATP Bioluminescence Assay Kit (Roche).

FIG. 13 depicts the distribution of mCD39 antisense oligonucleotide binding sites on the mCD39 mRNA of SEQ ID No. 2 (NM_001304721.1) as well as their modification(s) and length. mCD39 antisense oligonucleotide sequences were aligned to the mCD39 mRNA sequence. The different grayscales indicate the different LNA modifications and symbols indicate the different length of the antisense oligonucleotides.

FIG. 14-1 and 14-2 show mCD39 mRNA knockdown efficacy of mCD39 antisense oligonucleotides in the murine cancer cell line A20 (mouse B cell lymphoma). A20 cells were treated with a single dose of 10 µM of the respective antisense oligonucleotide. As negative control, cells were treated with neg1, an antisense oligonucleotide having the sequence CGTTTAGGCTATGTACTT (SEQ ID NO:99). Residual mCD39 mRNA expression relative to untreated cells is depicted. Expression values were normalized to expression of the housekeeping gene HPRT1.

FIGS. 15A and 15B depict CD39 mRNA expression levels in spleens from C57BL/6 mice treated by subcutaneous injections of either A04011MR or the negative control oligonucleotide neg1 at doses of 25 mg/kg or 10 mg/kg on days 1, 2, 3, 4, 5, 9, 12, 16, and 19 (5 mice/group). Expression values were normalized to expression values of the housekeeping gene HPRT1.

FIGS. 16A and 16B show CD39 protein expression on tumor infiltrating regulatory T cells ($T_{regs}$) (FIG. 16A) and tumor associated macrophages (TAMs) (FIG. 16B) from oligonucleotide-treated mice in relation to tumors of untreated mice.

FIG. 17 shows hCD39 mRNA of SEQ ID No. 1 (NM_001776.5) (pos: 1-3420).

DETAILED DESCRIPTION

Figures 1, 2A:
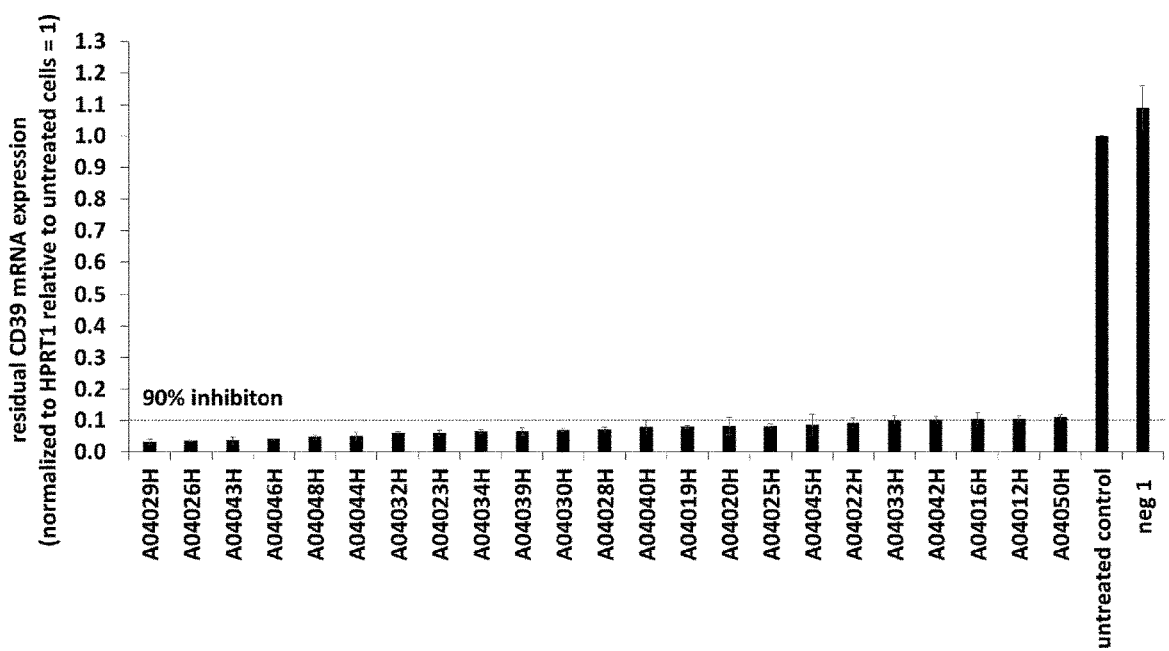
FIG. 1 depicts the distribution of hCD39 antisense oligonucleotide binding sites on the hCD39 mRNA of SEQ ID No. 1 (NM_001776.5) as well as their modification(s) and length. hCD39 antisense oligonucleotides were aligned to the hCD39 mRNA sequence of SEQ ID No. 1. The different grayscales indicate the different LNA modifications and symbols indicate the different length of the antisense oligonucleotides.
FIGS. 2A to 2D depict hCD39 mRNA knockdown efficacy of hCD39 antisense oligonucleotides in human cancer cell lines HDLM-2 (human Hodgkin Lymphoma) in a first and second screening round (FIGS. 2A-1 and 2A-2) and 2B-1 and 2B-2 and A-172 (human glioblastoma) in a first and second screening round (FIGS. 2C-1 and 2C-2) and 2D-1 and 2D-2. HDLM-2 and A-172 cells were treated for 3 days with 10 µM of the respective antisense oligonucleotide. As negative control, cells were treated with neg1, an antisense oligonucleotide having the sequence CGTTTAGGCTATGTACTT (SEQ ID NO:99) (described in WO2014154843 A1). Residual hCD39 mRNA expression relative to untreated cells is depicted. Expression values were normalized to expression of the housekeeping gene HPRT1. Depicted is the mean of triplicate wells+/−SD.
Figures 2, 2A:
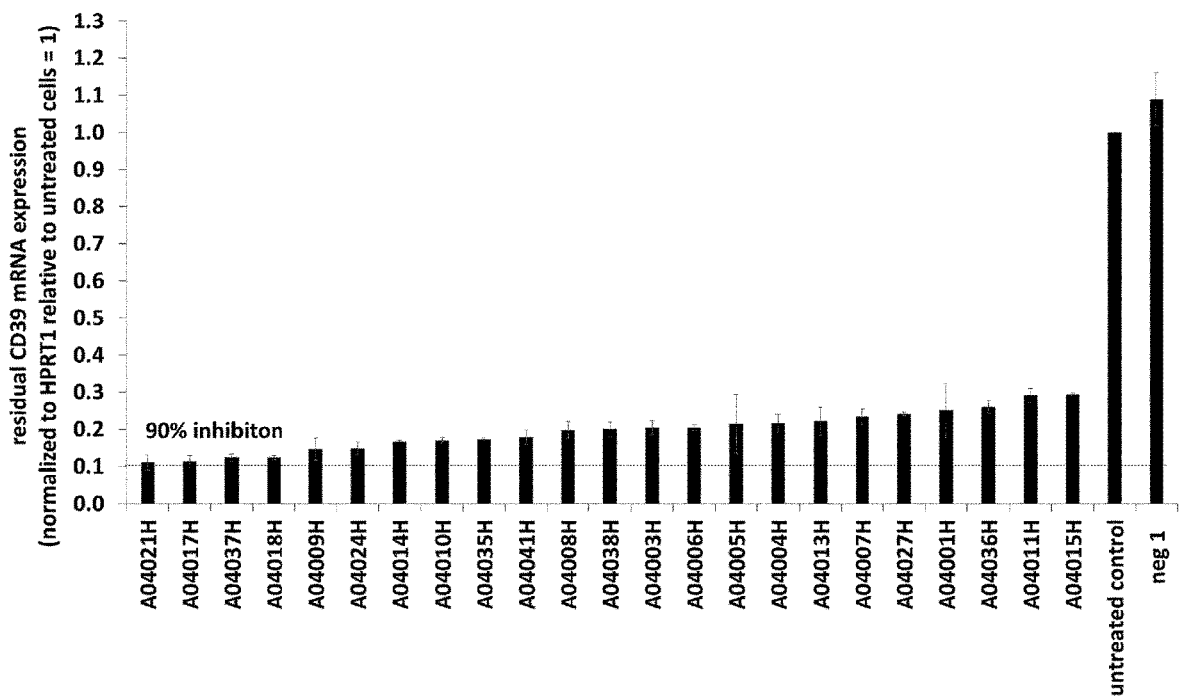
Figures 1, 2B:
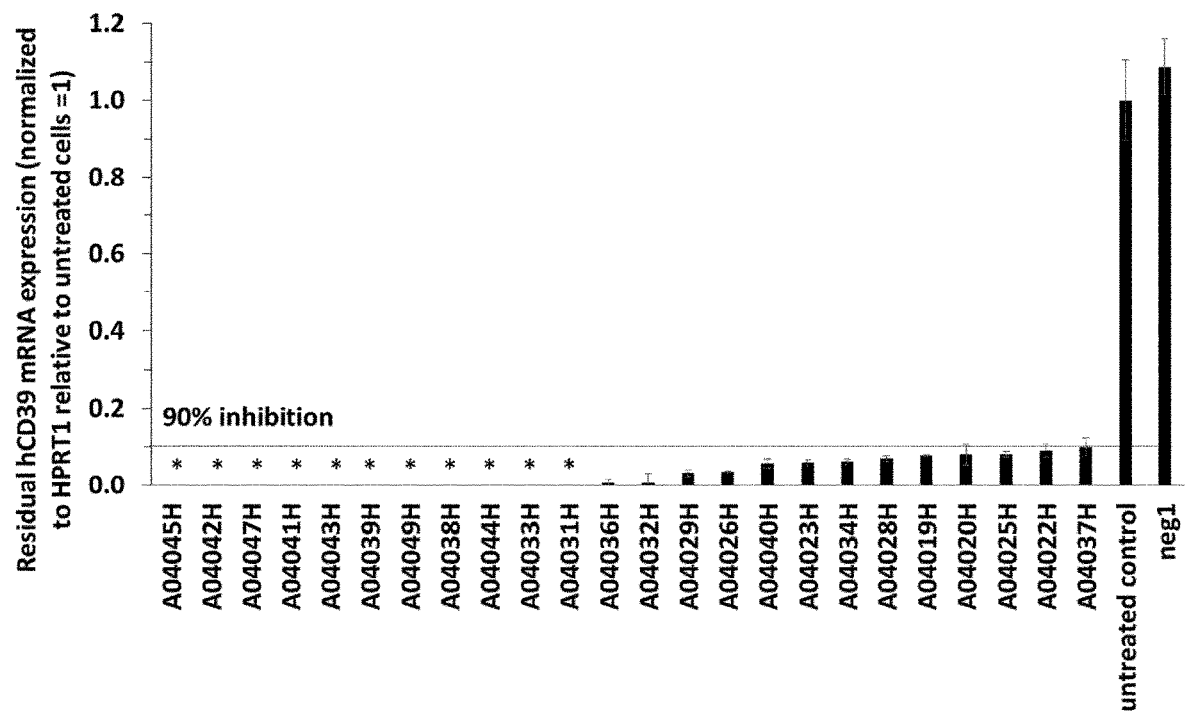
Figures 2, 2B:
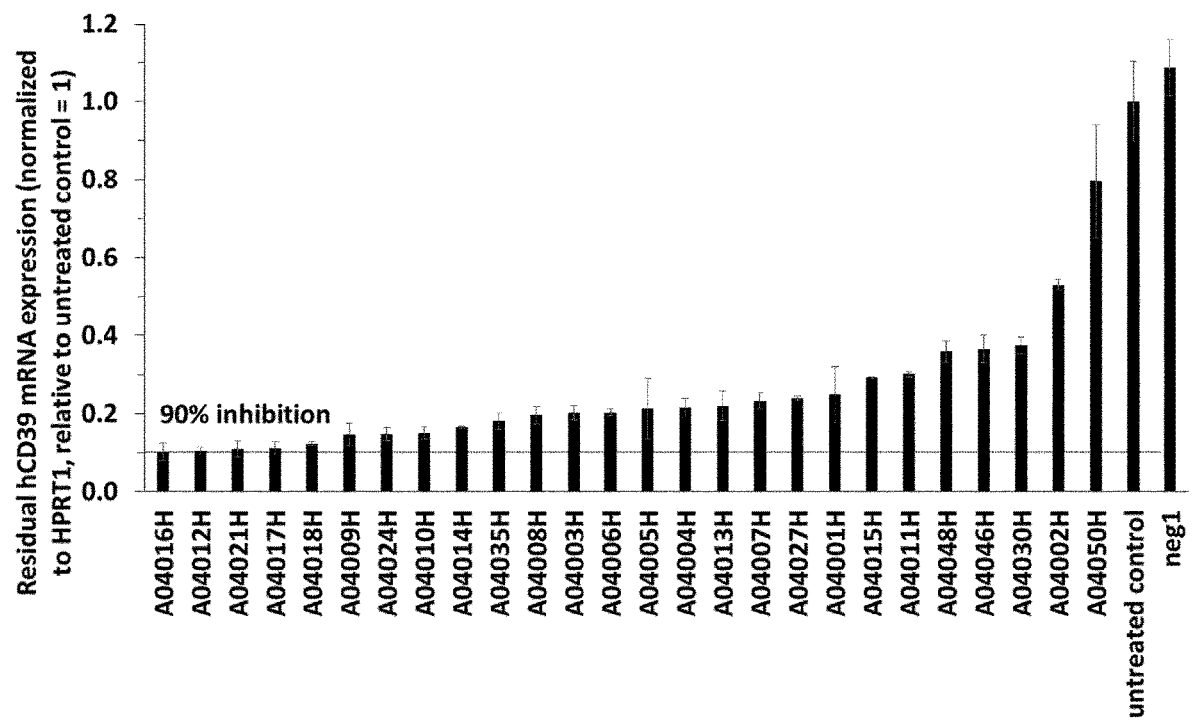
Figures 1, 2C:
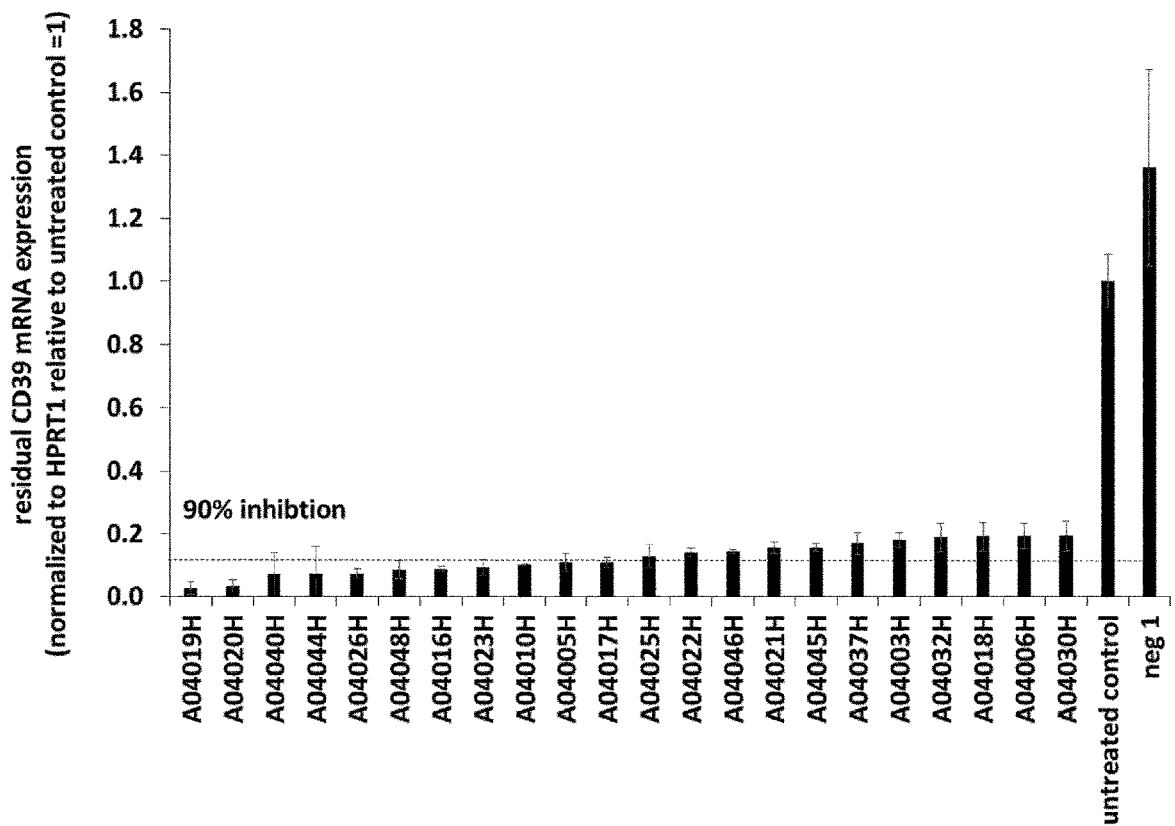
Figures 2, 2C:
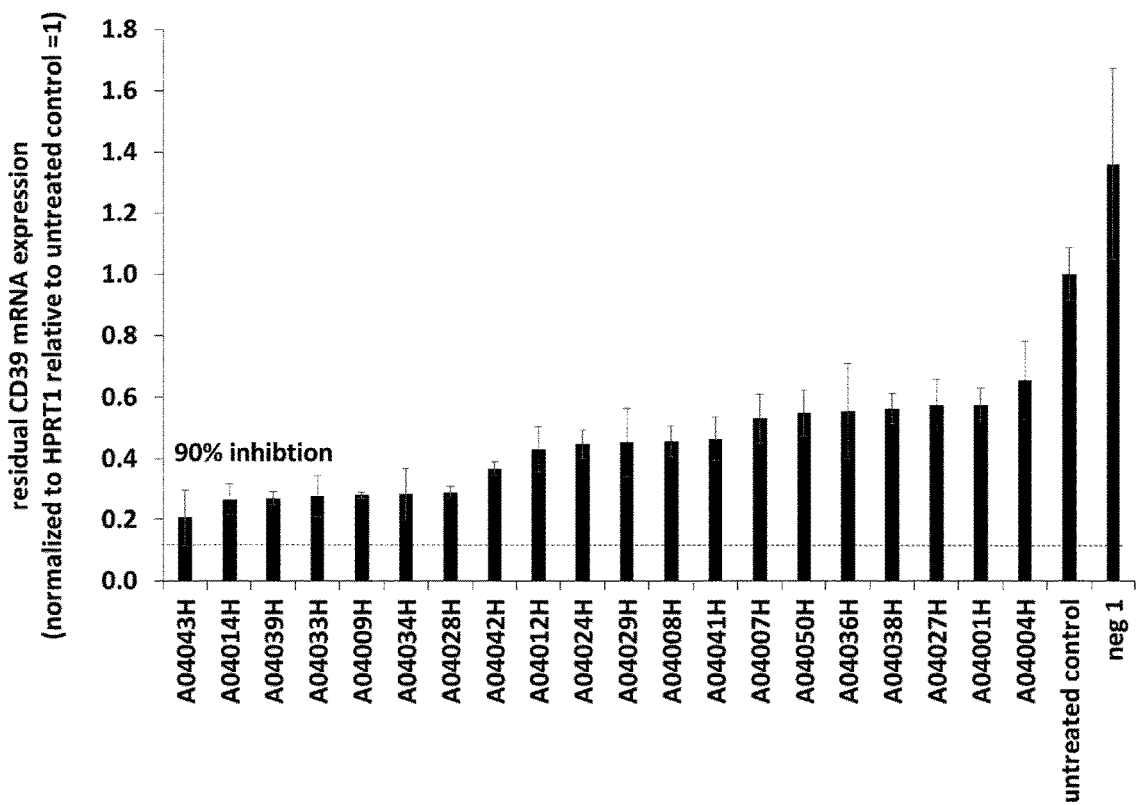
Figures 1, 2D:
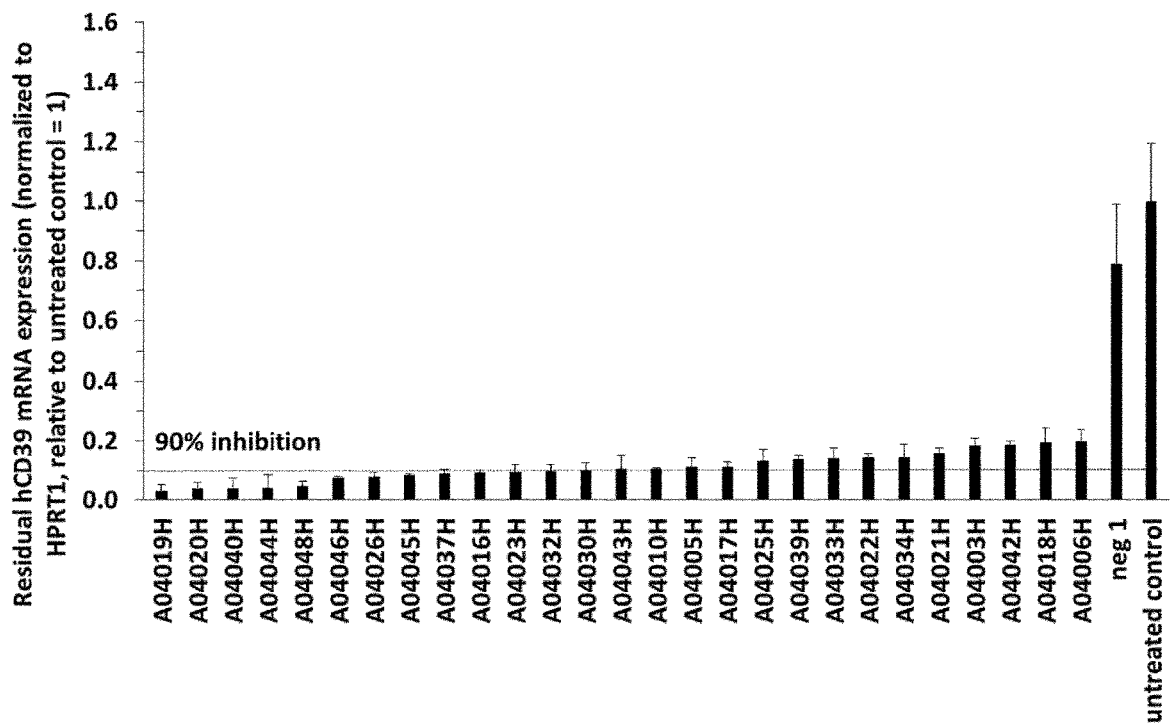
Figures 2, 2D:
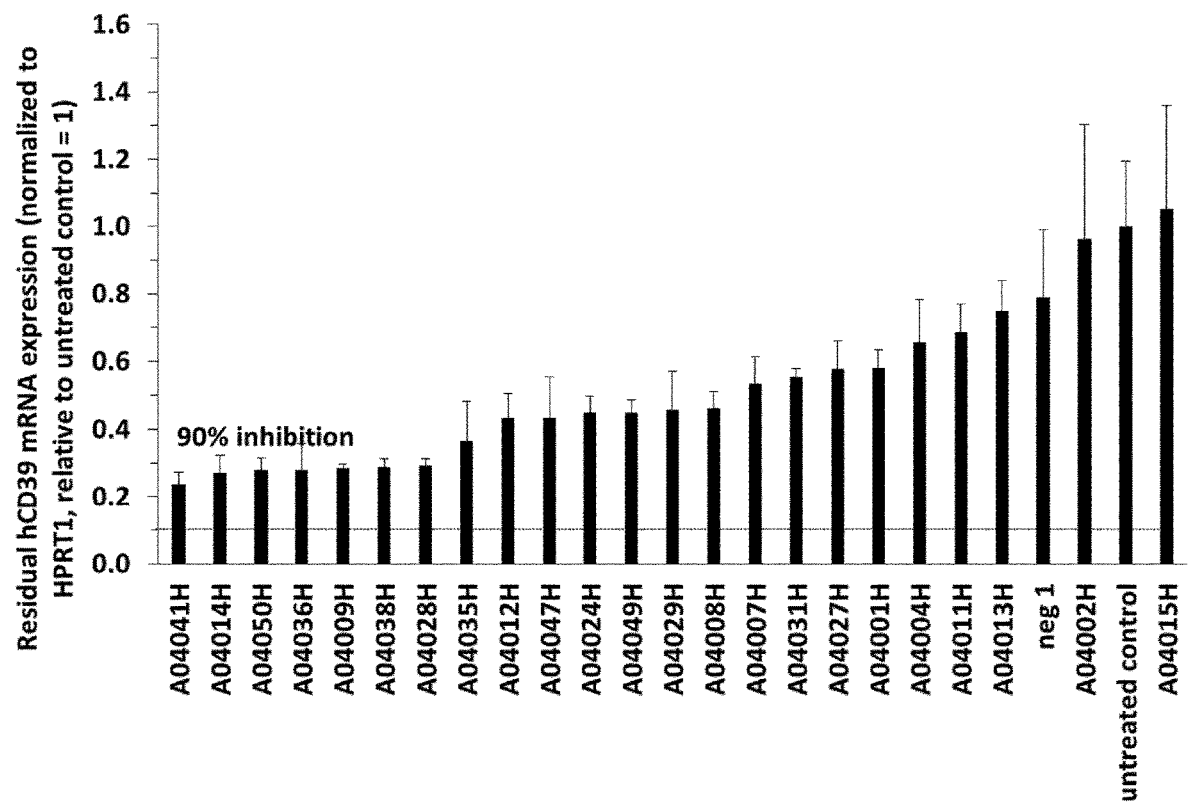

The present invention provides for the first time human and murine oligonucleotides which hybridize with mRNA sequences of the ectonucleotidase CD39 and inhibit the expression and activity, respectively, of CD39 for example on a tumor cell or a tumor-associated immune cell. In consequence, the level of ATP increases and the level of its degradation products such as ADP, AMP and immunosuppressive adenosine decreases. All these effects result in an increase of antitumoral immune cells, immune activation (e.g., via cytotoxic T cells or NK cells) and recognition and elimination of tumor cells, respectively. Thus, the oligonucleotides of the present invention represent an interesting and highly efficient tool for use in a method of preventing and/or treating disorders, where the CD39 expression and activity, respectively, is increased.

In the following, the elements of the present invention will be described in more detail. These elements are listed with specific embodiments, however, it should be understood that they may be combined in any manner and in any number to create additional embodiments. The variously described examples and embodiments should not be construed to limit the present invention to only the explicitly described embodiments. This description should be understood to support and encompass embodiments which combine the explicitly described embodiments with any number of the disclosed elements.

Furthermore, any permutations and combinations of all described elements in this application should be considered disclosed by the description of the present application unless the context indicates otherwise.

Throughout this specification and the claims, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by the context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as", "for example"), provided herein is intended merely to better illustrate the invention and does not pose a limitation on the scope of the invention otherwise claimed. No language in the specification should be construed as indicating any non-claimed element essential to the practice of the invention.

Oligonucleotides of the present invention are for example antisense oligonucleotides consisting of or comprising 10 to 25 nucleotides, 10 to 15 nucleotides, 15 to 20 nucleotides, 12 to 18 nucleotides, or 14 to 17 nucleotides. The oligonucleotides for example consist of or comprise 10, 11, 12, 13, 14, 15, 16, 17, 18, 19, 20 or 25 nucleotides. The oligonucleotides of the present invention comprise at least one nucleotide which is modified. The modified nucleotide is for example a bridged nucleotide such as a locked nucleic acid (LNA, e.g., 2',4'-LNA), cET, ENA, a 2'Fluoro modified nucleotide, a 2'O-Methyl modified nucleotide or combinations thereof. In some embodiments, the oligonucleotide of the present invention comprises nucleotides having the same or different modifications. In some embodiments the oligonucleotide of the present invention comprises a modified phosphate backbone, wherein the phosphate is for example a phosphorothioate.

The oligonucleotide of the present invention comprises the one or more modified nucleotide at the 3'- and/or 5'- end of the oligonucleotide and/or at any position within the oligonucleotide, wherein modified nucleotides follow in a row of 1, 2, 3, 4, 5, or 6 modified nucleotides, or a modified nucleotide is combined with one or more unmodified nucleotides. The following Tables 1, 2 and 3 present embodiments of oligonucleotides comprising modified nucleotides for example LNA which are indicated by (+) and phosphorothioate (PTO) indicated by (*). The oligonucleotides consisting of or comprising the sequences of Tables 1, 2 and 3, respectively, may comprise any other modified nucleotide and any other combination of modified and unmodified nucleotides. Oligonucleotides of Table 1 hybridize with mRNA of human CD39:

TABLE 1

List of antisense oligonucleotides hybridizing with human CD39 for example of SEQ ID No. 1; Neg1 is an antisense oligonucleotide representing a negative control which is not hybridizing with CD39 of SEQ ID No. 1.

| SEQ ID No. | Name | mRNA (Antisense) Sequence 5'-3' | Antisense Sequence 5'-3' with PTO (*) and LNA (+) |
|---|---|---|---|
| 3 | A04040H | GTTTGTGTGAGAGCTT | +G*+T*+T*T*G*T*G*T*G*A*G*A*G*C*+T*+T |
| 4 | A04045H | CACTTACGTTCACTACC | +C*+A*+C*T*T*A*C*G*T*T*C*A*C*T*+A*+C*+C |
| 5 | A04001H | GGCGAAATTGCAGA | +G*+G*+C*G*A*A*A*T*T*G*C*+A*+G*+A |
| 6 | A04002H | CTCCAGCGTAAGAT | +C*+T*+C*C*A*G*C*G*T*A*A*G*+A*+T |
| 7 | A04003H | TTGAACACTGCGAT | +T*+T*+G*A*A*C*A*C*T*G*C*+G*+A*+T |
| 8 | A04004H | GCCATAGGCACCTTC | +G*+C*C*A*T*A*G*G*C*A*C*C*+T*+T*+C |
| 9 | A04005H | CTATGCTGAACCACC | +C*+T*+A*T*G*C*T*G*A*A*C*C*+A*+C*+C |
| 10 | A04006H | TGTAGAGGCTCCCCC | +T*G*+T*A*G*A*G*G*C*T*C*C*+C*+C*+C |
| 11 | A04007H | TTGCAGAGCATTATC | +T*+T*+G*C*A*G*A*G*C*A*T*T*+A*+T*+C |
| 12 | A04008H | AGGCGAAATTGCAGA | +A*+G*+G*C*G*A*A*A*T*T*G*C*+A*+G*+A |
| 13 | A04009H | TAGACATTGTAGTCC | +T*+A*G*A*C*A*T*T*G*T*A*G*+T*+C*+C |
| 14 | A04010H | GAGTGCCTGATCCTT | +G*+A*G*T*G*C*C*T*G*A*T*C*C*+T*+T |
| 15 | A04011H | AATCCCCCTGGAGTG | +A*+A*+T*C*C*C*C*C*T*G*G*A*+G*+T*+G |
| 16 | A04012H | AGCGTAAGATGTTTT | +A*+G*+C*G*T*A*A*G*A*T*G*T*+T*+T*+T |
| 17 | A04013H | ACTCCAGCGTAAGAT | +A*+C*+T*C*C*A*G*C*G*T*A*A*+G*+A*+T |
| 18 | A04014H | TGATAGCCTTGCAGA | +T*+G*+A*T*A*G*C*C*T*T*G*C*+A*+G*+A |
| 19 | A04015H | AGTCCAGCCGGCGTC | +A*+G*T*C*C*A*G*C*C*G*G*C*G*T*+C |
| 20 | A04016H | GGACAATGGTTGCTC | +G*G*+A*C*A*A*T*G*G*T*T*G*+C*+T*+C |
| 21 | A04017H | CTTGAACACTGCGAT | +C*+T*+T*G*A*A*C*A*C*T*G*C*+G*+A*+T |
| 22 | A04018H | GAGTACAACTGAACC | +G*+A*G*T*A*C*A*A*C*T*G*A*+A*+C*+C |
| 23 | A04019H | GTAAGCCCTGATGTT | +G*+T*+A*A*G*C*C*C*T*G*A*T*+G*+T*+T |
| 24 | A04020H | TATGGTACAGTTGGT | +T*+A*+T*G*G*T*A*C*A*G*T*+T*G*+G*+T |
| 25 | A04021H | CTGACTGAATTTGCCC | +C*+T*+G*A*C*T*G*A*A*T*T*T*G*+C*+C*+C |
| 26 | A04022H | ACTATGCTGAACCACC | +A*+C*+T*A*T*G*C*T*G*A*A*C*C*+A*+C*+C |
| 27 | A04023H | GACTATGCTGAACCAC | +G*+A*C*T*A*T*G*C*T*G*A*A*C*+C*+A*+C |
| 28 | A04024H | GAGGCGAAATTGCAGA | +G*+A*+G*G*C*G*A*A*A*T*T*G*C*+A*+G*+A |
| 29 | A04025H | AGAGTGCCTGATCCTT | +A*+G*A*G*T*G*C*C*T*G*A*T*C*C*+T*+T |
| 30 | A04026H | GATAGTTTCCAATACC | +G*+A*+T*A*G*T*T*T*C*C*A*A*T*+A*+C*+C |
| 31 | A04027H | TACTCCAGCGTAAGAT | +T*+A*+C*T*C*C*A*G*C*G*T*A*A*+G*+A*+T |
| 32 | A04028H | ATGTAGCCCAAAGTCC | +A*+T*+G*T*A*G*C*C*C*A*A*A*G*+T*+C*+C |
| 33 | A04029H | CATGTAGCCCAAAGTC | +C*+A*+T*G*T*A*G*C*C*C*A*A*A*+G*+T*+C |
| 34 | A04030H | GGACAATGGTTGCTCA | +G*+G*+A*C*A*A*T*G*G*T*T*G*C*+T*+C*+A |
| 35 | A04031H | AGCCTATGATGGCCAC | +A*+G*+C*C*T*A*T*G*A*T*G*G*C*C*+A*+C |
| 36 | A04032H | GCCTTGAACACTGCGA | +G*+C*+C*T*T*G*A*A*C*A*C*T*G*C*+G*+A |
| 37 | A04033H | ACCCTGAGTTGTAACT | +A*+C*C*C*T*G*A*G*T*T*G*T*A*A*+C*+T |
| 38 | A04034H | AGGATAGTCTTGTCTC | +A*+G*G*A*T*A*G*T*C*T*T*G*T*C*+T*+C |

TABLE 1-continued

List of antisense oligonucleotides hybridizing with human CD39 for example of SEQ ID No. 1; Neg1 is an antisense oligonucleotide representing a negative control which is not hybridizing with CD39 of SEQ ID No. 1.

| SEQ ID No. | Name | mRNA (Antisense) Sequence 5'-3' | Antisense Sequence 5'-3' with PTO (*) and LNA (+) |
|---|---|---|---|
| 39 | A04035H | CCTACCCAGGATAGTC | +C*C*T*A*C*C*C*A*G*G*A*T*A*G*+T*+C |
| 40 | A04036H | CCCTCTCACTAAATTA | +C*+C*+C*T*C*T*C*A*C*T*A*A*A*+T*+A |
| 41 | A04037H | ACTCCACACTAATGCT | +A*+C*+T*C*C*A*C*A*C*T*A*A*T*+G*+C*+T |
| 42 | A04038H | GTCAATCCTGCTCAAC | +G*T*+C*A*A*T*C*C*T*G*C*T*C*A*+A*+C |
| 43 | A04039H | CAGTCAATCCTGCTCA | +C*+A*+G*T*C*A*A*T*C*C*T*G*C*+T*+C*+A |
| 44 | A04041H | CTTGCCATAGAGGCGAA | +C*T*+T*G*C*C*A*T*A*G*A*G*G*C*+G*A*+A |
| 45 | A04042H | TGCCAGAGTGCCTGATC | +T*+G*+C*C*A*G*A*G*T*G*C*C*T*G*+A*+T*+C |
| 46 | A04043H | ACGTTCACTACCTTCTT | +A*+C*+G*T*T*C*A*C*T*A*C*C*T*T*+C*+T*+T |
| 47 | A04044H | TTACGTTCACTACCTTC | +T*+T*+A*C*G*T*T*C*A*C*T*A*C*C*+T*+T*+C |
| 48 | A04046H | AAGGTCACTTACGTTCA | +A*+A*+G*G*T*C*A*C*T*T*A*C*G*T*+T*+C*+A |
| 49 | A04047H | GCCCCAAAATCCCCCTG | +G*+C*+C*C*C*A*A*A*A*T*C*C*C*C*+C*+T*+G |
| 50 | A04048H | GAGAGAATGTAGGTACC | +G*+A*+G*A*G*A*A*T*G*T*A*G*G*T*+A*C*+C |
| 51 | A04049H | CCCTGGATCTTGCCAAT | +C*+C*C*T*G*G*A*T*C*T*T*G*C*C*+A*+A*+T |
| 52 | A04050H | AAAGTCCAGCCGGCGTC | +A*+A*+A*G*T*C*C*A*G*C*C*G*G*C*+G*+T*+C |
| 53 | Neg1 |  | +C*+G*+T*T*T*A*G*G*C*T*A*T*G*T*A*+C*+T*+T |

Table 2 depicts further antisense oligonucleotides hybridizing with mRNA of human CD39 which were identified in another screening round:

TABLE 2

List of second round antisense oligonucleotides hybridizing with human CD39. neg 1 and S6 are control antisense oligonucleotides having no sequence complementarity to any human mRNA.

| SEQ ID No. | Name | mRNA (Antisense) Sequence 5'-3 | Antisense Sequence 5'-3' with PTO (*) and LNA (+) |
|---|---|---|---|
| 88 | A04051H | AGAGTGCCTGATCCTT | +A*+G*+A*G*T*G*C*C*T*G*A*T*C*+C*+T*+T |
| 89 | A04052H | TACGTTCACTACCTTCT | +T*+A*+C*G*T*T*C*A*C*T*A*C*C*T*+T*+C*+T |
| 89 | A04053H | TACGTTCACTACCTTCT | +T*+A*+C*G*T*T*C*A*C*T*A*C*C*T*+T*C*+T |
| 90 | A04054H | GCCCTGATGTTTGAAT | +G*+C*+C*C*T*G*A*T*G*T*T*T*G*+A*+A*+T |
| 91 | A04055H | TAGTAAGCCCTGATG | +T*+A*+G*T*A*A*G*C*C*C*T*G*+A*+T*+G |
| 92 | A04056H | GTTTGTGTGAGAGCTTT | +G*+T*+T*T*G*T*G*T*G*A*G*A*G*C*+T*+T*+T |
| 93 | A04058H | TTTGTGTGAGAGCTT | +T*+T*+T*G*T*G*T*G*A*G*A*G*+C*+T*+T |
| 94 | A04059H | GGTTTGTGTGAGAGCTT | +G*+G*+T*T*T*G*T*G*T*G*A*G*A*G*C*+T*+T |
| 95 | A04060H | GGTTTGTGTGAGAGCT | +G*+G*+T*T*T*G*T*G*T*G*A*G*A*G*C*+T |
| 96 | A04061H | GTTTGTGTGAGAGCT | +G*+T*+T*T*G*T*G*T*G*A*G*A*G*C*+T |
| 97 | A04062H | GGTTTGTGTGAGAGC | +G*+G*+T*T*T*G*T*G*T*G*A*G*+A*G*+C |

TABLE 2-continued

List of second round antisense oligonucleotides hybridizing with human CD39. neg 1 and S6 are control antisense oligonucleotides having no sequence complementarity to any human mRNA.

| SEQ ID No. | Name | mRNA (Antisense) Sequence 5'-3 | Antisense Sequence 5'-3' with PTO (*) and LNA (+) |
|---|---|---|---|
| 53 | neg 1 | | +C*+G*+T*T*T*A*G*G*C*T*A*T*G*T*A*+C*+T*+T |
| 98 | S6 | | +T*+C*+T*A*T*C*G*T*G*A*T*G*T*T*+T*+C*+T |

The following Table 3 shows oligonucleotides hybridizing with mRNA of rat or murine CD39:

TABLE 3

List of antisense oligonucleotides hybridizing with rat or murine CD39 for example of SEQ ID No. 2; Neg1 is an antisense oligonucleotide representing a negative control which is not hybridizing with CD39 of SEQ ID No. 2.

| SEQ ID No. | Name | mRNA (Antisense) Sequence 5'-3' | Antisense Sequence 5'-3' with PTO (*) and LNA (+) |
|---|---|---|---|
| 54 | A04011MR | AGTAATCCACCCATAG | +A*+G*+T*A*A*T*C*C*A*C*C*C*A*+T*+A*+G |
| 55 | A04001MR | AGTAATCCACCCATA | +A*+G*+T*A*A*T*C*C*A*C*C*C*+A*+T*+A |
| 56 | A04002MR | GATCCAAAGCGCCAA | +G*+A*+T*C*C*A*A*A*G*C*G*C*+C*+A*+A |
| 57 | A04003MR | GTTCGTAGTCTCCAG | +G*+T*+T*C*G*T*A*G*T*C*T*C*+C*+A*+G |
| 58 | A04004MR | CTGTTCGTAGTCTCC | +C*+T*+G*T*T*C*G*T*A*G*T*C*+T*+C*+C |
| 59 | A04005MR | GGTGGCACTGTTCGT | +G*+G*+T*G*G*C*A*C*T*G*T*T*+C*+G*+T |
| 60 | A04006MR | GTTATAGCCTTGCAG | +G*+T*+T*A*T*A*G*C*C*T*T*G*+C*+A*+G |
| 61 | A04007MR | CACATTAGCTGCACG | +C*+A*+C*A*T*T*A*G*C*T*G*C*+A*+C*+G |
| 62 | A04008MR | CCTAGTTGTGTATAC | +C*+C*+T*A*G*T*T*G*T*G*T*A*+T*+A*+C |
| 63 | A04009MR | GTACAGGTTGGTGTGA | +G*+T*+A*C*A*G*G*T*T*G*G*T*G*+T*+G*+A |
| 64 | A04010MR | CCACTTGTAGATGTAC | +C*+C*+A*C*T*T*G*T*A*G*A*T*G*+T*+A*+C |
| 65 | A04012MR | GCCCAGCAGATAGTTA | +G*+C*+C*C*A*G*C*A*G*A*T*A*G*+T*+T*+A |
| 66 | A04013MR | AGATCCAAAGCGCCAA | +A*+G*+A*T*C*C*A*A*A*G*C*G*C*+C*+A*+A |
| 67 | A04014MR | CACTGTTCGTAGTCTC | +C*+A*+C*T*G*T*T*C*G*T*A*G*T*+C*+T*+C |
| 68 | A04015MR | TGGCACTGTTCGTAGT | +T*+G*+G*C*A*C*T*G*T*T*C*G*T*+A*+G*+T |
| 69 | A04016MR | GGTACTTCTCCTTTAC | +G*+G*+T*A*C*T*T*C*T*C*C*T*T*+T*+A*+C |
| 70 | A04017MR | AGTTATAGCCTTGCAG | +A*+G*+T*T*A*T*A*G*C*C*T*T*G*+C*+A*+G |
| 71 | A04018MR | CGTTGCTGTCTTTGAT | +C*+G*+T*T*G*C*T*G*T*C*T*T*T*+G*+A*+T |
| 72 | A04019MR | GCTATACTGCCTCTTT | +G*+C*+T*A*T*A*C*T*G*C*C*T*C*+T*+T*+T |
| 73 | A04020MR | AGCATTTTGGCATCAC | +A*+G*+C*A*T*T*T*T*G*G*C*A*T*+C*+A*+C |
| 74 | A04021MR | CCTAGTTGTGTATACT | +C*+C*+T*A*G*T*T*G*T*G*T*A*T*+A*+C*+T |
| 75 | A04022MR | ACATTTCTTACTCGTT | +A*+C*+A*T*T*T*C*T*T*A*C*T*C*+G*+T*+T |
| 76 | A04023MR | GACCTTTCACTTGGCAT | +G*+A*+C*C*T*T*T*C*A*C*T*T*G*G*C*+A*+T |
| 77 | A04024MR | CCCAGCAGATAGTTAAT | +C*+C*+C*A*G*C*A*G*A*T*A*G*T*T*+A*+A*+T |
| 78 | A04025MR | GCCCAGCAGATAGTTAA | +G*+C*+C*C*A*G*C*A*G*A*T*A*G*T*+T*+A*+A |
| 79 | A04026MR | ATCCAAAGCGCCAAAGG | +A*+T*+C*C*A*A*A*G*C*G*C*C*A*+A*+A*+G*+G |

TABLE 3-continued

List of antisense oligonucleotides hybridizing with rat or murine CD39 for example of SEQ ID No. 2; Neg1 is an antisense oligonucleotide representing a negative control which is not hybridizing with CD39 of SEQ ID No. 2.

| SEQ ID No. | Name | mRNA (Antisense) Sequence 5'-3' | Antisense Sequence 5'-3' with PTO (*) and LNA (+) |
|---|---|---|---|
| 80 | A04027MR | TCGTAGTCTCCAGTGCC | +T*+C*+G*T*A*G*T*C*T*C*C*A*G*T*+G*+C*+C |
| 81 | A04028MR | TTCGTAGTCTCCAGTGC | +T*+T*+C*G*T*A*G*T*C*T*C*C*A*G*+T*+G*+C |
| 82 | A04029MR | TGTTCGTAGTCTCCAGT | +T*+G*+T*T*C*G*T*A*G*T*C*T*C*C*+A*+G*+T |
| 83 | A04030MR | GGTGGCACTGTTCGTAG | +G*+G*+T*G*G*C*A*C*T*G*T*T*C*G*+T*+A*+G |
| 84 | A04031MR | CGTTGCTGTCTTTGATC | +C*+G*+T*T*G*C*T*G*T*C*T*T*T*G*+A*+T*+C |
| 85 | A04032MR | GCTATACTGCCTCTTTC | +G*+C*+T*A*T*A*C*T*G*C*C*T*C*T*+T*+T*+C |
| 86 | A04033MR | TACATTTCTTACTCGTT | +T*+A*+C*A*T*T*T*C*T*T*A*C*T*C*+G*+T*+T |
| 87 | Neg1 | | +C*+G*+T*T*T*A*G*G*C*T*A*T*G*T*A*+C*+T*+T |

The oligonucleotides of the present invention hybridize for example with mRNA of human or murine CD39 of SEQ ID No. 1 and/or SEQ ID No. 2. Such oligonucleotides are called CD39 antisense oligonucleotides. In some embodiments, the oligonucleotides hybridize for example within positions 1000-1700 or 2500-3200 of CD39 mRNA for example of SEQ ID No. 1.

In some embodiments, the oligonucleotide of the present invention inhibits at least about 50%, 55%, 60%, 65%, 70%, 75%, 80%, 85%, 90%, 92%, 94%, 95%, 96%, 97%, 98%, 99% or 100% of CD39 such as the, e.g., human, rat or murine, CD39 expression. Thus, the oligonucleotides of the present invention are immunosuppression-reverting oligonucleotides which revert immunosuppression for example in a cell, tissue, organ, or a subject. The oligonucleotide of the present invention inhibits the expression of CD39 at a nanomolar or micromolar concentration for example in a concentration of 0.1, 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900 or 950 nM, or 1, 10 or 100 µM.

In some embodiments, the oligonucleotide of the present invention is used in a concentration of 1, 3, 5, 9, 10, 15, 27, 30, 40, 50, 75, 82, 100, 250, 300, 500, or 740 nM, or 1, 2.2, 3, 5, 6.6 or 10 µM.

In some embodiments the present invention refers to a pharmaceutical composition comprising an oligonucleotide of the present invention and a pharmaceutically acceptable carrier, excipient and/or dilutant. In some embodiments, the pharmaceutical composition further comprises a chemotherapeutic, another oligonucleotide, an antibody and/or a small molecule.

In some embodiments, the oligonucleotide or the pharmaceutical composition of the present invention is for use in a method of preventing and/or treating a disorder. In some embodiments, the use of the oligonucleotide or the pharmaceutical composition of the present invention in a method of preventing and/or treating a disorder is combined with radiotherapy. The radiotherapy may be further combined with a chemotherapy (e.g., platinum, gemcitabine). The disorder is for example characterized by an CD39 imbalance, i.e., the CD39 level is increased in comparison to the level in a normal, healthy cell, tissue, organ or subject. The CD39 level is for example increased by an increased CD39 expression and activity, respectively. The CD39 level can be measured by any standard method such as immunohistochemistry, western blot, quantitative real time PCR or QuantiGene assay known to a person skilled in the art.

An oligonucleotide or a pharmaceutical composition of the present invention is administered locally or systemically for example orally, sublingually, nasally, subcutaneously, intravenously, intraperitoneally, intramuscularly, intratumoral, intrathecal, transdermal and/or rectal. Alternatively or in combination ex vivo treated immune cells are administered. The oligonucleotide is administered alone or in combination with another immunosuppression-reverting oligonucleotide of the present invention and optionally in combination with another compound such as another oligonucleotide, an antibody or a fragment thereof such as a Fab fragment, a HERA fusion protein, a ligand trap, a nanobody, a BiTe, a small molecule and/or a chemotherapeutic (e.g., platinum, gemcitabine). In some embodiments, the other oligonucleotide (i.e., not being part of the present invention), the antibody, and/or the small molecule are effective in preventing and/or treating an autoimmune disorder, for example autoimmune arthritis or gastrointestinal autoimmune diseases such as inflammatory bowel disease (IBD) or colitis, an immune disorder, for example an immune exhaustion due to chronic viral infections such as HIV infection, a cardiovascular disorder, an inflammatory disorder for example a chronic airway inflammation, a bacterial, viral and/or fungal infection for example sepsis or a *Mycobacterium bovis* infection, a liver disorder, a chronic kidney disorder, a psychiatric disorder (e.g., schizophrenia, bipolar disorders, Alzheimer's disease) and/or cancer.

An oligonucleotide or a pharmaceutical composition of the present invention is used for example in a method of preventing and/or treating a solid tumor or a hematologic tumor. Examples of cancers preventable and/or treatable by use of the oligonucleotide or pharmaceutical composition of the present invention are breast cancer, lung cancer, malignant melanoma, lymphoma, skin cancer, bone cancer, prostate cancer, liver cancer, brain cancer, cancer of the larynx, gall bladder, pancreas, testicular, rectum, parathyroid, thyroid, adrenal, neural tissue, head and neck, colon, stomach, bronchi, kidneys, basal cell carcinoma, squamous cell carcinoma, metastatic skin carcinoma, osteo sarcoma, Ewing's sarcoma, reticulum cell sarcoma, liposarcoma, myeloma, giant cell tumor, small-cell lung tumor, islet cell tumor, primary brain tumor, meningioma, acute and chronic lymphocytic and granulocytic tumors, acute and chronic myeloid leukemia, hairy-cell tumor, adenoma, hyperplasia, medullary carcinoma, intestinal ganglioneuromas, Wilm's tumor, seminoma, ovarian tumor, leiomyomater tumor, cervical dysplasia, retinoblastoma, soft tissue sarcoma, malignant carcinoid, topical skin lesion, rhabdomyosarcoma, Kaposi's sarcoma, osteogenic sarcoma, malignant hypercalcemia, renal cell tumor, polycythermia vera, adenocarcinoma, anaplastic astrocytoma, glioblastoma multiforma, leukemia, or epidermoid carcinoma.

In some embodiments two or more oligonucleotides of the present invention are administered together, at the same time point for example in a pharmaceutical composition or separately, or on staggered intervals. In other embodiments, one or more oligonucleotides of the present invention are administered together with another compound such as another oligonucleotide (i.e., not being part of the present invention), an antibody, a small molecule and/or a chemotherapeutic, at the same time point for example in a pharmaceutical composition or separately, or on staggered intervals. In some embodiments of these combinations, the immunosuppression-reverting oligonucleotide inhibits the expression and activity, respectively, of an immune suppressive factor and the other oligonucleotide (i.e., not being part of the present invention), the antibody or a fragment thereof such as a Fab fragment, a HERA fusion protein, a ligand trap, a nanobody, a BiTe and/or small molecule inhibits (antagonist) or stimulates (agonist) the same and/or another immune suppressive factor. The immune suppressive factor and/or the immune stimulatory factor and/or an immune stimulatory factor. The immune suppressive factor is for example selected from the group consisting IDO1, IDO2, CTLA-4, PD-1, PD-L1, LAG-3, VISTA, A2AR, CD39, CD73, STAT3, TDO2, TIM-3, TIGIT, TGF-beta, BTLA, MICA, NKG2A, KIR, CD160, Chop, Xbp1 and a combination thereof. The immune stimulatory factor is for example selected from the group consisting of 4-1BB, Ox40, KIR, GITR, CD27, 2B4 and a combination thereof.

The immune suppressive factor is a factor whose expression and/or activity is for example increased in a cell, tissue, organ or subject. The immune stimulatory factor is a factor whose level is increased or decreased in a cell, tissue, organ or subject depending on the cell, tissue, organ or subject and its individual conditions.

An antibody in combination with the oligonucleotide or the pharmaceutical composition of the present invention is for example an anti-PD-1 antibody, an anti-PD-L1 antibody, or a bispecific antibody. A small molecule in combination with the oligonucleotide or the pharmaceutical composition of the present invention is for example ARL67156 (Onco-Immunology 1:3; 2012) or POM-1 (Gastroenterology; 2010; 139(3): 1030-1040).

A subject of the present invention is for example a mammalian, a bird or a fish.

EXAMPLES

The following examples illustrate different embodiments of the present invention, but the invention is not limited to these examples. The following experiments are performed on cells endogenously expressing IDO1, i.e., the cells do not represent an artificial system comprising transfected reporter constructs. Such artificial systems generally show a higher degree of inhibition and lower $IC_{50}$ values than endogenous systems which are closer to therapeutically relevant in vivo systems. Further, in the following experiments no transfecting agent is used, i.e., gymnotic delivery is performed. Transfecting agents are known to increase the activity of an oligonucleotide which influences the IC50 value (see for example Zhang et al., Gene Therapy, 2011, 18, 326-333; Stanton et al., Nucleic Acid Therapeutics, Vol. 22, No. 5, 2012). As artificial systems using a transfecting agent are hard or impossible to translate into therapeutic approaches and no transfection formulation has been approved so far for oligonucleotides, the following experiments are performed without any transfecting agent.

Example 1: Design of Human CD39 Antisense Oligonucleotides

For the design of antisense oligonucleotides with specificity for human (h) CD39 the hCD39 mRNA sequence with SEQ ID No. 1 (seq. ref. ID NM_001776.5) was used. 14, 15, 16 and 17 mers were designed according to in-house criteria, neg1 (described in WO2014154843 A1) was used as control antisense oligonucleotide in all experiments (Table 1). The distribution of the antisense oligonucleotide binding site on the hCD39 mRNA is shown in FIG. 1.

Example 2: Efficacy Screen of hCD39 Antisense Oligonucleotides in Human Cancer Cell Lines In order to analyze the efficacy of hCD39 antisense oligonucleotides of the present invention with regard to the knockdown of hCD39 mRNA expression in cancer cell lines, HDLM-2 (human Hodgkin Lymphoma, DSMZ) and A-172 (human glioblastoma, ATCC) cells were treated with a single dose (concentration: 10 µM without addition of any transfection reagent; this process is called gymnotic delivery) of the respective antisense oligonucleotide as shown in FIG. 2A to 2D. hCD39 and HPRT1 mRNA expression was analyzed three days later using the QuantiGene Singleplex assay (Affymetrix) and hCD39 expression values were normalized to HPRT1 values. Strikingly, a knockdown efficiency of >90% was observed for 23 and 18 (HDLM-2 cells; see FIGS. 2A and 2B) and of >90% was observed for 8 and 10 (A-172 cells) antisense oligonucleotides (see FIGS. 2C and 2D). Values of the mean normalized mRNA expression of hCD39 compared to non-treated cells are listed for A-172 (Table 4 for first screening round and Table 5 for second screening round) and HDLM-2 cells (Table 6 for first screening round and Table 7 for second screening round) in the following:

TABLE 4

List of mean normalized hCD39 mRNA expression values in antisense oligonucleotide-treated A-172 cells compared to untreated cells (first screening round).

| Compound ID | Mean hCD39 mRNA expression (relative to untreated cells set as 1) |
|---|---|
| A04019H | 0.03 |
| A04020H | 0.03 |
| A04040H | 0.07 |
| A04044H | 0.07 |
| A04026H | 0.07 |
| A04048H | 0.09 |
| A04016H | 0.09 |
| A04023H | 0.09 |
| A04010H | 0.10 |
| A04005H | 0.11 |
| A04017H | 0.11 |
| A04025H | 0.13 |
| A04022H | 0.14 |

TABLE 4-continued

List of mean normalized hCD39 mRNA expression values in antisense oligonucleotide-treated A-172 cells compared to untreated cells (first screening round).

| Compound ID | Mean hCD39 mRNA expression (relative to untreated cells set as 1) |
|---|---|
| A04046H | 0.14 |
| A04021H | 0.16 |
| A04045H | 0.16 |
| A04037H | 0.17 |
| A04003H | 0.18 |
| A04032H | 0.19 |
| A04018H | 0.19 |
| A04006H | 0.19 |
| A04030H | 0.19 |
| A04043H | 0.21 |
| A04014H | 0.27 |
| A04039H | 0.27 |
| A04033H | 0.28 |
| A04009H | 0.28 |
| A04034H | 0.28 |
| A04028H | 0.29 |
| A04042H | 0.37 |
| A04012H | 0.43 |
| A04024H | 0.45 |
| A04029H | 0.45 |
| A04008H | 0.46 |
| A04041H | 0.46 |
| A04007H | 0.53 |
| A04050H | 0.55 |
| A04036H | 0.55 |
| A04038H | 0.56 |
| A04027H | 0.58 |
| A04001H | 0.58 |
| A04004H | 0.65 |
| untreated control | 1.00 |
| neg 1 | 1.36 |

TABLE 5

List of mean normalized hCD39 mRNA expression values in antisense oligonucleotide-treated A-172 cells compared to untreated cells (second screening round).

| ASO | Relative hCD39 mRNA expression (compared to non-treated cells) |
|---|---|
| A04019H | 0.03 |
| A04020H | 0.04 |
| A04040H | 0.04 |
| A04044H | 0.04 |
| A04048H | 0.05 |
| A04046H | 0.08 |
| A04026H | 0.08 |
| A04045H | 0.08 |
| A04037H | 0.09 |
| A04016H | 0.09 |
| A04023H | 0.10 |
| A04032H | 0.10 |
| A04030H | 0.10 |
| A04043H | 0.11 |
| A04010H | 0.11 |
| A04005H | 0.11 |
| A04017H | 0.11 |
| A04025H | 0.13 |
| A04039H | 0.14 |
| A04033H | 0.14 |
| A04022H | 0.15 |
| A04034H | 0.15 |
| A04021H | 0.16 |
| A04003H | 0.18 |
| A04042H | 0.19 |
| A04018H | 0.20 |
| A04006H | 0.20 |
| A04041H | 0.24 |

TABLE 5-continued

List of mean normalized hCD39 mRNA expression values in antisense oligonucleotide-treated A-172 cells compared to untreated cells (second screening round).

| ASO | Relative hCD39 mRNA expression (compared to non-treated cells) |
|---|---|
| A04014H | 0.27 |
| A04050H | 0.28 |
| A04036H | 0.28 |
| A04009H | 0.29 |
| A04038H | 0.29 |
| A04028H | 0.29 |
| A04035H | 0.37 |
| A04012H | 0.43 |
| A04047H | 0.43 |
| A04024H | 0.45 |
| A04049H | 0.45 |
| A04029H | 0.46 |
| A04008H | 0.46 |
| A04007H | 0.53 |
| A04031H | 0.55 |
| A04027H | 0.58 |
| A04001H | 0.58 |
| A04004H | 0.66 |
| A04011H | 0.69 |
| A04013H | 0.75 |
| neg 1 | 0.79 |
| A04002H | 0.96 |
| No ASO | 1.00 |
| A04015H | 1.05 |

TABLE 6

List of mean normalized hCD39 mRNA expression values in antisense oligonucleotide-treated HDLM-2 cells compared to untreated cells.

| Compound ID | Mean hCD39 mRNA expression normalized to HPRT1 relative to untreated control = 1 |
|---|---|
| A04029H | 0.03 |
| A04026H | 0.03 |
| A04043H | 0.04 |
| A04046H | 0.04 |
| A04048H | 0.05 |
| A04044H | 0.05 |
| A04032H | 0.06 |
| A04023H | 0.06 |
| A04034H | 0.06 |
| A04039H | 0.06 |
| A04030H | 0.07 |
| A04028H | 0.07 |
| A04040H | 0.08 |
| A04019H | 0.08 |
| A04020H | 0.08 |
| A04025H | 0.08 |
| A04045H | 0.09 |
| A04022H | 0.09 |
| A04033H | 0.10 |
| A04042H | 0.10 |
| A04016H | 0.10 |
| A04012H | 0.11 |
| A04050H | 0.11 |
| A04021H | 0.11 |
| A04017H | 0.11 |
| A04037H | 0.12 |
| A04018H | 0.12 |
| A04009H | 0.15 |
| A04024H | 0.15 |
| A04014H | 0.17 |
| A04010H | 0.17 |
| A04035H | 0.17 |
| A04041H | 0.18 |
| A04008H | 0.20 |
| A04038H | 0.20 |
| A04003H | 0.20 |
| A04006H | 0.20 |

TABLE 6-continued

List of mean normalized hCD39 mRNA expression values in antisense oligonucleotide-treated HDLM-2 cells compared to untreated cells.

| Compound ID | Mean hCD39 mRNA expression normalized to HPRT1 relative to untreated control = 1 |
|---|---|
| A04005H | 0.21 |
| A04004H | 0.22 |
| A04013H | 0.22 |
| A04007H | 0.23 |
| A04027H | 0.24 |
| A04001H | 0.25 |
| A04036H | 0.26 |
| A04011H | 0.29 |
| A04015H | 0.29 |
| untreated control | 1.00 |
| neg 1 | 1.09 |

TABLE 7

List of mean normalized hCD39 mRNA expression values in antisense oligonucleotide-treated HDLM-2 cells compared to untreated cells.

| ASO | Relative hCD39 mRNA expression (compared to non-treated cells) |
|---|---|
| A03045H = A04045H | * |
| A03042H = A04042H | * |
| A03047H = A04047H | * |
| A03041H = A04041H | * |
| A03043H = A04043H | * |
| A03039H = A04039H | * |
| A03049H = A04049H | * |
| A03038H = A04038H | * |
| A03044H = A04044H | * |
| A03033H = A04033H | * |
| A03031H = A04031H | * |
| A03036H = A04036H | 0.01 |
| A03032H = A04032H | 0.01 |
| A03029H = A04029H | 0.03 |
| A03026H = A04026H | 0.03 |
| A03040H = A04040H | 0.06 |
| A03023H = A04023H | 0.06 |
| A03034H = A04034H | 0.06 |
| A03028H = A04028H | 0.07 |
| A03019H = A04019H | 0.08 |
| A03020H = A04020H | 0.08 |
| A03025H = A04025H | 0.08 |
| A03022H = A04022H | 0.09 |
| A03037H = A04037H | 0.10 |
| A03016H = A04016H | 0.10 |
| A03012H = A04012H | 0.10 |
| A03021H = A04021H | 0.11 |
| A03017H = A04017H | 0.11 |
| A03018H = A04018H | 0.12 |
| A03009H = A04009H | 0.15 |
| A03024H = A04024H | 0.15 |
| A03010H = A04010H | 0.15 |
| A03014H = A04014H | 0.17 |
| A03035H = A04035H | 0.18 |
| A03008H = A04008H | 0.20 |
| A03003H = A04003H | 0.20 |
| A03006H = A04006H | 0.20 |
| A03005H = A04005H | 0.21 |
| A03004H = A04004H | 0.21 |
| A03013H = A04013H | 0.22 |
| A03007H = A04007H | 0.23 |
| A03027H = A04027H | 0.24 |
| A03001H = A04001H | 0.25 |
| A03015H = A04015H | 0.29 |
| A03011H = A04011H | 0.30 |
| A03048H = A04048H | 0.36 |
| A03046H = A04046H | 0.37 |
| A03030H = A04030H | 0.38 |
| A03002H = A04002H | 0.53 |
| A03050H = A04050H | 0.90 |
| neg1 | 1.09 |

(* = values are below detection limit; second screening round).

Example 3: Correlation Analysis of Antisense Oligonucleotide Efficacy in HDLM-2 and A-172 Cells To further select the candidates with the highest activity in both tested cell lines, HDLM-2 and A-172, a correlation analysis was performed (data derived from FIGS. 2B and 2D). As depicted in FIG. 3, 7 potent antisense oligonucleotides for determination of $IC_{50}$ in HDLM-2 and A-172 cells, namely A04019H (SEQ ID No. 23), A04033H (SEQ ID No. 37), A04039H (SEQ ID No. 43), A04040H (SEQ ID No. 3), A04042H (SEQ ID No. 45), A04044H (SEQ ID No. 47) and A04045H (SEQ ID No. 4) (marked in black) were selected. Importantly, the control antisense oligonucleotide neg1 had no negative influence on the expression of hCD39 in both cell lines.

Example 4: $IC_{50}$ Determination of Selected hCD39
Antisense Oligonucleotides in HDLM-2 Cells
(mRNA level) in a First Screening Round In order to determine the $IC_{50}$ of the hCD39 antisense oligonucleotides A04019H (SEQ ID No. 23), A04033H (SEQ ID No. 37), A04039H (SEQ ID No. 43), A04040H (SEQ ID No. 3), A04042H (SEQ ID No. 45), A04044H (SEQ ID No. 47), A04045H (SEQ ID No. 4), HDLM-2 cells were treated with titrated amounts of the respective antisense oligonucleotide (concentrations: 10 µM, 3.3 µM, 1.1 µM, 370 nM, 120 nM, 41 nM, 14 nM, 4.5 nM). hCD39 mRNA expression was analyzed three days later. As shown in FIG. 4 and following Table 8, the antisense oligonucleotides A04040H (SEQ ID No. 3) and A04045H (SEQ ID No. 4) had the highest potency in HDLM-2 cells with regard to downregulation of hCD39 mRNA compared to untreated cells with a maximal target inhibition of 99% and 99.2%, respectively. Table 8 shows $IC_{50}$ values and target inhibition of the above mentioned selected antisense oligonucleotides at titrated concentrations in HDLM-2 cells:

TABLE 8

Overview of $IC_{50}$ values for hCD39 antisense oligonucleotides

| ASO | $IC_{50}$ [nM] | mRNA inhibition [in %] | | | | | | | |
|---|---|---|---|---|---|---|---|---|---|
| | | 10 µM | 3.3 µM | 1.1 µM | 0.4 µM | 0.12 µM | 0.04 µM | 0.013 µM | 0.0045 µM |
| A04019H | 39.98 | 98.39 | 97.89 | 95.46 | 88.83 | 69.42 | 38.76 | 8.19 | −11.65 |
| A04033H | 119.1 | 98.02 | 92.79 | 83.81 | 70.74 | 46.98 | 24.10 | −3.30 | 3.05 |
| A04039H | 176.9 | 96.54 | 92.53 | 85.22 | 71.25 | 44.03 | 20.47 | 14.30 | 11.56 |
| A04040H | 25.28 | 98.98 | 99.01 | 98.54 | 95.94 | 88.40 | 62.42 | 40.51 | 22.64 |
| A04042H | 60.89 | 95.87 | 87.12 | 76.38 | 58.07 | 32.44 | 22.51 | −2.65 | −20.02 |
| A04044H | 46.29 | 98.71 | 96.20 | 91.19 | 82.63 | 68.28 | 45.88 | 26.25 | 12.17 |
| A04045H | 66.75 | 99.19 | 97.44 | 95.07 | 87.63 | 73.62 | 54.20 | 33.03 | 30.70 |

Example 5: $IC_{50}$ Determination of Selected hCD39
Antisense Oligonucleotides in HDLM-2 Cells
(mRNA Level) in a Second Screening Round In a second experiment the concentration-dependency of effects and the $IC_{50}$ values of hCD39 antisense oligonucleotides A04010H (SEQ ID No.14), A04016H (SEQ ID No.20), A04017H (SEQ ID No.21), A04020H (SEQ ID No. 24) and A04026H (SEQ ID No.30) were tested. The antisense oligonucleotides A04019H (SEQ ID No.23) and A04040H (SEQ ID No.3) that showed potent activity in the first $IC_{50}$ determination were used as reference. HDLM-2 cells were treated with titrated amounts of the respective antisense oligonucleotide (concentrations: 10 µM, 3.3 µM, 1.1 µM, 370 nM, 120 nM, 41 nM, 14 nM, 4.5 nM). hCD39 mRNA expression was analyzed after three days of treatment. FIG. 5 and Table 9 depicts the concentration-dependent reduction of hCD39 mRNA expression by the selected hCD39 antisense oligonucleotides. The antisense oligonucleotides A04016H, A04019H, A04020H and A04040H had the highest potency in suppressing hCD39 mRNA in HDLM-2 cells indicated by $IC_{50}$ values of 12.8 nM (A04016H), 11.58 nM (A04019H), 10.11 nM (A04020H), and 21.53 nM (A04040H).

TABLE 9

$IC_{50}$ values and target inhibition of selected antisense oligonucleotides at titrated concentrations in HDLM-2 cells:

| ASO | $IC_{50}$ [nM] | mRNA inhibition [in %] | | | | | | | |
|---|---|---|---|---|---|---|---|---|---|
| | | 10 µM | 3.3 µM | 1.1 µM | 0.4 µM | 0.12 µM | 0.04 µM | 0.013 µM | 0.0045 µM |
| A04010H | 51.58 | 98.77 | 98.10 | 95.99 | 90.86 | 76.16 | 52.80 | 24.68 | 20.11 |
| A04016H | 12.8 | 98.94 | 98.38 | 96.67 | 90.51 | 77.61 | 62.31 | 42.19 | 18.41 |
| A04017H | 33.14 | 99.37 | 98.95 | 97.05 | 91.63 | 79.03 | 62.92 | 49.62 | 33.85 |
| A04019H | 11.58 | 99.00 | 99.04 | 97.94 | 93.96 | 82.63 | 62.95 | 49.52 | 22.53 |
| A04020H | 10.11 | 99.41 | 99.55 | 99.61 | 99.42 | 98.89 | 94.26 | 68.27 | 23.58 |
| A04026H | 61.5 | 98.59 | 99.20 | 96.69 | 92.99 | 77.36 | 54.32 | 29.02 | 29.98 |
| A04040H | 21.53 | 99.57 | 99.32 | 99.38 | 98.42 | 93.14 | 74.68 | 36.68 | 12.51 |

Figure 6A:
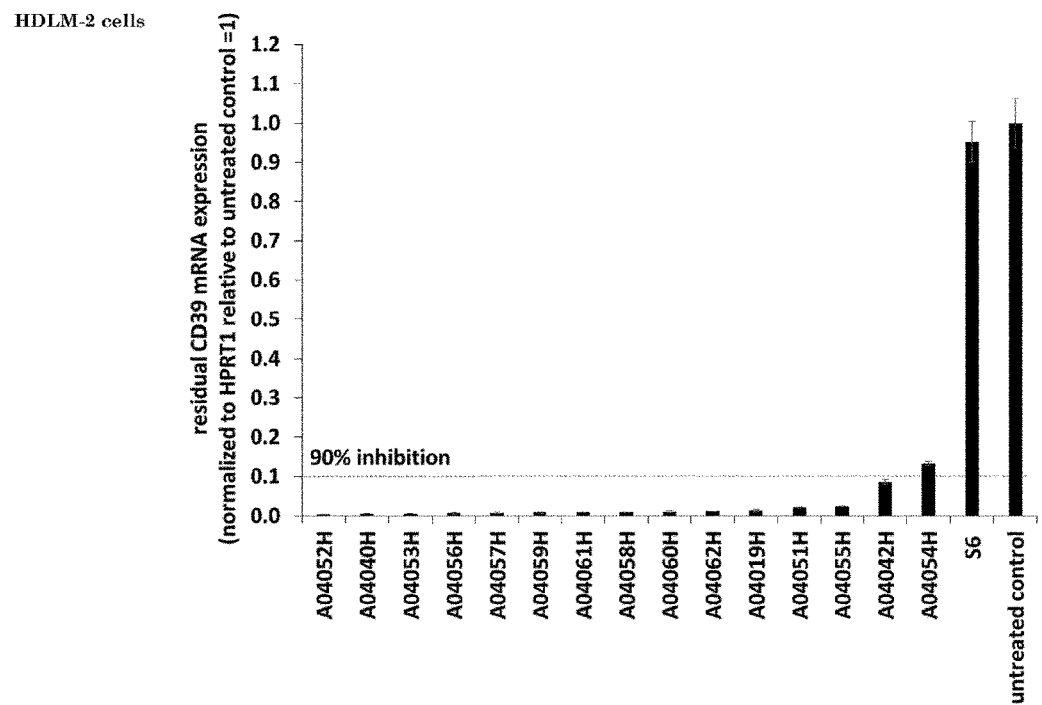
FIGS. 6A-6B depicts a third screening round where further antisense oligonucleotides were designed. These antisense oligonucleotides were based on efficient antisense oligonucleotides from the first and second screening round. Therefore, hCD39 antisense oligonucleotides were tested in human cancer cell lines HDLM-2 (human Hodgkin's lymphoma) (FIG. 6A) and A-172 (human glioblastoma) (FIG. 6B). HDLM-2 and A-172 cells were treated for 3 days with 10 μM of the respective antisense oligonucleotide. The antisense oligonucleotides A04019H, A04040H, and A04042H that showed potent activity in the first screening round were used as reference. Residual hCD39 mRNA expression relative to untreated cells (set as 1) is depicted.
Figure 6B:
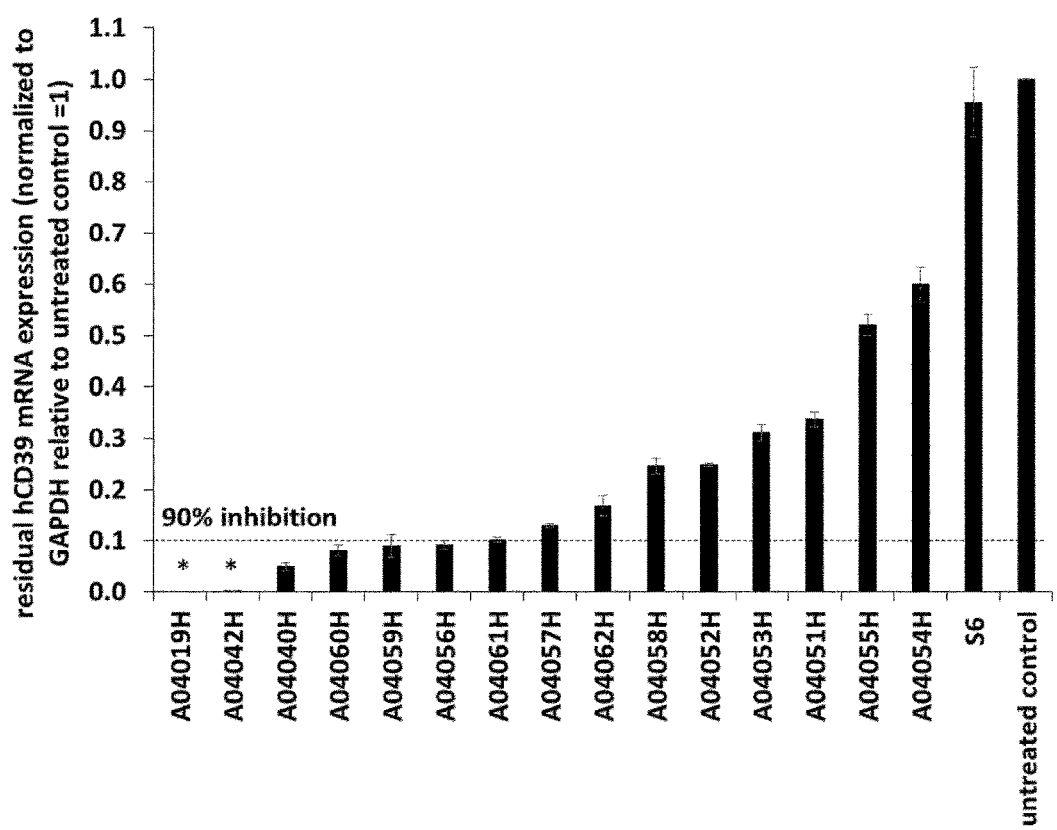

Example 6: Third Screening Round of hCD39 Antisense Oligonucleotides in Human Cancer Cell Lines For a third screening round, new antisense oligonucleotides were designed. These antisense oligonucleotides were based on efficient antisense oligonucleotides from the first screening round with modifications in length, exact position on mRNA and chemical modification pattern. Therefore, hCD39 antisense oligonucleotides were tested in human cancer cell lines (FIG. 6A, Table 10) HDLM-2 (human Hodgkin's lymphoma) and (FIG. 6B, Table 11) A-172 (human glioblastoma). HDLM-2 and A-172 cells were treated for 3 days with 10 µM of the respective antisense oligonucleotide. The antisense oligonucleotides A04019H (SEQ ID No.23), A04040H (SEQ ID No.3), and A04042H (SEQ ID No.45) that showed potent activity in the first screening round were used as reference. Residual hCD39 mRNA expression relative to untreated cells (set as 1) is depicted.

TABLE 10

Mean normalized hCD39 mRNA expression values in antisense oligonucleotide-treated HDLM-2 cells relative to untreated cells (set as 1).

| Oligo ID | Residual hCD39 mRNA expression relative to untreated cells (set as 1) |
|---|---|
| A04052H | 0.00 |
| A04040H | 0.01 |
| A04053H | 0.01 |
| A04056H | 0.01 |
| A04057H | 0.01 |
| A04059H | 0.01 |
| A04061H | 0.01 |
| A04058H | 0.01 |
| A04060H | 0.01 |
| A04062H | 0.01 |
| A04019H | 0.01 |
| A04051H | 0.02 |
| A04055H | 0.03 |
| A04042H | 0.09 |
| A04054H | 0.13 |
| S6 | 0.95 |
| untreated control | 1.00 |

TABLE 11

Mean normalized hCD39 mRNA expression values in antisense oligonucleotide-treated A-172 cells relative to untreated cells (set as 1).

| Oligo ID | Residual hCD39 mRNA expression relative to untreated cells (set as 1) | ± SD |
|---|---|---|
| A04019H | 0.00 | 0.00 |
| A04042H | 0.00 | 0.00 |
| A04040H | 0.05 | 0.01 |
| A04060H | 0.08 | 0.01 |
| A04059H | 0.09 | 0.02 |
| A04056H | 0.09 | 0.01 |
| A04061H | 0.10 | 0.00 |
| A04057H | 0.13 | 0.00 |
| A04062H | 0.17 | 0.02 |
| A04058H | 0.25 | 0.02 |
| A04052H | 0.25 | 0.00 |
| A04053H | 0.31 | 0.02 |
| A04051H | 0.34 | 0.01 |
| A04055H | 0.52 | 0.02 |
| A04054H | 0.60 | 0.03 |
| S6 | 0.95 | 0.07 |
| untreated control | 1.00 | 0.00 |

Example 7: IC$_{50}$ Determination of Selected hCD39 Antisense Oligonucleotides of a Third Screening Round in HDLM-2 Cells (mRNA Level)

The hCD39 antisense oligonucleotides A04051H (SEQ ID No.88), A04052H (SEQ ID No.89), A04053H (SEQ ID No.89), A04056H (SEQ ID No.92), A04059H (SEQ ID No.94), A04060H (SEQ ID No.95), and A04061H (SEQ ID No.96) had shown potent single-dose activity in both HDLM-2 and A-172 cells. In order to investigate the concentration-dependency of effects and to determine the IC$_{50}$ values of HDLM-2 cells were treated with 1000 nM; 330 nM; 110 nM; 40 nM; 12 nM; 4 nM; 1.3 nM; 0.45 nM of the respective antisense oligonucleotide. The antisense oligonucleotide A04040H that had shown potent activity in the first screening round was used as reference. hCD39 mRNA expression was analyzed after 3 days of treatment. FIG. 7 depicts the concentration-dependent reduction of hCD39 expression by hCD39 antisense oligonucleotides. IC$_{50}$-values and target inhibition are shown in Table 12. Accordingly, the antisense oligonucleotides A04056H; A04059H; and A04060H had the highest potency in suppressing hCD39 mRNA in HDLM-2 cells indicated by IC$_{50}$ values of 20.2 nM (A04056H); 18.32 nM (A04059H), or 20.5 nM (A04060H).

TABLE 12

IC$_{50}$ values and target inhibition of selected antisense oligonucleotides from third screening round at titrated concentrations in HDLM-2 cells (n.d. = not determined):

| | | mRNA inhibition [in %] | | | | | | | |
|---|---|---|---|---|---|---|---|---|---|
| ASO | IC$_{50}$ [nM] | 1000 nM | 330 nM | 110 nM | 40 nM | 12 nM | 4 nM | 1.3 nM | 0.45 nM |
| A04040H | 52.79 | 97.06 | 91.26 | 69.84 | 27.56 | 0.00 | 0.00 | 0.00 | 0.00 |
| A04051H | 68.96 | 92.82 | 86.77 | 70.34 | 43.66 | 23.14 | 23.62 | 15.36 | 30.83 |
| A04052H | 53.96 | 94.72 | 88.35 | 75.30 | 49.21 | 31.25 | 9.03 | 25.80 | 24.52 |
| A04053H | 67.6 | 92.69 | 85.19 | 66.64 | 37.75 | 26.67 | 9.81 | 17.51 | 2.07 |
| A04056H | 20.2 | 98.49 | 97.52 | 91.83 | 69.95 | 37.12 | 13.97 | n.d. | n.d. |
| A04059H | 18.32 | 98.31 | 97.46 | 91.84 | 72.06 | 12.94 | 0.00 | 0.00 | 1.21 |
| A04060H | 20.5 | 97.82 | 96.71 | 88.34 | 49.14 | 0.00 | 0.00 | 0.00 | 0.00 |
| A04061H | 66.85 | 97.43 | 92.28 | 69.28 | 19.90 | 0.00 | 0.00 | n.d. | n.d. |

Example 8: Concentration- and Time-Dependent hCD39 Protein Knockdown by A04040H (SEQ ID No. 3) and A04045H (SEQ ID No. 4)

The highly potent hCD39 antisense oligonucleotides A04040H (SEQ ID No. 3) and A04045H (SEQ ID No. 4) were characterized in detail with regard to their knockdown efficacy on the hCD39 protein expression and their influence on cell viability at different concentrations. HDLM-2 cells were therefore treated with different concentrations of the respective antisense oligonucleotide for three, four and six days, respectively. Protein expression was analyzed by flow cytometry using the CD39 antibody (clone A1) and 7-AAD to investigate viability. As shown in FIG. 8, both antisense oligonucleotides show potent inhibition of hCD39 protein after all indicated time points, whereas treatment with neg1 had no inhibitory effect. In contrast, A04045H (SEQ ID No. 4) did not affect viability of HDLM-2 cells in any of the conditions tested. Table 13 summarizes protein knockdown efficiency of the selected human CD39 antisense oligonucleotides A04040H (SEQ ID No. 3) and A04045H (SEQ ID No. 4) in HDLM-2 cells at different time points:

TABLE 13

Protein knockdown efficiency of selected human CD39 antisense oligonucleotides in HDLM-2 cells

| ASO | Timepoints after ASO treatment | Inhibition [%] (Protein/mRNA) | | | |
|---|---|---|---|---|---|
| | | 10 µM | 1 µM | 0.5 µM | 0.1 µM |
| A04040H | Day 3 | 61.36 | 60.56 | 54.75 | 46.73 |
| | Day 4 | 79.11 | 76.96 | 78.25 | 70.73 |
| | Day 6 | 88.84 | 84.12 | 89.36 | 87.37 |
| A04045H | Day 3 | 54.88 | 51.53 | 50.37 | 38.81 |
| | Day 4 | 78.72 | 75.55 | 73.20 | 61.88 |
| | Day 6 | 94.06 | 90.46 | 89.53 | 80.24 |

Example 9: Investigation of Effects of hCD39-Specific Antisense Oligonucleotides on hCD39 Protein Expression in Primary Human CD4$^+$ and CD8$^+$ T Cells and Investigation of Persistence of Effects After Oligonucleotide Removal A04040H had shown very potent activity in suppressing hCD39 expression on mRNA- and protein-level in human cancer cell lines. In the next step, its activity in primary human T cells was investigated. Furthermore, the persistence of the effects after antisense oligonucleotide removal was examined. Therefore, CD8$^+$ and CD4$^+$ T cells were isolated from peripheral blood and activated for a total treatment time of six days with anti-CD3 in the presence of 10 µM of the hCD39 specific antisense oligonucleotide A04040H (black column) or the control oligonucleotide S6 (white column), which is not complementary to any human mRNA. Control cells were activated with anti-CD3 but did not receive any oligonucleotide treatment (striped column). Thereafter, oligonucleotides were removed and hCD39 protein expression was analyzed three, six, and eleven days after oligonucleotide removal by flow cytometry (FIG. 9).

As depicted in FIG. 9, A04040H significantly suppressed hCD39 protein expression for a duration of at least six days after removal of the antisense oligonucleotide, whereas treatment with S6 had no inhibitory effect on hCD39 protein expression when compared to untreated control cells. A general reduction of hCD39 protein expression was observed on CD8$^+$ and CD4$^+$ T cells at later time points (day 6 and day 11) which was most likely due to reduced T cell activation after removal of anti-CD3 from cell culture. Therefore, the difference in hCD39 protein expression levels between CD39 antisense oligonucleotide- and control oligonucleotide-treated T cells was strongest at day 3 after ASO removal. It was still significant 6 days after oligonucleotide removal (FIG. 9). 11 days after oligonucleotide removal, hCD39 expression on CD8$^+$ and CD4$^+$ T cells was low and comparable between CD39 ASO, control ASO, and untreated control cells (FIG. 9).

Example 10: Downstream Effect of hCD39 Knockdown on ATP Degradation in JIYOYE Cells Adenosine is one major immunosuppressive molecule generated during ATP degradation by hCD39. ATP can be detected by an ATP Bioluminescence Assay (ATP Bioluminescence Assay Kit CLS II; Roche). JIYOYE cells were treated with 5 µM antisense oligonucleotide A04040H (SEQ ID No. 3) or the negative control oligonucleotide neg1 for 6 days (3+3). After 3 days, RPMI-1640 medium was replaced with fresh RPMI-1640 medium containing 5 µM of oligonucleotide. Protein knockdown efficacy (FIG. 10A) and viability (FIG. 10B) were analyzed after 6 days by flow cytometry. The presence of antisense oligonucleotides did not affect cell viability (FIG. 10B). The same day, cells that were not treated with any antisense oligonucleotide were incubated for 1 hr at 37° C. with 20 µM of the CD39 small molecular inhibitor ARL67156 trisodium salt (TOCRIS). Then, 2 µM of ATP was added to cells or cell culture medium without cells derived from each condition and ATP concentration was measured in the cell supernatants or in cell culture medium after 30 min. Strikingly, ATP degradation efficacy was nearly abolished in JIYOYE cells treated with A04040H (SEQ ID No. 3) (FIG. 10C) resulting in about 4×higher ATP concentrations compared to cells treated with neg 1 and resulting in 2×higher ATP concentrations compared to cells treated with ARL67156 (FIG. 10C). Table 14 presents the effect of hCD39 knockdown on relative ATP levels in the cell culture supernatants of JIYOYE cells:

TABLE 14

Determination of ATP concentration in supernatants of JIYOYE cells after hCD39 protein knockdown and after addition of exogenous ATP to the cells

| Treatment | Relative ATP levels in supernatants of JIYOYE cells 30 minutes after addition of ATP (vs. Medium control) |
|---|---|
| No ASO | 0 |
| A04040H | 0.76 |
| neg 1 | 0.19 |
| ARL67156 | 0.38 |
| Medium (without cells) | 1 |
| Medium + ARL (no cells) | 0.94 |

Additionally, the effect of hCD39 knockdown on ATP degradation was also analyzed in primary human CD8$^+$ T cells (FIG. 11A-11D). Activated T cells were treated with 5 µM antisense oligonucleotide A04040H (SEQ ID No. 3) or the negative control oligonucleotide neg1 for 6 days (3+3). After 3 days, RPMI-1640 medium was replaced with fresh RPMI-1640 medium containing 504 of antisense oligonucleotide. Protein knockdown efficacy (FIG. 11A) and viability (FIG. 11B) were analyzed after 6 days by flow cytometry. The presence of antisense oligonucleotides did not affect cell viability (FIG. 11B). On day 6, cells were re-plated at a constant cell number and ATP was added at concentrations of 2 µM (FIG. 11C) or 20 µM (FIG. 11D). ATP concentration was measured in the cell supernatants or in cell culture medium after 30 min (Table 15).

Strikingly, ATP degradation efficacy was nearly abolished in CD8+ T cells treated with A04040H (SEQ ID No. 3) (FIG. 11C-11D) resulting in about 7×higher ATP concentrations when compared to neg 1 treated cells and almost reached the same ATP concentration as the medium control. Table 15 presents the effect of hCD39 knockdown on ATP concentration in primary human CD8+ T cells.

TABLE 15

Determination of ATP concentration in supernatants of CD8+ T cells after hCD39 protein knockdown and after addition of exogenous ATP to the cells

| ASO | Relative ATP levels in supernatants of CD8+ T cells 30 minutes after addition of ATP | |
|---|---|---|
| | Added ATP (2 µmol/l) | Added ATP (20 µmol/l) |
| No ASO | 0 | 0.37 |
| neg 1 | 0 | 0.12 |
| A04040H | 0.59 | 0.89 |
| Medium | 1 | 1 |

Example 11: Investigation of the Effect of CD39-Specific Antisense Oligonucleotide on T Cell Proliferation in the Presence or Absence of Extracellular ATP The previous results in the present invention revealed that treatment of primary human CD8+ T cells with A04040H significantly inhibits the capacity to degrade extracellular ATP. In cancer, ATP is released from tumor cells for example after cell death induced by chemotherapy or radiation therapy. Since the CD39-CD73 axis plays an important role for T cell function the effects of A04040H on T cell proliferation in the presence or absence of extracellular ATP were investigated. Human CD8+ T cells were labelled with cell proliferation dye, activated with anti-CD3 and treated with 5 µM of the antisense oligonucleotide A04040H or the control oligonucleotide S6 for a total treatment time of 5 days. In the vehicle control, cells were activated with anti-CD3 only. Subsequently, 400 µM of ATP or vehicle were added to cells on day 3 and day 4 after start of oligonucleotide treatment. Furthermore, as additional control, the small molecular CD39-inhibitor ARL67156 trisodium salt was added at 20 µM to cells on day 4 for an incubation time of 24 h. On day 5 after start of oligonucleotide treatment, CD39 protein expression, proliferation, and absolute cell numbers of CD8+ T cells were analyzed using Flow Cytometry.

Figure 12A:
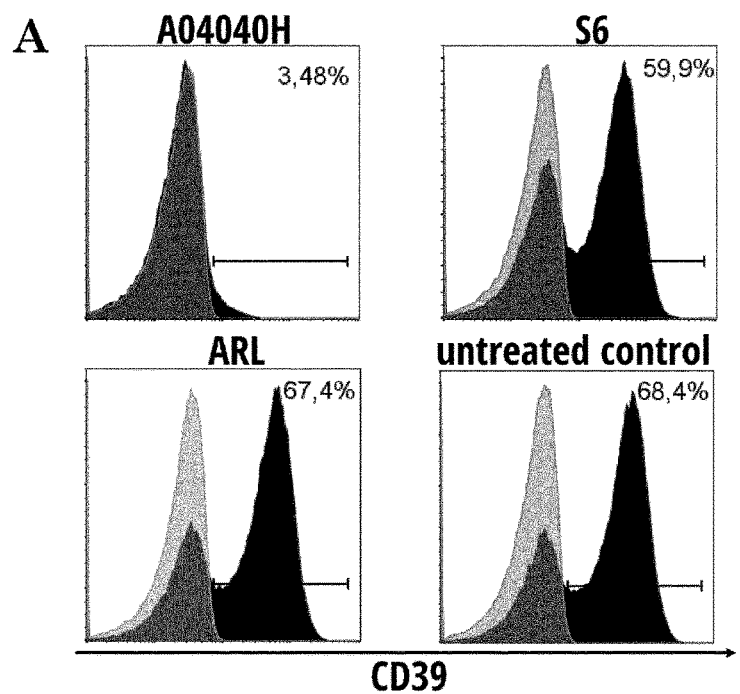
FIG. 12A-12C depict human $CD8^+$ T cells which were labelled with cell proliferation dye, activated with anti-CD3 and treated with 5 μM of the antisense oligonucleotide A04040H (black column) or the control oligonucleotide S6 (white column) for a total treatment time of 5 days. In the vehicle control (striped column), cells were activated with anti-CD3 only. Subsequently, 400 μM of ATP or vehicle were added to cells on day 3 and day 4 after start of oligonucleotide treatment. Furthermore, as additional control, the small molecular CD39-inhibitor ARL67156 trisodium salt was added at 20 μM to cells on day 4, for an incubation time of 24 h (checked column). On day 5 after start of oligonucleotide treatment, (FIG. 12A) CD39 protein expression, (FIG. 12B) proliferation and (FIG. 12C) absolute cell numbers of CD8+ T cells were analyzed using Flow Cytometry. Depicted is the mean of triplicate wells+/−SD.
Figure 12B:
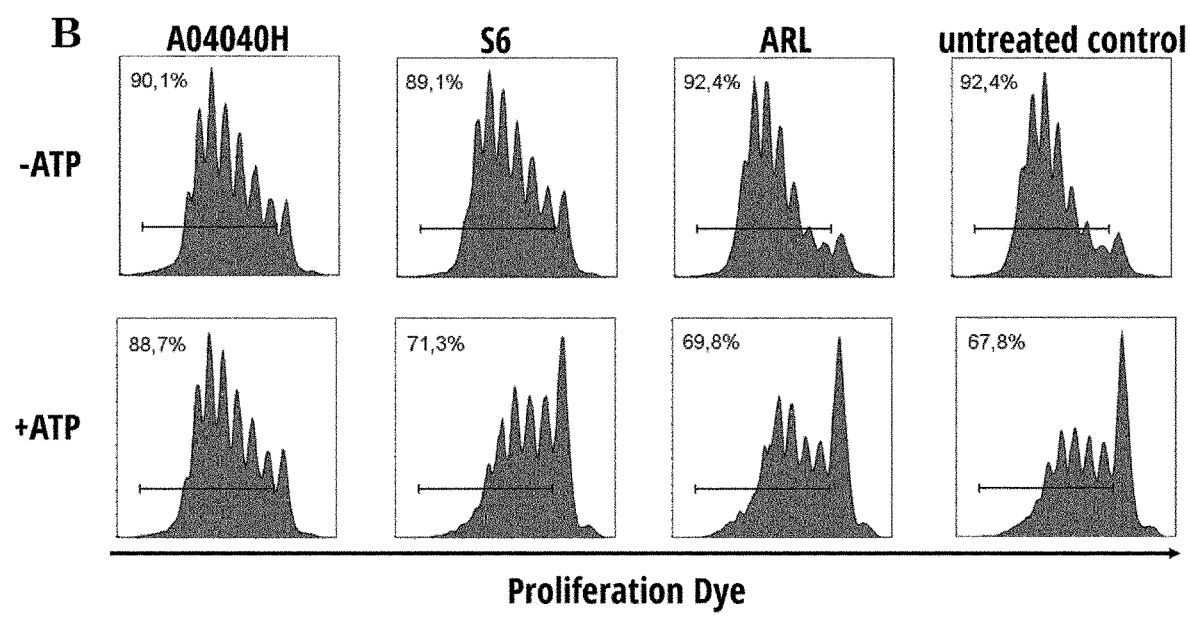
Figure 12C:
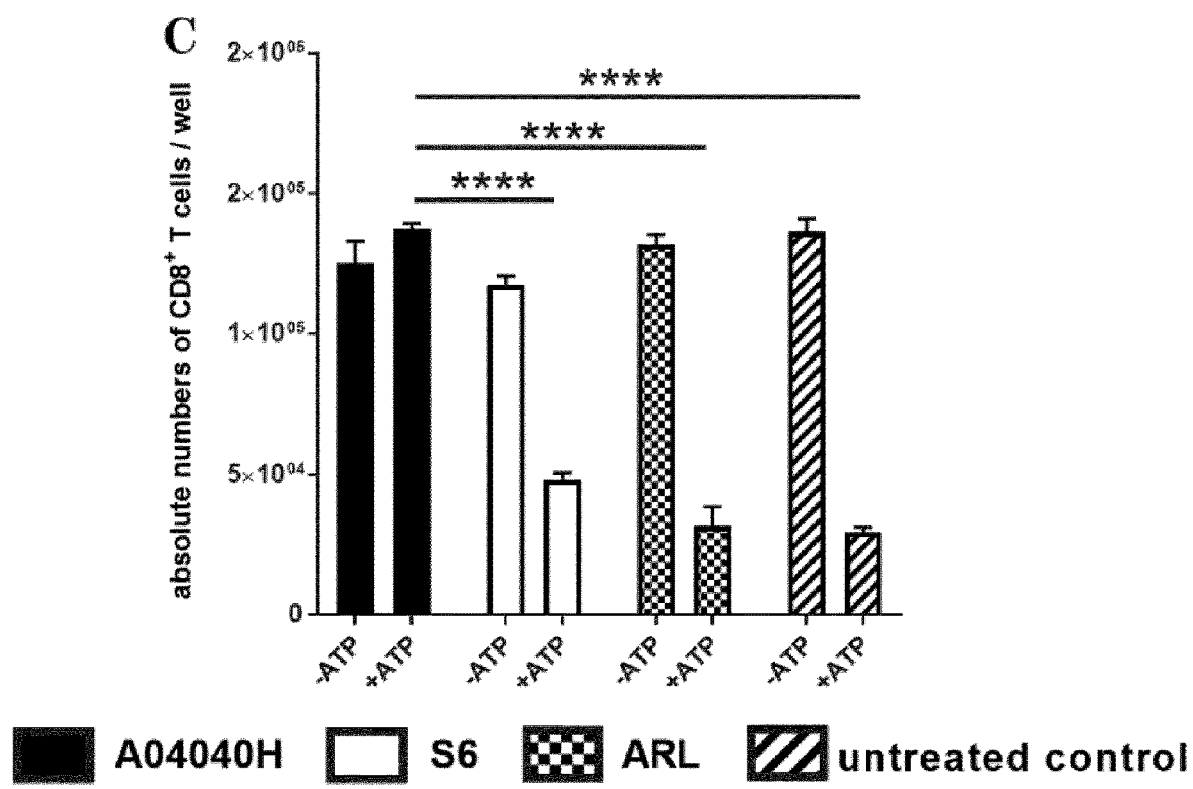

A04040H treatment of CD8+ T cells potently suppressed CD39 protein expression (FIG. 12A). In the absence of extracellular ATP, no differences in proliferation (FIG. 12B upper panel), or absolute cell numbers (FIG. 12C) were observed between A04040H—(black column), S6—(white column), ARL67156—(checked column), and vehicle-treated (striped column) CD8+ T cells. Supplementation with 400 µM of ATP reduced proliferation (FIG. 12B lower panel) and significantly diminished absolute numbers (FIG. 12C) of CD8+ T cells treated with S6, ARL67156, or vehicle. Strikingly, proliferation (FIG. 12B lower panel) of A04040H treated CD8+ T cells was not reduced by supplementation of cell culture medium with ATP. Accordingly, absolute T cell numbers (FIG. 12C) were not altered by ATP-supplementation in A04040H-treated cells.

In summary, these results revealed that supplementation of cell culture medium with ATP significantly impaired proliferation of CD39 expressing CD8+ T cells. Strikingly, CD39-protein knockdown by A04040H treatment inhibited ATP degradation and therefore reversed the inhibitory effects of supplemented ATP on cell proliferation and absolute T cell numbers.

Example 12: Design of Mouse/Rat CD39 Antisense Oligonucleotides

Due to the sequence differences between human and mouse(m)/rat(r) CD39 only few hCD39 antisense oligonucleotides are cross-reactive to mouse/rat CD39. As they showed only limited knockdown efficacy in human cell lines, surrogate antisense oligonucleotides were designed with specificity for mouse/rat CD39. The mouse CD39 mRNA sequence with SEQ ID No. 2 (seq. ref. NM_001304721.1) was used as basis for the design of 15, 16 and 17 mer antisense oligonucleotides, neg1 is described in WO2014154843 A1 and served as control in all experiments (Table 2). The distribution of the antisense oligonucleotide binding sites on the hCD39 mRNA is shown in FIG. 13.

Figures 1, 14:
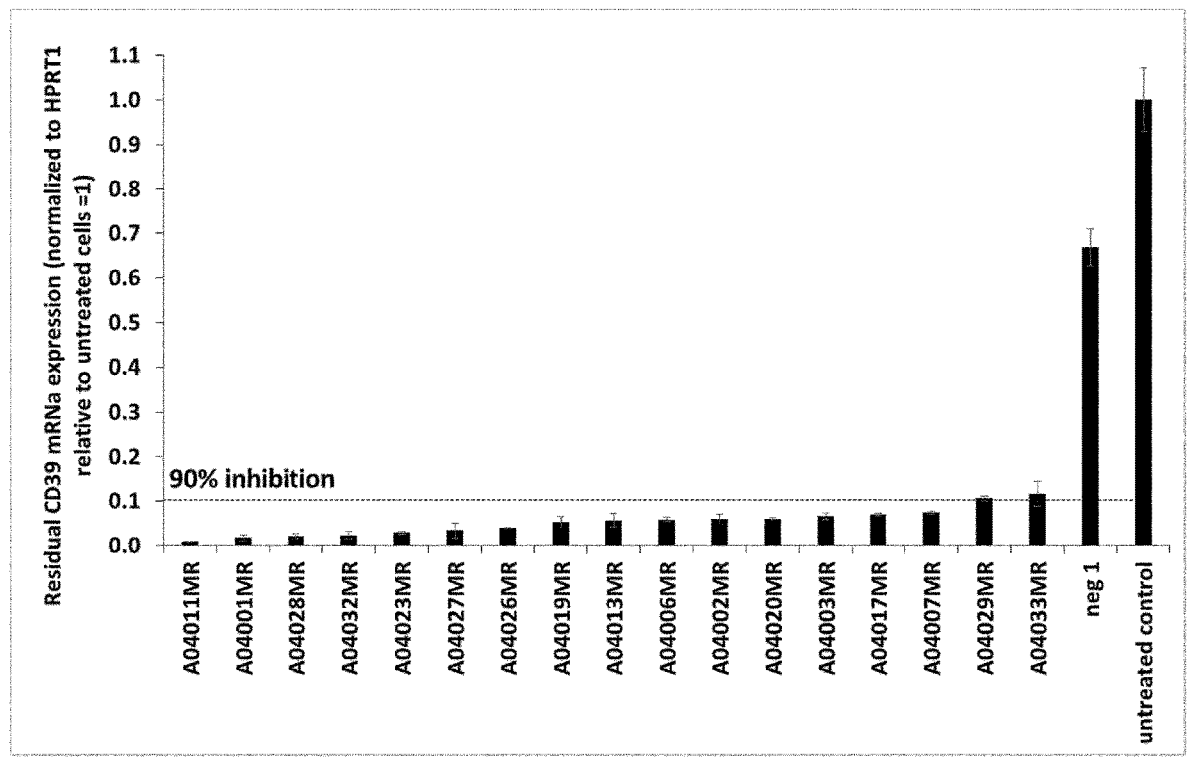
Figures 2, 14:
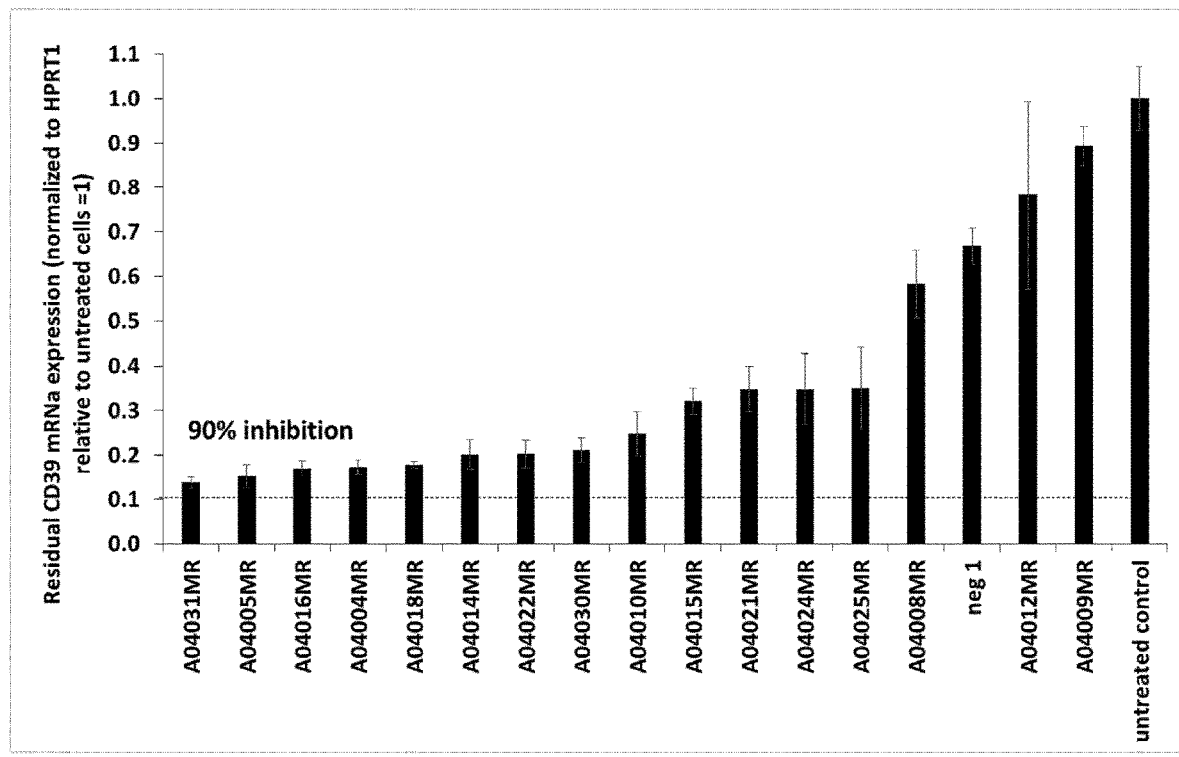

Example 13: Efficacy Screen of mCD39 Antisense Oligonucleotides in Murine Cancer Cell Lines In order to analyze the efficacy of mCD39 antisense oligonucleotides with regard to the knockdown of mCD39 mRNA expression in a cancer cell line, A20 (mouse B cell lymphoma, ATCC) cells were treated with a single dose (concentration: 10 µM without addition of any transfection reagent; this process is called gymnotic delivery) of the respective antisense oligonucleotide as indicated in FIG. 14. As control, cells were treated with neg1, an antisense oligonucleotide having the sequence CGTTTAGGC-TATGTACTT (SEQ ID NO:99). mCD39 and HPRT1 mRNA expression was analyzed after three days using the QuantiGene Singleplex assay (Affymetrix) and mCD39 expression values were normalized to HPRT1 expression values. Strikingly, as shown in FIG. 14, treatment with 15 different antisense oligonucleotides resulted in a knockdown efficacy of >90% in A20 cells. Exact values of the mean normalized mRNA expression of mCD39 are given in the following Table 16:

TABLE 16

List of mean normalized mCD39 mRNA expression values in antisense oligonucleotide treated A20 cells compared to untreated cells.

| ASO | Relative mCD39 mRNA expression (compared to non-treated cells) |
|---|---|
| A04011MR | 0.01 |
| A04001MR | 0.02 |
| A04028MR | 0.02 |
| A04032MR | 0.02 |
| A04023MR | 0.03 |
| A04027MR | 0.03 |
| A04026MR | 0.04 |
| A04019MR | 0.05 |
| A04013MR | 0.06 |
| A04006MR | 0.06 |
| A04002MR | 0.06 |
| A04020MR | 0.06 |

TABLE 16-continued

List of mean normalized mCD39 mRNA expression values in antisense oligonucleotide treated A20 cells compared to untreated cells.

| ASO | Relative mCD39 mRNA expression (compared to non-treated cells) |
|---|---|
| A04003MR | 0.07 |
| A04017MR | 0.07 |
| A04007MR | 0.07 |
| A04029MR | 0.11 |
| A04033MR | 0.12 |
| A04031MR | 0.14 |
| A04005MR | 0.15 |
| A04016MR | 0.17 |
| A04004MR | 0.17 |
| A04018MR | 0.18 |
| A04014MR | 0.20 |
| A04022MR | 0.20 |
| A04030MR | 0.21 |
| A04010MR | 0.25 |
| A04015MR | 0.32 |
| A04021MR | 0.35 |
| A04024MR | 0.35 |
| A04025MR | 0.35 |
| A04008MR | 0.58 |
| neg1 | 0.67 |
| A04012MR | 0.78 |
| A04009MR | 0.89 |

Example 14: Antisense Oligonucleotide-Mediated In Vivo mCD39 mRNA Knockdown in C57BL/6 Mice The potent mCD39 ASO A04011MR was selected and its in vivo knockdown capacity in C57BL/6 mice was analyzed. C57BL/6 mice were treated by subcutaneous injections of either A04011MR or the negative control oligonucleotide neg1 at doses of 25 mg/kg or 10 mg/kg on days 1, 2, 3, 4, 5, 9, 12, 16, and 19 (5 mice/group). Seven days after the last ASO treatment (day 26), mice were sacrificed and spleens were sampled for CD39 mRNA analysis. The results depicted in FIG. 15 show CD39 mRNA expression levels in spleens of A04011MR or neg1-treated mice. Strikingly, mCD39 mRNA levels were significantly reduced in spleens upon systemic treatment of mice with 25 mg/kg (FIG. 15A) or 10 mg/kg (FIG. 15B) of A04011MR when compared to control oligonucleotide (neg 1) treated mice. These data clearly indicate that A04011MR potently inhibits CD39 expression on mRNA level in spleens in vivo.

Example 15: Antisense Oligonucleotide-Mediated In Vivo mCD39 Protein Knockdown in a Syngeneic Mouse Tumor Model The potent mCD39 antisense oligonucleotide A04011MR was selected and its in vivo knockdown capacity in a subcutaneous syngeneic murine tumor model was analyzed. Therefore, $5 \times 10^5$ MC38 wt tumor cells were injected subcutaneously into C57BL/6 mice. Once tumors reached sizes between 50-70 mm$^3$, mice were treated systemically by subcutaneous injections with different doses of A04011MR (20 mg/kg; 10 mg/kg; 5 mg/kg) or with the negative control oligonucleotide neg1 (20 mg/kg) on days 1, 2, 3, 4, 5, 9, and 12 (4 mice/per group). As additional control, MC-38 tumor-bearing mice were left untreated. Four days after the last treatment with antisense oligonucleotide (day 16), tumors were isolated in order to analyze CD39 protein expression in subtypes of tumor-infiltrating immune cells using flow cytometry. FIGS. 16A and 16B depict CD39 protein expression on tumor-infiltrating regulatory T cells ($T_{regs}$) (FIG. 16A) and tumor associated macrophages (TAMs) (FIG. 16B) from oligonucleotide-treated mice in relation to tumors of untreated mice. Strikingly, A04011MR dose-dependently suppressed mCD39 protein expression on $T_{regs}$ (FIG. 16A) and TAMs (FIG. 16B) with the highest efficacy at 20 mg/kg when compared to the controls. These data clearly indicate that A04011MR potently inhibits CD39 expression on protein level in tumor infiltrating immune cells in vivo.

A sequence listing is provided as an ASCII text file named "Substitute-Sequence-Listing-14Dec2020-20885-2101" created on 13 Dec. 2020 and having a size of 34727 bytes. The ASCII text file is hereby incorporated by reference in the application.

The invention claimed is:

1. An oligonucleotide capable of hybridizing with a nucleic acid sequence of the ectonucleotidase (NTPdase) CD39 of SEQ ID NO.1 (human) consisting of a sequence selected from the group consisting of SEQ ID NO. 89, SEQ ID NO.91, SEQ ID NO.3, SEQ ID NO.4, SEQ ID NO.97, SEQ ID NO.93, SEQ ID NO.94, SEQ ID NO.23, SEQ ID NO.7, SEQ ID NO.8, SEQ ID NO.9, SEQ ID NO.10, SEQ ID NO.11, SEQ ID NO.12, SEQ ID NO.13, SEQ ID NO.14, SEQ ID NO.15, SEQ ID NO.16, SEQ ID NO.17, SEQ ID NO.18, SEQ ID NO.19, SEQ ID NO.20, SEQ ID NO.21, SEQ ID NO.22, SEQ ID NO.24, SEQ ID NO.25, SEQ ID NO.26, SEQ ID NO.27, SEQ ID NO.28, SEQ ID NO.29, SEQ ID NO.30, SEQ ID NO.31, SEQ ID NO.32, SEQ ID NO.33, SEQ ID NO.34, SEQ ID NO.35, SEQ ID NO.36, SEQ ID NO.37, SEQ ID NO.38, SEQ ID NO.39, SEQ ID NO.40, SEQ ID NO.41, SEQ ID NO.42, SEQ ID NO.43, SEQ ID NO.44, SEQ ID NO.45, SEQ ID NO.46, SEQ ID NO.47, SEQ ID NO.48, SEQ ID NO.49, SEQ ID NO.50, SEQ ID NO.51, SEQ ID NO.52, SEQ ID NO.88, SEQ ID NO.90, SEQ ID NO.92, SEQ ID NO.95, SEQ ID NO.96 and combinations thereof, wherein at least one nucleotide of the oligonucleotide is LNA modified.

2. The oligonucleotide of claim 1, wherein the oligonucleotide is selected from the group consisting of

```
                                    (A04053H, SEQ ID NO: 89)
+T*+A*+C*G*T*T*C*A*C*T*A*C*C*T*+T*C*+T, (A04052H, SEQ ID NO: 89)
+T*+A*+C*G*T*T*C*A*C*T*A*C*C*T*+T*+C*+T, (A04055H, SEQ ID NO: 91)
+T*+A*+G*T*A*A*G*C*C*C*T*G*+A*+T*+G,
```

```
                                (A04040H, SEQ ID NO: 3)
+G*+T*+T*T*G*T*G*T*G*A*G*A*G*C*+T*+T, (A04045H, SEQ ID NO: 4)
+C*+A*+C*T*T*A*C*G*T*T*C*A*C*T*+A*+C*+C, (A04062H, SEQ ID NO: 97)
+G*G*+T*T*T*G*T*G*T*G*A*G*+A*G*+C, (A04059H, SEQ ID NO: 94)
+G*+G*+T*T*T*G*T*G*T*G*A*G*A*G*C*+T*+T, (A04060H, SEQ ID NO: 95)
+G*+G*+T*T*T*G*T*G*T*G*A*G*A*G*C*+T, (A04019H, SEQ ID NO: 23)
+G*+T*+A*A*G*C*C*C*T*G*A*T*+G*+T*+T, (A04003H, SEQ ID NO: 7)
+T*+T*+G*A*A*C*A*C*T*G*C*+G*+A*+T, (A04004H, SEQ ID NO: 8)
+G*+C*+A*T*A*G*G*C*A*C*C*+T*+T*+C, (A04005H, SEQ ID NO: 9)
+C*+T*+A*T*G*C*T*G*A*A*C*C*+A*+C*+C, (A04006H, SEQ ID NO: 10)
+T*G*+T*A*G*A*G*G*C*T*C*C*C*+C*+C, (A04007H, SEQ ID NO: 11)
+T*+T*+G*C*A*G*A*G*C*A*T*T*+A*+T*+C, (A04008H, SEQ ID NO: 12)
+A*+G*+G*C*G*A*A*A*T*T*G*C*+A*+G*+A, (A04009H, SEQ ID NO: 13)
+T*+A*G*A*C*A*T*T*G*T*A*G*+T*+C*+C, (A04010H, SEQ ID NO: 14)
+G*+A*G*T*G*C*C*T*G*A*T*C*C*+T*+T, (A04011H, SEQ ID NO: 15)
+A*+A*+T*C*C*C*C*T*G*G*A*+G*+T*+G, (A04012H, SEQ ID NO: 16)
+A*+G*+C*G*T*A*A*G*A*T*G*T*+T*+T*+T, (A04013H, SEQ ID NO: 17)
+A*+C*+T*C*C*A*G*C*G*T*A*A*+G*+A*+T, (A04014H, SEQ ID NO: 18)
+T*+G*+A*T*A*G*C*C*T*T*G*C*+A*+G*+A, (A04015H, SEQ ID NO: 19)
+A*+G*T*C*C*A*G*C*C*G*G*C*G*T*+C, (A04016H, SEQ ID NO: 20)
+G*G*+A*C*A*A*T*G*G*T*T*G*+C*+T*+C, (A04017H, SEQ ID NO: 21)
+C*+T*+T*G*A*A*C*A*C*T*G*C*+G*+A*+T, (A04018H, SEQ ID NO: 22)
+G*+A*G*T*A*C*A*A*C*T*G*A*+A*+C*+C, (A04020H, SEQ ID NO: 24)
+T*+A*+T*G*G*T*A*C*A*G*T*+T*G*+G*+T, (A04021HM, SEQ ID NO: 25)
+C*+T*+G*A*C*T*G*A*A*T*T*T*G*+C*+C*+C, (A04022HM, SEQ ID NO: 26)
+A*+C*+T*A*T*G*C*T*G*A*A*C*C*A*+C*+C, (A04023HM, SEQ ID NO: 27)
+G*+A*C*T*A*T*G*C*T*G*A*A*C*+C*+A*+C, (A04024HM, SEQ ID NO: 28)
+G*+A*+G*G*C*G*A*A*A*T*T*G*C*+A*+G*+A, (A04025H, SEQ ID NO: 29)
+A*+G*A*G*T*G*C*C*T*G*A*T*C*C*+T*+T, (A04026H, SEQ ID NO: 30)
+G*+A*+T*A*G*T*T*T*C*C*A*A*T*+A*+C*+C, (A04027H, SEQ ID NO: 31)
+T*+A*+C*T*C*C*A*G*C*G*T*A*A*+G*+A*+T, (A04028H, SEQ ID NO: 32)
+A*+T*+G*T*A*G*C*C*C*A*A*A*G*+T*+C*+C, (A04029H, SEQ ID NO: 33)
+C*+A*+T*G*T*A*G*C*C*C*A*A*A*+G*+T*+C, (A04030H, SEQ ID NO: 34)
+G*+G*+A*C*A*A*T*G*G*T*T*G*C*+T*+C*+A, (A04031H, SEQ ID NO: 35)
+A*+G*+C*C*T*A*A*T*G*A*T*G*G*C*C*+A*+C, (A04032H, SEQ ID NO: 36)
+G*+C*+C*T*T*G*A*A*C*A*C*T*G*C*+G*+A, (A04033H, SEQ ID NO: 37)
+A*+C*C*C*T*G*A*G*T*T*G*T*A*A*C*+T, (A04034H, SEQ ID NO: 38)
+A*+G*G*A*T*A*G*T*C*T*T*G*T*C*+T*+C, (A04035H, SEQ ID NO: 39)
+C*C*T*A*C*C*C*A*G*G*A*T*A*G*+T*+C, (A04036H, SEQ ID NO: 40)
+C*+C*+C*T*C*T*C*A*C*T*A*A*A*+T*+T*+A, (A04037H, SEQ ID NO: 41)
+A*+C*+T*C*C*A*C*A*C*T*A*A*T*G*+C*+T, (A04038H, SEQ ID NO: 42)
+G*T*+C*A*A*T*C*C*T*G*C*T*C*A*+A*+C, (A04039H, SEQ ID NO: 43)
+C*+A*+G*T*C*A*A*T*C*C*T*G*C*+T*+C*+A, (A04041HM, SEQ ID NO: 44)
+C*T*+T*G*C*C*A*T*A*G*A*G*G*C*+G*+A*+A, (A04042H, SEQ ID NO: 45)
+T*+G*+C*C*A*G*A*G*T*G*C*C*T*G*+A*+T*+C, (A04043H, SEQ ID NO: 46)
+A*+C*+G*T*T*C*A*C*T*A*C*C*T*T*+C*+T*+T, (A04044H, SEQ ID NO: 47)
+T*+T*+A*C*G*T*T*C*A*C*T*A*C*C*+T*+T*+C, (A04046H, SEQ ID NO: 48)
+A*+A*+G*G*T*C*A*C*T*T*A*C*G*T*+T*+C*+A, (A04047H, SEQ ID NO: 49)
+G*+C*+C*C*C*A*A*A*A*T*C*C*C*C*+C*+T*+G, (A04048H, SEQ ID NO: 50)
+G*+A*+G*A*G*A*A*T*G*T*A*G*G*T*+A*C*+C, (A04049H, SEQ ID NO: 51)
+C*+C*C*T*G*G*A*T*C*T*T*G*C*C*+A*+A*+T, (A04050H, SEQ ID NO: 52)
+A*+A*+A*G*T*C*C*A*G*C*C*G*G*C*G*+T*+C, (A04051H, SEQ ID NO: 88)
+A*+G*+A*G*T*G*C*C*T*G*A*T*C*+C*+T*+T, (A04054H, SEQ ID NO: 90)
+G*+C*+C*C*T*G*A*T*G*T*T*T*G*+A*+A*+T, (A04056H, SEQ ID NO: 92)
+G*+T*+T*T*G*T*G*T*G*A*G*A*G*C*+T*+T,
```

-continued

```
                              (A04058H, SEQ ID NO: 93)
+T*+T*+T*G*T*G*T*G*A*G*A*G*+C*+T*+T, (A04061H, SEQ ID NO: 96)
+G*+T*+T*T*G*T*G*T*G*A*G*A*G*C*+T,
``` and combinations thereof, wherein + indicates an LNA nucleotide and * indicates a phosphorothioate (PTO) linkage between the nucleotides.

3. A pharmaceutical composition comprising an oligonucleotide of claim 1 and a pharmaceutically acceptable carrier, excipient and/or dilutant.

4. The pharmaceutical composition of claim 3, further comprising a chemotherapeutic.

5. The pharmaceutical composition of claim 4, wherein the chemotherapeutic is platinum, gemcitabine, another oligonucleotide, an antibody and/or a small molecule.

6. The pharmaceutical composition of claim 5, wherein the other oligonucleotide, the antibody and/or the small molecule inhibits or stimulates an immune suppressive factor and/or an immune stimulatory factor.

7. The pharmaceutical composition of claim 6, wherein the immune suppressive factor is selected from the group consisting of IDO1, IDO2, CTLA-4, PD-1, PD-L1, LAG-3, VISTA, A2AR, CD39, CD73, STAT3, TDO2, TIM-3, TIGIT, TGF-beta, BTLA, MICA, NKG2A, KIR, CD160, Chop, Xbp1 and a combination thereof.

8. The pharmaceutical composition of claim 6, wherein the immune stimulatory factor is selected from the group consisting of 4-1BB, Ox40, KIR, GITR, CD27, 2B4 and a combination thereof.

* * * * *

SEQUENCE LISTING

```
<160> NUMBER OF SEQ ID NOS: 99

<210> SEQ ID NO 1
<211> LENGTH: 3420
<212> TYPE: DNA
<213> ORGANISM: Homo sapiens
<220> FEATURE:
<221> NAME/KEY: CDS
<222> LOCATION: (187)..(1857)

<400> SEQUENCE: 1
agggaagaag ggagaaagag agagagattt gaatatacat tgcttcaagg atgcaaaaaa      60
ttacaacctg gaaaaggctt cgagtaactt taggaaaatg agctgctgga ctcctcagtc     120
aatctgtcct ttctagtcaa tgaaaaagac agggtttgag gttccttccg aaacggggcc     180 ggctaa ttt agc ccc tcc cac gag ccc aag ggt ctg tta tat ctc tgt        228
       Phe Ser Pro Ser His Glu Pro Lys Gly Leu Leu Tyr Leu Cys
        1               5                  10 ttc ctt gag gac ctc tct cac gga gac gga cca cag caa gca gag gct        276
Phe Leu Glu Asp Leu Ser His Gly Asp Gly Pro Gln Gln Ala Glu Ala
15                  20                  25                  30
```

-continued

```
ggg ggg ggg aaa gac gag gaa aga gga gga aaa caa aag ctg cta ctt      324
Gly Gly Gly Lys Asp Glu Glu Arg Gly Gly Lys Gln Lys Leu Leu Leu
             35                  40                  45 atg gaa gat aca aag gag tct aac gtg aag aca ttt tgc tcc aag aat      372
Met Glu Asp Thr Lys Glu Ser Asn Val Lys Thr Phe Cys Ser Lys Asn
     50                  55                  60 atc cta gcc atc ctt ggc ttc tcc tct atc ata gct gtg ata gct ttg      420
Ile Leu Ala Ile Leu Gly Phe Ser Ser Ile Ile Ala Val Ile Ala Leu
 65                  70                  75 ctt gct gtg ggg ttg acc cag aac aaa gca ttg cca gaa aac gtt aag      468
Leu Ala Val Gly Leu Thr Gln Asn Lys Ala Leu Pro Glu Asn Val Lys
         80                  85                  90 tat ggg att gtg ctg gat gcg ggt tct tct cac aca agt tta tac atc      516
Tyr Gly Ile Val Leu Asp Ala Gly Ser Ser His Thr Ser Leu Tyr Ile
 95                 100                 105                 110 tat aag tgg cca gca gaa aag gag aat gac aca ggc gtg gtg cat caa      564
Tyr Lys Trp Pro Ala Glu Lys Glu Asn Asp Thr Gly Val Val His Gln
                115                 120                 125 gta gaa gaa tgc agg gtt aaa ggt cct gga atc tca aaa ttt gtt cag      612
Val Glu Glu Cys Arg Val Lys Gly Pro Gly Ile Ser Lys Phe Val Gln
            130                 135                 140 aaa gta aat gaa ata ggc att tac ctg act gat tgc atg gaa aga gct      660
Lys Val Asn Glu Ile Gly Ile Tyr Leu Thr Asp Cys Met Glu Arg Ala
        145                 150                 155 agg gaa gtg att cca agg tcc cag cac caa gag aca ccc gtt tac ctg      708
Arg Glu Val Ile Pro Arg Ser Gln His Gln Glu Thr Pro Val Tyr Leu
    160                 165                 170 gga gcc acg gca ggc atg cgg ttg ctc agg atg gaa agt gaa gag ttg      756
Gly Ala Thr Ala Gly Met Arg Leu Leu Arg Met Glu Ser Glu Glu Leu
175                 180                 185                 190 gca gac agg gtt ctg gat gtg gtg gag agg agc ctc agc aac tac ccc      804
Ala Asp Arg Val Leu Asp Val Val Glu Arg Ser Leu Ser Asn Tyr Pro
                195                 200                 205 ttt gac ttc cag ggt gcc agg atc att act ggc caa gag gaa ggt gcc      852
Phe Asp Phe Gln Gly Ala Arg Ile Ile Thr Gly Gln Glu Glu Gly Ala
            210                 215                 220 tat ggc tgg att act atc aac tat ctg ctg ggc aaa ttc agt cag aaa      900
Tyr Gly Trp Ile Thr Ile Asn Tyr Leu Leu Gly Lys Phe Ser Gln Lys
        225                 230                 235 aca agg tgg ttc agc ata gtc cca tat gaa acc aat aat cag gaa acc      948
Thr Arg Trp Phe Ser Ile Val Pro Tyr Glu Thr Asn Asn Gln Glu Thr
    240                 245                 250 ttt gga gct ttg gac ctt ggg gga gcc tct aca caa gtc act ttt gta      996
Phe Gly Ala Leu Asp Leu Gly Gly Ala Ser Thr Gln Val Thr Phe Val
255                 260                 265                 270 ccc caa aac cag act atc gag tcc cca gat aat gct ctg caa ttt cgc     1044
Pro Gln Asn Gln Thr Ile Glu Ser Pro Asp Asn Ala Leu Gln Phe Arg
                275                 280                 285 ctc tat ggc aag gac tac aat gtc tac aca cat agc ttc ttg tgc tat     1092
Leu Tyr Gly Lys Asp Tyr Asn Val Tyr Thr His Ser Phe Leu Cys Tyr
            290                 295                 300 ggg aag gat cag gca ctc tgg cag aaa ctg gcc aag gac att cag gtt     1140
Gly Lys Asp Gln Ala Leu Trp Gln Lys Leu Ala Lys Asp Ile Gln Val
        305                 310                 315 gca agt aat gaa att ctc agg gac cca tgc ttt cat cct gga tat aag     1188
Ala Ser Asn Glu Ile Leu Arg Asp Pro Cys Phe His Pro Gly Tyr Lys
    320                 325                 330 aag gta gtg aac gta agt gac ctt tac aag acc ccc tgc acc aag aga     1236
Lys Val Val Asn Val Ser Asp Leu Tyr Lys Thr Pro Cys Thr Lys Arg
335                 340                 345                 350
```

-continued

| | | |
|---|---|---|
| ttt gag atg act ctt cca ttc cag cag ttt gaa atc cag ggt att gga<br>Phe Glu Met Thr Leu Pro Phe Gln Gln Phe Glu Ile Gln Gly Ile Gly<br>355                                  360                        365 | 1284 |

```
ttt gag atg act ctt cca ttc cag cag ttt gaa atc cag ggt att gga    1284
Phe Glu Met Thr Leu Pro Phe Gln Gln Phe Glu Ile Gln Gly Ile Gly
            355                 360                 365 aac tat caa caa tgc cat caa agc atc ctg gag ctc ttc aac acc agt    1332
Asn Tyr Gln Gln Cys His Gln Ser Ile Leu Glu Leu Phe Asn Thr Ser
        370                 375                 380 tac tgc cct tac tcc cag tgt gcc ttc aat ggg att ttc ttg cca cca    1380
Tyr Cys Pro Tyr Ser Gln Cys Ala Phe Asn Gly Ile Phe Leu Pro Pro
    385                 390                 395 ctc cag ggg gat ttt ggg gca ttt tca gct ttt tac ttt gtg atg aag    1428
Leu Gln Gly Asp Phe Gly Ala Phe Ser Ala Phe Tyr Phe Val Met Lys
400                 405                 410 ttt tta aac ttg aca tca gag aaa gtc tct cag gaa aag gtg act gag    1476
Phe Leu Asn Leu Thr Ser Glu Lys Val Ser Gln Glu Lys Val Thr Glu
415                 420                 425                 430 atg atg aaa aag ttc tgt gct cag cct tgg gag gag ata aaa aca tct    1524
Met Met Lys Lys Phe Cys Ala Gln Pro Trp Glu Glu Ile Lys Thr Ser
                435                 440                 445 tac gct gga gta aag gag aag tac ctg agt gaa tac tgc ttt tct ggt    1572
Tyr Ala Gly Val Lys Glu Lys Tyr Leu Ser Glu Tyr Cys Phe Ser Gly
            450                 455                 460 acc tac att ctc tcc ctc ctt ctg caa ggc tat cat ttc aca gct gat    1620
Thr Tyr Ile Leu Ser Leu Leu Leu Gln Gly Tyr His Phe Thr Ala Asp
        465                 470                 475 tcc tgg gag cac atc cat ttc att ggc aag atc cag ggc agc gac gcc    1668
Ser Trp Glu His Ile His Phe Ile Gly Lys Ile Gln Gly Ser Asp Ala
    480                 485                 490 ggc tgg act ttg ggc tac atg ctg aac ctg acc aac atg atc cca gct    1716
Gly Trp Thr Leu Gly Tyr Met Leu Asn Leu Thr Asn Met Ile Pro Ala
495                 500                 505                 510 gag caa cca ttg tcc aca cct ctc tcc cac tcc acc tat gtc ttc ctc    1764
Glu Gln Pro Leu Ser Thr Pro Leu Ser His Ser Thr Tyr Val Phe Leu
                515                 520                 525 atg gtt cta ttc tcc ctg gtc ctt ttc aca gtg gcc atc ata ggc ttg    1812
Met Val Leu Phe Ser Leu Val Leu Phe Thr Val Ala Ile Ile Gly Leu
            530                 535                 540 ctt atc ttt cac aag cct tca tat ttc tgg aaa gat atg gta tag       1857
Leu Ile Phe His Lys Pro Ser Tyr Phe Trp Lys Asp Met Val
        545                 550                 555 caaaagcagc tgaaatatgc tggctggagt gaggaaaaaa atcgtccagg gagcattttc   1917
ctccatcgca gtgttcaagg ccatccttcc ctgtctgcca gggccagtct tgacgagtgt   1977
gaagcttcct tggcttttac tgaagccttt cttttggagg tattcaatat cctttgcctc   2037
aaggacttcg gcagatactg tctctttcat gagttttttcc cagctacacc tttctccttt   2097
gtactttgtg cttgtatagg ttttaaagac ctgacacctt tcataatctt tgctttataa   2157
aagaacaata ttgactttgt ctagaagaac tgagagtctt gagtcctgtg ataggaggct   2217
gagctggcta aaagaagaat ctcaggaact ggttcagttg tactctttaa gaacccctttt   2277 ctctctcctg tttgccatcc attaagaaag ccatatgatg cctttggaga aggcagacac   2337
acattccatt cccagcctgc tctgtgggta ggagaatttt ctacagtagg caaatatgtg   2397
ctaaagccaa agagttttat aaggaaatat atgtgctcat gcagtcaata cagttctcaa   2457
tcccacccaa agcaggtatg tcaataaatc acatattcct aggtgatacc caaatgctac   2517
agagtggaac actcagacct gagatttgca aaaagcagat gtaaatatat gcattcaaac   2577
atcagggctt actatgaggt aggtggtata tacatgtcac aaataaaaat acagttacaa   2637
```

-continued

```
ctcagggtca caaaaaatgc atcttccaat gcatattttt attatggtaa aatatacata    2697
aatataattc accattttaa catttaattc atattaaata cgtacaaatc agtgacattt    2757
agtacattca cagtgttgtg ccaccatcac cactatttag ttccagaaca tttgcatcat    2817
caatacattg tctagagaca agactatcct gggtaggcag aaaccataga tcttttgtgt    2877
ttacagctat ggaaaccaac tgtaccataa agatagttca ctgagttta aagccaagcc     2937 acatcttatt tttccaaggt ttaatttagt gagagggcag cattagtgtg gagtggcatg    2997
cttttgccct atcgtggaat ttacacatca gaatgtgcag gatccaagtc tgaaagtgtt    3057
gccacccgtc acacaacatg ggctttgttt gcttattcca tgaagcagca gctatagacc    3117
ttaccatgga aacatgaaga gaccctgcac ccctttcctt aaggattgct gcaagagtta    3177
cctgttgagc aggattgact ggtgatgttt cattctgacc ttgtcccaag ctctccatct    3237
ctagatctgg ggactgactg ttgagctgat ggggaaagaa aagctctcac acaaaccgga    3297
agccaaatgt cccctatctc ttgaatgatc aagtcacttt tgacaacatc caggtgaata    3357
taaaaactta ataagctgt ggaaaggaac tcttaatctt cttttctgct acttaggtta    3417
aat                                                                  3420
```

<210> SEQ ID NO 2
<211> LENGTH: 556
<212> TYPE: PRT
<213> ORGANISM: Homo sapiens

<400> SEQUENCE: 2

```
Phe Ser Pro Ser His Glu Pro Lys Gly Leu Leu Tyr Leu Cys Phe Leu
1               5                   10                  15

Glu Asp Leu Ser His Gly Asp Gly Pro Gln Gln Ala Glu Ala Gly Gly
            20                  25                  30

Gly Lys Asp Glu Glu Arg Gly Gly Lys Gln Lys Leu Leu Leu Met Glu
        35                  40                  45

Asp Thr Lys Glu Ser Asn Val Lys Thr Phe Cys Ser Lys Asn Ile Leu
    50                  55                  60

Ala Ile Leu Gly Phe Ser Ser Ile Ile Ala Val Ile Ala Leu Leu Ala
65                  70                  75                  80

Val Gly Leu Thr Gln Asn Lys Ala Leu Pro Glu Asn Val Lys Tyr Gly
                85                  90                  95

Ile Val Leu Asp Ala Gly Ser Ser His Thr Ser Leu Tyr Ile Tyr Lys
            100                 105                 110

Trp Pro Ala Glu Lys Glu Asn Asp Thr Gly Val Val His Gln Val Glu
        115                 120                 125

Glu Cys Arg Val Lys Gly Pro Gly Ile Ser Lys Phe Val Gln Lys Val
    130                 135                 140

Asn Glu Ile Gly Ile Tyr Leu Thr Asp Cys Met Glu Arg Ala Arg Glu
145                 150                 155                 160

Val Ile Pro Arg Ser Gln His Gln Glu Thr Pro Val Tyr Leu Gly Ala
                165                 170                 175

Thr Ala Gly Met Arg Leu Leu Arg Met Glu Ser Glu Glu Leu Ala Asp
            180                 185                 190

Arg Val Leu Asp Val Val Glu Arg Ser Leu Ser Asn Tyr Pro Phe Asp
        195                 200                 205

Phe Gln Gly Ala Arg Ile Ile Thr Gly Gln Glu Glu Gly Ala Tyr Gly
    210                 215                 220

Trp Ile Thr Ile Asn Tyr Leu Leu Gly Lys Phe Ser Gln Lys Thr Arg
```

```
            225                 230                 235                 240
    Trp Phe Ser Ile Val Pro Tyr Glu Thr Asn Asn Gln Glu Thr Phe Gly
                    245                 250                 255

Ala Leu Asp Leu Gly Gly Ala Ser Thr Gln Val Thr Phe Val Pro Gln
                260                 265                 270

Asn Gln Thr Ile Glu Ser Pro Asp Asn Ala Leu Gln Phe Arg Leu Tyr
                275                 280                 285

Gly Lys Asp Tyr Asn Val Tyr Thr His Ser Phe Leu Cys Tyr Gly Lys
            290                 295                 300

Asp Gln Ala Leu Trp Gln Lys Leu Ala Lys Asp Ile Gln Val Ala Ser
    305                 310                 315                 320

Asn Glu Ile Leu Arg Asp Pro Cys Phe His Pro Gly Tyr Lys Lys Val
                    325                 330                 335

Val Asn Val Ser Asp Leu Tyr Lys Thr Pro Cys Thr Lys Arg Phe Glu
                340                 345                 350

Met Thr Leu Pro Phe Gln Gln Phe Glu Ile Gln Gly Ile Gly Asn Tyr
                355                 360                 365

Gln Gln Cys His Gln Ser Ile Leu Glu Leu Phe Asn Thr Ser Tyr Cys
            370                 375                 380

Pro Tyr Ser Gln Cys Ala Phe Asn Gly Ile Phe Leu Pro Pro Leu Gln
    385                 390                 395                 400

Gly Asp Phe Gly Ala Phe Ser Ala Phe Tyr Phe Val Met Lys Phe Leu
                    405                 410                 415

Asn Leu Thr Ser Glu Lys Val Ser Gln Glu Lys Val Thr Glu Met Met
                420                 425                 430

Lys Lys Phe Cys Ala Gln Pro Trp Glu Glu Ile Lys Thr Ser Tyr Ala
                435                 440                 445

Gly Val Lys Glu Lys Tyr Leu Ser Glu Tyr Cys Phe Ser Gly Thr Tyr
            450                 455                 460

Ile Leu Ser Leu Leu Leu Gln Gly Tyr His Phe Thr Ala Asp Ser Trp
    465                 470                 475                 480

Glu His Ile His Phe Ile Gly Lys Ile Gln Gly Ser Asp Ala Gly Trp
                    485                 490                 495

Thr Leu Gly Tyr Met Leu Asn Leu Thr Asn Met Ile Pro Ala Glu Gln
                500                 505                 510

Pro Leu Ser Thr Pro Leu Ser His Ser Thr Tyr Val Phe Leu Met Val
                515                 520                 525

Leu Phe Ser Leu Val Leu Phe Thr Val Ala Ile Ile Gly Leu Leu Ile
            530                 535                 540

Phe His Lys Pro Ser Tyr Phe Trp Lys Asp Met Val
    545                 550                 555

<210> SEQ ID NO 3
<211> LENGTH: 16
<212> TYPE: DNA
<213> ORGANISM: Artificial Sequence
<220> FEATURE:
<223> OTHER INFORMATION: mRNA (Antisense) sequence

<400> SEQUENCE: 3
gtttgtgtga gagctt                                                      16

<210> SEQ ID NO 4
<211> LENGTH: 17
<212> TYPE: DNA
<213> ORGANISM: Artificial Sequence
```

```
<220> FEATURE:
<223> OTHER INFORMATION: mRNA (Antisense) sequence

<400> SEQUENCE: 4
cacttacgtt cactacc                                                  17

<210> SEQ ID NO 5
<211> LENGTH: 14
<212> TYPE: DNA
<213> ORGANISM: Artificial Sequence
<220> FEATURE:
<223> OTHER INFORMATION: mRNA (Antisense) sequence

<400> SEQUENCE: 5
ggcgaaattg caga                                                     14

<210> SEQ ID NO 6
<211> LENGTH: 14
<212> TYPE: DNA
<213> ORGANISM: Artificial Sequence
<220> FEATURE:
<223> OTHER INFORMATION: mRNA (Antisense) sequence

<400> SEQUENCE: 6
ctccagcgta agat                                                     14

<210> SEQ ID NO 7
<211> LENGTH: 14
<212> TYPE: DNA
<213> ORGANISM: Artificial Sequence
<220> FEATURE:
<223> OTHER INFORMATION: mRNA (Antisense) sequence

<400> SEQUENCE: 7
ttgaacactg cgat                                                     14

<210> SEQ ID NO 8
<211> LENGTH: 15
<212> TYPE: DNA
<213> ORGANISM: Artificial Sequence
<220> FEATURE:
<223> OTHER INFORMATION: mRNA (Antisense) sequence

<400> SEQUENCE: 8
gccataggca ccttc                                                    15

<210> SEQ ID NO 9
<211> LENGTH: 15
<212> TYPE: DNA
<213> ORGANISM: Artificial Sequence
<220> FEATURE:
<223> OTHER INFORMATION: mRNA (Antisense) sequence

<400> SEQUENCE: 9
ctatgctgaa ccacc                                                    15

<210> SEQ ID NO 10
<211> LENGTH: 15
<212> TYPE: DNA
<213> ORGANISM: Artificial Sequence
<220> FEATURE:
<223> OTHER INFORMATION: mRNA (Antisense) sequence

<400> SEQUENCE: 10
tgtagaggct ccccc                                                    15
```

```
<210> SEQ ID NO 11
<211> LENGTH: 15
<212> TYPE: DNA
<213> ORGANISM: Artificial Sequence
<220> FEATURE:
<223> OTHER INFORMATION: mRNA (Antisense) sequence

<400> SEQUENCE: 11
ttgcagagca ttatc                                                      15

<210> SEQ ID NO 12
<211> LENGTH: 15
<212> TYPE: DNA
<213> ORGANISM: Artificial Sequence
<220> FEATURE:
<223> OTHER INFORMATION: mRNA (Antisense) sequence

<400> SEQUENCE: 12
aggcgaaatt gcaga                                                      15

<210> SEQ ID NO 13
<211> LENGTH: 15
<212> TYPE: DNA
<213> ORGANISM: Artificial Sequence
<220> FEATURE:
<223> OTHER INFORMATION: mRNA (Antisense) sequence

<400> SEQUENCE: 13
tagacattgt agtcc                                                      15

<210> SEQ ID NO 14
<211> LENGTH: 15
<212> TYPE: DNA
<213> ORGANISM: Artificial Sequence
<220> FEATURE:
<223> OTHER INFORMATION: mRNA (Antisense) sequence

<400> SEQUENCE: 14
gagtgcctga tcctt                                                      15

<210> SEQ ID NO 15
<211> LENGTH: 15
<212> TYPE: DNA
<213> ORGANISM: Artificial Sequence
<220> FEATURE:
<223> OTHER INFORMATION: mRNA (Antisense) sequence

<400> SEQUENCE: 15 aatcccctg gagtg                                                       15

<210> SEQ ID NO 16
<211> LENGTH: 15
<212> TYPE: DNA
<213> ORGANISM: Artificial Sequence
<220> FEATURE:
<223> OTHER INFORMATION: mRNA (Antisense) sequence

<400> SEQUENCE: 16
agcgtaagat gtttt                                                      15

<210> SEQ ID NO 17
<211> LENGTH: 15
<212> TYPE: DNA
<213> ORGANISM: Artificial Sequence
<220> FEATURE:
<223> OTHER INFORMATION: mRNA (Antisense) sequence
```

```
<400> SEQUENCE: 17
actccagcgt aagat                                                     15

<210> SEQ ID NO 18
<211> LENGTH: 15
<212> TYPE: DNA
<213> ORGANISM: Artificial Sequence
<220> FEATURE:
<223> OTHER INFORMATION: mRNA (Antisense) sequence

<400> SEQUENCE: 18
tgatagcctt gcaga                                                     15

<210> SEQ ID NO 19
<211> LENGTH: 15
<212> TYPE: DNA
<213> ORGANISM: Artificial Sequence
<220> FEATURE:
<223> OTHER INFORMATION: mRNA (Antisense) sequence

<400> SEQUENCE: 19
agtccagccg gcgtc                                                     15

<210> SEQ ID NO 20
<211> LENGTH: 15
<212> TYPE: DNA
<213> ORGANISM: Artificial Sequence
<220> FEATURE:
<223> OTHER INFORMATION: mRNA (Antisense) sequence

<400> SEQUENCE: 20
ggacaatggt tgctc                                                     15

<210> SEQ ID NO 21
<211> LENGTH: 15
<212> TYPE: DNA
<213> ORGANISM: Artificial Sequence
<220> FEATURE:
<223> OTHER INFORMATION: mRNA (Antisense) sequence

<400> SEQUENCE: 21
cttgaacact gcgat                                                     15

<210> SEQ ID NO 22
<211> LENGTH: 15
<212> TYPE: DNA
<213> ORGANISM: Artificial Sequence
<220> FEATURE:
<223> OTHER INFORMATION: mRNA (Antisense) sequence

<400> SEQUENCE: 22
gagtacaact gaacc                                                     15

<210> SEQ ID NO 23
<211> LENGTH: 15
<212> TYPE: DNA
<213> ORGANISM: Artificial Sequence
<220> FEATURE:
<223> OTHER INFORMATION: mRNA (Antisense) sequence

<400> SEQUENCE: 23
gtaagccctg atgtt                                                     15

<210> SEQ ID NO 24
```

-continued

```
<211> LENGTH: 15
<212> TYPE: DNA
<213> ORGANISM: Artificial Sequence
<220> FEATURE:
<223> OTHER INFORMATION: mRNA (Antisense) sequence

<400> SEQUENCE: 24
tatggtacag ttggt                                                         15

<210> SEQ ID NO 25
<211> LENGTH: 16
<212> TYPE: DNA
<213> ORGANISM: Artificial Sequence
<220> FEATURE:
<223> OTHER INFORMATION: mRNA (Antisense) sequence

<400> SEQUENCE: 25
ctgactgaat ttgccc                                                        16

<210> SEQ ID NO 26
<211> LENGTH: 16
<212> TYPE: DNA
<213> ORGANISM: Artificial Sequence
<220> FEATURE:
<223> OTHER INFORMATION: mRNA (Antisense) sequence

<400> SEQUENCE: 26
actatgctga accacc                                                        16

<210> SEQ ID NO 27
<211> LENGTH: 16
<212> TYPE: DNA
<213> ORGANISM: Artificial Sequence
<220> FEATURE:
<223> OTHER INFORMATION: mRNA (Antisense) sequence

<400> SEQUENCE: 27
gactatgctg aaccac                                                        16

<210> SEQ ID NO 28
<211> LENGTH: 16
<212> TYPE: DNA
<213> ORGANISM: Artificial Sequence
<220> FEATURE:
<223> OTHER INFORMATION: mRNA (Antisense) sequence

<400> SEQUENCE: 28
gaggcgaaat tgcaga                                                        16

<210> SEQ ID NO 29
<211> LENGTH: 16
<212> TYPE: DNA
<213> ORGANISM: Artificial Sequence
<220> FEATURE:
<223> OTHER INFORMATION: mRNA (Antisense) sequence

<400> SEQUENCE: 29
agagtgcctg atcctt                                                        16

<210> SEQ ID NO 30
<211> LENGTH: 16
<212> TYPE: DNA
<213> ORGANISM: Artificial Sequence
<220> FEATURE:
<223> OTHER INFORMATION: mRNA (Antisense) sequence

<400> SEQUENCE: 30
```

```
gatagtttcc aatacc                                                      16

<210> SEQ ID NO 31
<211> LENGTH: 16
<212> TYPE: DNA
<213> ORGANISM: Artificial Sequence
<220> FEATURE:
<223> OTHER INFORMATION: mRNA (Antisense) sequence

<400> SEQUENCE: 31
tactccagcg taagat                                                      16

<210> SEQ ID NO 32
<211> LENGTH: 16
<212> TYPE: DNA
<213> ORGANISM: Artificial Sequence
<220> FEATURE:
<223> OTHER INFORMATION: mRNA (Antisense) sequence

<400> SEQUENCE: 32
atgtagccca aagtcc                                                      16

<210> SEQ ID NO 33
<211> LENGTH: 16
<212> TYPE: DNA
<213> ORGANISM: Artificial Sequence
<220> FEATURE:
<223> OTHER INFORMATION: mRNA (Antisense) sequence

<400> SEQUENCE: 33
catgtagccc aaagtc                                                      16

<210> SEQ ID NO 34
<211> LENGTH: 16
<212> TYPE: DNA
<213> ORGANISM: Artificial Sequence
<220> FEATURE:
<223> OTHER INFORMATION: mRNA (Antisense) sequence

<400> SEQUENCE: 34
ggacaatggt tgctca                                                      16

<210> SEQ ID NO 35
<211> LENGTH: 16
<212> TYPE: DNA
<213> ORGANISM: Artificial Sequence
<220> FEATURE:
<223> OTHER INFORMATION: mRNA (Antisense) sequence

<400> SEQUENCE: 35
agcctatgat ggccac                                                      16

<210> SEQ ID NO 36
<211> LENGTH: 16
<212> TYPE: DNA
<213> ORGANISM: Artificial Sequence
<220> FEATURE:
<223> OTHER INFORMATION: mRNA (Antisense) sequence

<400> SEQUENCE: 36
gccttgaaca ctgcga                                                      16

<210> SEQ ID NO 37
<211> LENGTH: 16
<212> TYPE: DNA
```

```
<213> ORGANISM: Artificial Sequence
<220> FEATURE:
<223> OTHER INFORMATION: mRNA (Antisense) sequence

<400> SEQUENCE: 37
accctgagtt gtaact                                                    16

<210> SEQ ID NO 38
<211> LENGTH: 16
<212> TYPE: DNA
<213> ORGANISM: Artificial Sequence
<220> FEATURE:
<223> OTHER INFORMATION: mRNA (Antisense) sequence

<400> SEQUENCE: 38
aggatagtct tgtctc                                                    16

<210> SEQ ID NO 39
<211> LENGTH: 16
<212> TYPE: DNA
<213> ORGANISM: Artificial Sequence
<220> FEATURE:
<223> OTHER INFORMATION: mRNA (Antisense) sequence

<400> SEQUENCE: 39
cctacccagg atagtc                                                    16

<210> SEQ ID NO 40
<211> LENGTH: 16
<212> TYPE: DNA
<213> ORGANISM: Artificial Sequence
<220> FEATURE:
<223> OTHER INFORMATION: mRNA (Antisense) sequence

<400> SEQUENCE: 40
ccctctcact aaatta                                                    16

<210> SEQ ID NO 41
<211> LENGTH: 16
<212> TYPE: DNA
<213> ORGANISM: Artificial Sequence
<220> FEATURE:
<223> OTHER INFORMATION: mRNA (Antisense) sequence

<400> SEQUENCE: 41
actccacact aatgct                                                    16

<210> SEQ ID NO 42
<211> LENGTH: 16
<212> TYPE: DNA
<213> ORGANISM: Artificial Sequence
<220> FEATURE:
<223> OTHER INFORMATION: mRNA (Antisense) sequence

<400> SEQUENCE: 42
gtcaatcctg ctcaac                                                    16

<210> SEQ ID NO 43
<211> LENGTH: 16
<212> TYPE: DNA
<213> ORGANISM: Artificial Sequence
<220> FEATURE:
<223> OTHER INFORMATION: mRNA (Antisense) sequence

<400> SEQUENCE: 43
cagtcaatcc tgctca                                                    16
```

<210> SEQ ID NO 44
<211> LENGTH: 17
<212> TYPE: DNA
<213> ORGANISM: Artificial Sequence
<220> FEATURE:
<223> OTHER INFORMATION: mRNA (Antisense) sequence

<400> SEQUENCE: 44
cttgccatag aggcgaa                                                  17

<210> SEQ ID NO 45
<211> LENGTH: 17
<212> TYPE: DNA
<213> ORGANISM: Artificial Sequence
<220> FEATURE:
<223> OTHER INFORMATION: mRNA (Antisense) sequence

<400> SEQUENCE: 45
tgccagagtg cctgatc                                                  17

<210> SEQ ID NO 46
<211> LENGTH: 17
<212> TYPE: DNA
<213> ORGANISM: Artificial Sequence
<220> FEATURE:
<223> OTHER INFORMATION: mRNA (Antisense) sequence

<400> SEQUENCE: 46
acgttcacta ccttctt                                                  17

<210> SEQ ID NO 47
<211> LENGTH: 17
<212> TYPE: DNA
<213> ORGANISM: Artificial Sequence
<220> FEATURE:
<223> OTHER INFORMATION: mRNA (Antisense) sequence

<400> SEQUENCE: 47
ttacgttcac taccttc                                                  17

<210> SEQ ID NO 48
<211> LENGTH: 17
<212> TYPE: DNA
<213> ORGANISM: Artificial Sequence
<220> FEATURE:
<223> OTHER INFORMATION: mRNA (Antisense) sequence

<400> SEQUENCE: 48
aaggtcactt acgttca                                                  17

<210> SEQ ID NO 49
<211> LENGTH: 17
<212> TYPE: DNA
<213> ORGANISM: Artificial Sequence
<220> FEATURE:
<223> OTHER INFORMATION: mRNA (Antisense) sequence

<400> SEQUENCE: 49
gccccaaaat cccctg                                                   17

<210> SEQ ID NO 50
<211> LENGTH: 17
<212> TYPE: DNA
<213> ORGANISM: Artificial Sequence
<220> FEATURE:

<223> OTHER INFORMATION: mRNA (Antisense) sequence

<400> SEQUENCE: 50
gagagaatgt aggtacc                                                      17

<210> SEQ ID NO 51
<211> LENGTH: 17
<212> TYPE: DNA
<213> ORGANISM: Artificial Sequence
<220> FEATURE:
<223> OTHER INFORMATION: mRNA (Antisense) sequence

<400> SEQUENCE: 51
ccctggatct tgccaat                                                      17

<210> SEQ ID NO 52
<211> LENGTH: 17
<212> TYPE: DNA
<213> ORGANISM: Artificial Sequence
<220> FEATURE:
<223> OTHER INFORMATION: mRNA (Antisense) sequence

<400> SEQUENCE: 52
aaagtccagc cggcgtc                                                      17

<210> SEQ ID NO 53
<211> LENGTH: 18
<212> TYPE: DNA
<213> ORGANISM: Artificial Sequence
<220> FEATURE:
<223> OTHER INFORMATION: negative control sequence

<400> SEQUENCE: 53
cgtttaggct atgtactt                                                     18

<210> SEQ ID NO 54
<211> LENGTH: 16
<212> TYPE: DNA
<213> ORGANISM: Artificial Sequence
<220> FEATURE:
<223> OTHER INFORMATION: mRNA (antisense) sequence

<400> SEQUENCE: 54
agtaatccac ccatag                                                       16

<210> SEQ ID NO 55
<211> LENGTH: 15
<212> TYPE: DNA
<213> ORGANISM: Artificial Sequence
<220> FEATURE:
<223> OTHER INFORMATION: mRNA (antisense) sequence

<400> SEQUENCE: 55
agtaatccac ccata                                                        15

<210> SEQ ID NO 56
<211> LENGTH: 15
<212> TYPE: DNA
<213> ORGANISM: Artificial Sequence
<220> FEATURE:
<223> OTHER INFORMATION: mRNA (antisense) sequence

<400> SEQUENCE: 56
gatccaaagc gccaa                                                        15

```
<210> SEQ ID NO 57
<211> LENGTH: 15
<212> TYPE: DNA
<213> ORGANISM: Artificial Sequence
<220> FEATURE:
<223> OTHER INFORMATION: mRNA (antisense) sequence

<400> SEQUENCE: 57
gttcgtagtc tccag                                                    15

<210> SEQ ID NO 58
<211> LENGTH: 15
<212> TYPE: DNA
<213> ORGANISM: Artificial Sequence
<220> FEATURE:
<223> OTHER INFORMATION: mRNA (antisense) sequence

<400> SEQUENCE: 58
ctgttcgtag tctcc                                                    15

<210> SEQ ID NO 59
<211> LENGTH: 15
<212> TYPE: DNA
<213> ORGANISM: Artificial Sequence
<220> FEATURE:
<223> OTHER INFORMATION: mRNA (antisense) sequence

<400> SEQUENCE: 59
ggtggcactg ttcgt                                                    15

<210> SEQ ID NO 60
<211> LENGTH: 15
<212> TYPE: DNA
<213> ORGANISM: Artificial Sequence
<220> FEATURE:
<223> OTHER INFORMATION: mRNA (antisense) sequence

<400> SEQUENCE: 60
gttatagcct tgcag                                                    15

<210> SEQ ID NO 61
<211> LENGTH: 15
<212> TYPE: DNA
<213> ORGANISM: Artificial Sequence
<220> FEATURE:
<223> OTHER INFORMATION: mRNA (antisense) sequence

<400> SEQUENCE: 61
cacattagct gcacg                                                    15

<210> SEQ ID NO 62
<211> LENGTH: 15
<212> TYPE: DNA
<213> ORGANISM: Artificial Sequence
<220> FEATURE:
<223> OTHER INFORMATION: mRNA (antisense) sequence

<400> SEQUENCE: 62
cctagttgtg tatac                                                    15

<210> SEQ ID NO 63
<211> LENGTH: 16
<212> TYPE: DNA
<213> ORGANISM: Artificial Sequence
<220> FEATURE:
<223> OTHER INFORMATION: mRNA (antisense) sequence
```

<400> SEQUENCE: 63
gtacaggttg gtgtga                                                      16

<210> SEQ ID NO 64
<211> LENGTH: 16
<212> TYPE: DNA
<213> ORGANISM: Artificial Sequence
<220> FEATURE:
<223> OTHER INFORMATION: mRNA (antisense) sequence

<400> SEQUENCE: 64
ccacttgtag atgtac                                                      16

<210> SEQ ID NO 65
<211> LENGTH: 16
<212> TYPE: DNA
<213> ORGANISM: Artificial Sequence
<220> FEATURE:
<223> OTHER INFORMATION: mRNA (antisense) sequence

<400> SEQUENCE: 65
gcccagcaga tagtta                                                      16

<210> SEQ ID NO 66
<211> LENGTH: 16
<212> TYPE: DNA
<213> ORGANISM: Artificial Sequence
<220> FEATURE:
<223> OTHER INFORMATION: mRNA (antisense) sequence

<400> SEQUENCE: 66
agatccaaag cgccaa                                                      16

<210> SEQ ID NO 67
<211> LENGTH: 16
<212> TYPE: DNA
<213> ORGANISM: Artificial Sequence
<220> FEATURE:
<223> OTHER INFORMATION: mRNA (antisense) sequence

<400> SEQUENCE: 67
cactgttcgt agtctc                                                      16

<210> SEQ ID NO 68
<211> LENGTH: 16
<212> TYPE: DNA
<213> ORGANISM: Artificial Sequence
<220> FEATURE:
<223> OTHER INFORMATION: mRNA (antisense) sequence

<400> SEQUENCE: 68
tggcactgtt cgtagt                                                      16

<210> SEQ ID NO 69
<211> LENGTH: 16
<212> TYPE: DNA
<213> ORGANISM: Artificial Sequence
<220> FEATURE:
<223> OTHER INFORMATION: mRNA (antisense) sequence

<400> SEQUENCE: 69
ggtacttctc ctttac                                                      16

<210> SEQ ID NO 70
<211> LENGTH: 16

```
<212> TYPE: DNA
<213> ORGANISM: Artificial Sequence
<220> FEATURE:
<223> OTHER INFORMATION: mRNA (antisense) sequence

<400> SEQUENCE: 70
agttatagcc ttgcag                                                     16

<210> SEQ ID NO 71
<211> LENGTH: 16
<212> TYPE: DNA
<213> ORGANISM: Artificial Sequence
<220> FEATURE:
<223> OTHER INFORMATION: mRNA (antisense) sequence

<400> SEQUENCE: 71
cgttgctgtc tttgat                                                     16

<210> SEQ ID NO 72
<211> LENGTH: 16
<212> TYPE: DNA
<213> ORGANISM: Artificial Sequence
<220> FEATURE:
<223> OTHER INFORMATION: mRNA (antisense) sequence

<400> SEQUENCE: 72
gctatactgc ctcttt                                                     16

<210> SEQ ID NO 73
<211> LENGTH: 16
<212> TYPE: DNA
<213> ORGANISM: Artificial Sequence
<220> FEATURE:
<223> OTHER INFORMATION: mRNA (antisense) sequence

<400> SEQUENCE: 73
agcattttgg catcac                                                     16

<210> SEQ ID NO 74
<211> LENGTH: 16
<212> TYPE: DNA
<213> ORGANISM: Artificial Sequence
<220> FEATURE:
<223> OTHER INFORMATION: mRNA (antisense) sequence

<400> SEQUENCE: 74
cctagttgtg tatact                                                     16

<210> SEQ ID NO 75
<211> LENGTH: 16
<212> TYPE: DNA
<213> ORGANISM: Artificial Sequence
<220> FEATURE:
<223> OTHER INFORMATION: mRNA (antisense) sequence

<400> SEQUENCE: 75
acatttctta ctcgtt                                                     16

<210> SEQ ID NO 76
<211> LENGTH: 17
<212> TYPE: DNA
<213> ORGANISM: Artificial Sequence
<220> FEATURE:
<223> OTHER INFORMATION: mRNA (antisense) sequence

<400> SEQUENCE: 76
```

```
gacctttcac ttggcat                                              17

<210> SEQ ID NO 77
<211> LENGTH: 17
<212> TYPE: DNA
<213> ORGANISM: Artificial Sequence
<220> FEATURE:
<223> OTHER INFORMATION: mRNA (antisense) sequence

<400> SEQUENCE: 77
cccagcagat agttaat                                              17

<210> SEQ ID NO 78
<211> LENGTH: 17
<212> TYPE: DNA
<213> ORGANISM: Artificial Sequence
<220> FEATURE:
<223> OTHER INFORMATION: mRNA (antisense) sequence

<400> SEQUENCE: 78
gcccagcaga tagttaa                                              17

<210> SEQ ID NO 79
<211> LENGTH: 17
<212> TYPE: DNA
<213> ORGANISM: Artificial Sequence
<220> FEATURE:
<223> OTHER INFORMATION: mRNA (antisense) sequence

<400> SEQUENCE: 79
atccaaagcg ccaaagg                                              17

<210> SEQ ID NO 80
<211> LENGTH: 17
<212> TYPE: DNA
<213> ORGANISM: Artificial Sequence
<220> FEATURE:
<223> OTHER INFORMATION: mRNA (antisense) sequence

<400> SEQUENCE: 80
tcgtagtctc cagtgcc                                              17

<210> SEQ ID NO 81
<211> LENGTH: 17
<212> TYPE: DNA
<213> ORGANISM: Artificial Sequence
<220> FEATURE:
<223> OTHER INFORMATION: mRNA (antisense) sequence

<400> SEQUENCE: 81
ttcgtagtct ccagtgc                                              17

<210> SEQ ID NO 82
<211> LENGTH: 17
<212> TYPE: DNA
<213> ORGANISM: Artificial Sequence
<220> FEATURE:
<223> OTHER INFORMATION: mRNA (antisense) sequence

<400> SEQUENCE: 82
tgttcgtagt ctccagt                                              17

<210> SEQ ID NO 83
<211> LENGTH: 17
<212> TYPE: DNA
<213> ORGANISM: Artificial Sequence
```

```
<220> FEATURE:
<223> OTHER INFORMATION: mRNA (antisense) sequence

<400> SEQUENCE: 83
ggtggcactg ttcgtag                                                  17

<210> SEQ ID NO 84
<211> LENGTH: 17
<212> TYPE: DNA
<213> ORGANISM: Artificial Sequence
<220> FEATURE:
<223> OTHER INFORMATION: mRNA (antisense) sequence

<400> SEQUENCE: 84
cgttgctgtc tttgatc                                                  17

<210> SEQ ID NO 85
<211> LENGTH: 17
<212> TYPE: DNA
<213> ORGANISM: Artificial Sequence
<220> FEATURE:
<223> OTHER INFORMATION: mRNA (antisense) sequence

<400> SEQUENCE: 85
gctatactgc ctctttc                                                  17

<210> SEQ ID NO 86
<211> LENGTH: 17
<212> TYPE: DNA
<213> ORGANISM: Artificial Sequence
<220> FEATURE:
<223> OTHER INFORMATION: mRNA (antisense) sequence

<400> SEQUENCE: 86
tacatttctt actcgtt                                                  17

<210> SEQ ID NO 87
<211> LENGTH: 18
<212> TYPE: DNA
<213> ORGANISM: Artificial Sequence
<220> FEATURE:
<223> OTHER INFORMATION: negative control sequence

<400> SEQUENCE: 87
cgtttaggct atgtactt                                                 18

<210> SEQ ID NO 88
<211> LENGTH: 16
<212> TYPE: DNA
<213> ORGANISM: Artificial Sequence
<220> FEATURE:
<223> OTHER INFORMATION: mRNA (Antisense)

<400> SEQUENCE: 88
agagtgcctg atcctt                                                   16

<210> SEQ ID NO 89
<211> LENGTH: 17
<212> TYPE: DNA
<213> ORGANISM: Artificial Sequence
<220> FEATURE:
<223> OTHER INFORMATION: mRNA (Antisense)

<400> SEQUENCE: 89
tacgttcact accttct                                                  17
```

<210> SEQ ID NO 90
<211> LENGTH: 16
<212> TYPE: DNA
<213> ORGANISM: Artificial Sequence
<220> FEATURE:
<223> OTHER INFORMATION: mRNA (Antisense)

<400> SEQUENCE: 90
gccctgatgt ttgaat          16

<210> SEQ ID NO 91
<211> LENGTH: 15
<212> TYPE: DNA
<213> ORGANISM: Artificial Sequence
<220> FEATURE:
<223> OTHER INFORMATION: mRNA (Antisense)

<400> SEQUENCE: 91
tagtaagccc tgatg           15

<210> SEQ ID NO 92
<211> LENGTH: 17
<212> TYPE: DNA
<213> ORGANISM: Artificial Sequence
<220> FEATURE:
<223> OTHER INFORMATION: mRNA (Antisense)

<400> SEQUENCE: 92
gtttgtgtga gagcttt         17

<210> SEQ ID NO 93
<211> LENGTH: 15
<212> TYPE: DNA
<213> ORGANISM: Artificial Sequence
<220> FEATURE:
<223> OTHER INFORMATION: mRNA (Antisense)

<400> SEQUENCE: 93
tttgtgtgag agctt           15

<210> SEQ ID NO 94
<211> LENGTH: 17
<212> TYPE: DNA
<213> ORGANISM: Artificial Sequence
<220> FEATURE:
<223> OTHER INFORMATION: mRNA (Antisense)

<400> SEQUENCE: 94
ggtttgtgtg agagctt         17

<210> SEQ ID NO 95
<211> LENGTH: 16

```
<212> TYPE: DNA
<213> ORGANISM: Artificial Sequence
<220> FEATURE:
<223> OTHER INFORMATION: mRNA (Antisense)

<400> SEQUENCE: 95
ggtttgtgtg agagct                                                      16

<210> SEQ ID NO 96
<211> LENGTH: 15
<212> TYPE: DNA
<213> ORGANISM: Artificial Sequence
<220> FEATURE:
<223> OTHER INFORMATION: mRNA (Antisense)

<400> SEQUENCE: 96
gtttgtgtga gagct                                                       15

<210> SEQ ID NO 97
<211> LENGTH: 15
<212> TYPE: DNA
<213> ORGANISM: Artificial Sequence
<220> FEATURE:
<223> OTHER INFORMATION: mRNA (Antisense)

<400> SEQUENCE: 97
ggtttgtgtg agagc                                                       15

<210> SEQ ID NO 98
<211> LENGTH: 17
<212> TYPE: DNA
<213> ORGANISM: Artificial Sequence
<220> FEATURE:
<223> OTHER INFORMATION: S6 control sequence

<400> SEQUENCE: 98
tctatcgtga tgtttct                                                     17

<210> SEQ ID NO 99
<211> LENGTH: 18
<212> TYPE: DNA
<213> ORGANISM: Artificial Sequence
<220> FEATURE:
<223> OTHER INFORMATION: mRNA (Antisense)

<400> SEQUENCE: 99
cgtttaggct atgtactt                                                    18
```